(12) United States Patent
Moffat et al.

(10) Patent No.: US 11,448,179 B2
(45) Date of Patent: Sep. 20, 2022

(54) BUOY WITH RADIATED WAVE REFLECTOR

(71) Applicant: Lone Gull Holdings, Ltd., Portland, OR (US)

(72) Inventors: Brian Lee Moffat, Portland, OR (US); Grzegorz Piotr Filip, Portland, OR (US)

(73) Assignee: Lone Gull Holdings, Ltd., Portland, OR (US)

( * ) Notice: Subject to any disclaimer, the term of this patent is extended or adjusted under 35 U.S.C. 154(b) by 5 days.

(21) Appl. No.: 17/510,849

(22) Filed: Oct. 26, 2021

(65) Prior Publication Data

US 2022/0136481 A1   May 5, 2022

Related U.S. Application Data

(60) Provisional application No. 63/107,451, filed on Oct. 30, 2020.

(51) Int. Cl.
| | |
|---|---|
| *F03B 13/10* | (2006.01) |
| *B63B 35/44* | (2006.01) |
| *F03B 13/16* | (2006.01) |

(52) U.S. Cl.
CPC .............. *F03B 13/16* (2013.01); *B63B 35/44* (2013.01); *B63B 2035/4466* (2013.01); *F05B 2240/93* (2013.01); *F05B 2240/95* (2013.01)

(58) Field of Classification Search
CPC . F03B 13/16; B63B 35/44; B63B 2035/4466; F05B 2240/93; F05B 2240/95
See application file for complete search history.

(56) References Cited

U.S. PATENT DOCUMENTS

| | | |
|---|---|---|
| 2010/0101474 A1 | 4/2010 | McEvoy et al. |
| 2014/0138953 A1 | 5/2014 | Franklin |
| 2019/0353139 A1 | 11/2019 | Sheldon-Coulson et al. |
| 2020/0056578 A1* | 2/2020 | Sheldon-Coulson ... B63B 35/44 |
| 2020/0182218 A1 | 6/2020 | Sheldon-Coulson et al. |

FOREIGN PATENT DOCUMENTS

| | | |
|---|---|---|
| EP | 2510226 B1 | 10/2012 |
| JP | 2006283648 A | 10/2006 |

OTHER PUBLICATIONS

Jan. 26, 2022 Int'l Search Report and Written Opinion (PCT/US2021/056773).

* cited by examiner

*Primary Examiner* — Joseph Ortega
(74) *Attorney, Agent, or Firm* — Fulwider Patton LLP

(57) ABSTRACT

Disclosed is buoyant wave energy capture device, adapted to float adjacent to an upper surface of a body of water over which waves pass, and adapted to capture a portion of the radiated waves created by its own rising and falling in response to incident and/or passing environmental waves. A power take off mechanism combined with the disclosed wave energy capture device may be tuned to a specific wave frequency, and thereby optimally extract energy from a motion of a single frequency, even the wave energy capture device may be excited and/or energized by waves of any of a relatively broad range of frequencies, thereby increasing the power-generation and cost efficiencies of such devices relative to wave energy conversion devices of the prior art.

20 Claims, 35 Drawing Sheets

US 11,448,179 B2

BUOY WITH RADIATED WAVE REFLECTOR

This application claims priority to U.S. Provisional Patent Application No. 63/107,451, filed Oct. 30, 2020, the content of which is incorporated by reference herein in its entirety.

BACKGROUND

Floating wave-energy-converter (WEC) buoys are typically designed to capture energy from passing waves and to convert a portion of that captured energy into electrical power. However, the efficiency with which such floating WEC buoys are able to capture and convert wave energy into electrical energy is often reduced by a tendency of such buoys to make and radiate waves, sometimes referred to as "damping radiation," and herein referred to as "radiated waves," as they move in response to passing wind waves and swell. For the purpose of this disclosure, unless otherwise noted, the "incident waves" will refer to environmental waves, e.g. those waves moving across the surface of an ocean in response to wind blowing across a fetch, and "radiated waves" will refer to waves created by an embodiment of the present disclosure as a consequence of a heaving of the embodiment, and/or vertical dislocation of the embodiment with respect to a surface of a body of water on which the embodiment floats and over which incident waves impinge upon the embodiment. When a buoy moves up and down, e.g. in response to passing waves, relative to the water on which it floats, the waterplane area and/or the displacement of the buoy may tend to change thereby tending to cause the buoy to produce waves, i.e. radiated waves, of its own. Such waves produced by a WEC buoy and/or a vessel in response to a heaving motion tend to radiate away from the WEC buoy and/or vessel, and travel across the surface of the body of water, and typically in a radial fashion. Such radiated waves produced by a WEC buoy and/or a vessel tend to diminish the kinetic and/or potential energy of the WEC buoy and/or vessel. Such energy losses typically mean that the efficiency with which a WEC buoy can harvest energy from incident waves is reduced relative to what it might be in the absence of its radiation of waves. And, such energy losses typically mean that the amount of energy that a vessel must consume in order to propel itself through water is increased relative to what it might be in the absence of its radiation of waves.

Waves moving across and/or over the surface of a body of water possess energy. Therefore, the production of waves requires and/or consumes energy. And, for this reason, when a floating WEC buoy not only captures energy from passing waves, but also produces and radiates waves, herein referred to as "radiated waves," in response to its own wave-induced bobbing, it loses some of the energy that it might have otherwise captured from the waves impinging on it. And, as a result of its production of radiated waves, the rate of bobbing of a floating WEC buoy can diminish over time at a faster decay rate than would happen in the absence of its production of radiated waves. This energy loss can be significant, and can it significantly reduce the amount of electrical power that a WEC buoy is able to produce with respect to a specific wave climate.

If the production and/or emission of radiated waves by a floating WEC buoy could be reduced or eliminated, then the amount of electrical power which such a radiated-wave-free WEC buoy could produce with respect to a given sea state might be increased, thereby increasing its efficiency of electrical power production, and reducing the average cost of the electrical power that it produces.

SUMMARY OF THE INVENTION

Disclosed are a novel type, design, and/or architecture of a buoy and/or other vessel, as well as a novel method, by which radiated waves produced by, and/or emanating from, such buoys and/or other vessels may be reduced or eliminated. The disclosed buoy and/or vessel design incorporates a skirt, wall, barrier, fence, surface, reflector, and/or obstruction, arrayed about a buoy and/or vessel, that will tend to reflect the buoy and/or vessel's radiated waves back to the buoy and/or vessel from which they emanated—thereby tending to trap those radiated waves within the gap between the skirt and the buoy and/or vessel, thus trapping, and creating the potential to recover, the energy stored within those radiated waves.

DETAILED DESCRIPTIONS OF THE EMBODIMENTS

Figure 1:
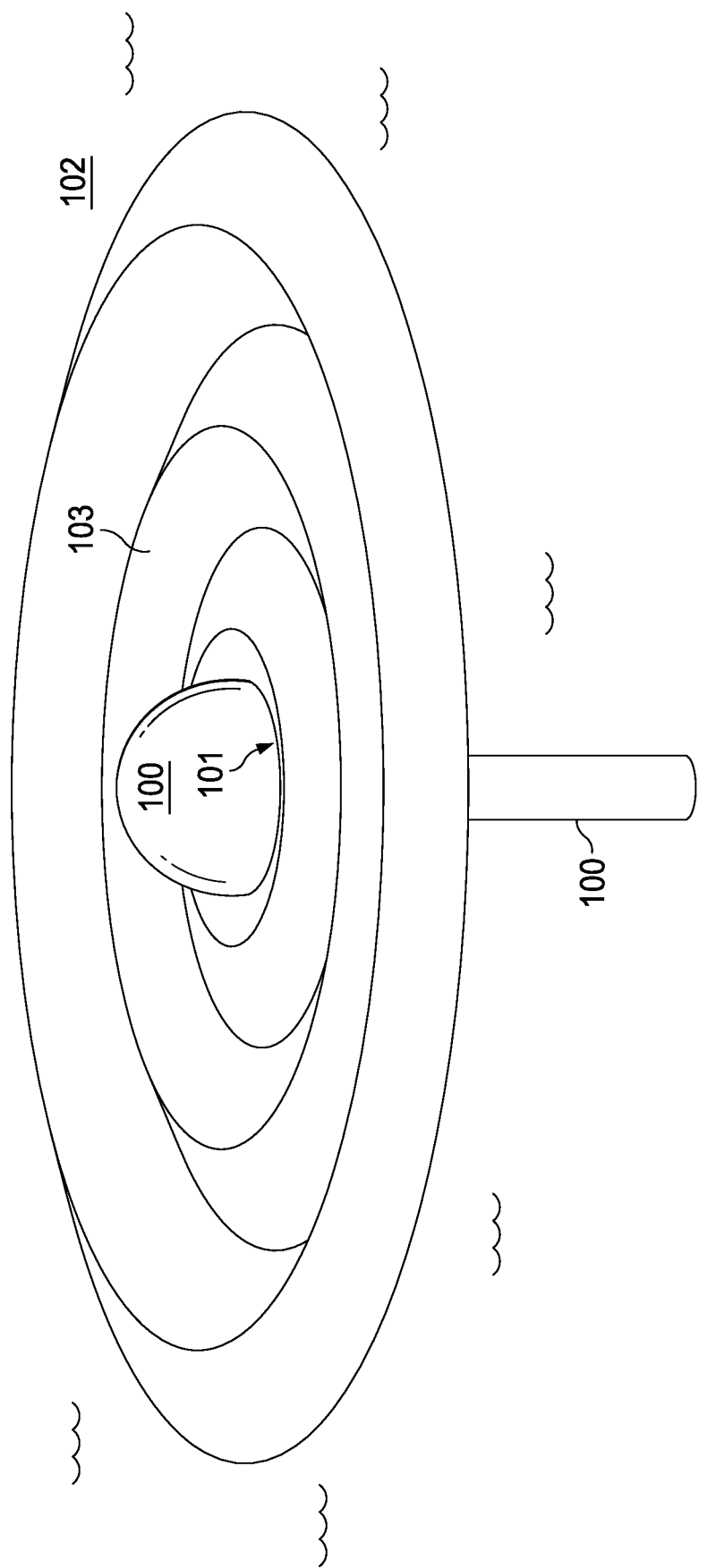
FIG. 1 is a perspective side view of a wave energy converter of the prior art producing radiated waves at an upper surface of a body of water on which it floats.

FIG. 1 shows a perspective side view of a WEC 100 of the prior art. The WEC of FIG. 1 is an embodiment of an inertial hydrodynamic wave engine akin to those disclosed in U.S. Pat. No. 11,118,559, the content of which is fully incorporated herein. The details of the methodologies for converting the wave energy to alternate energies is omitted herein for brevity. In response to a changing draft, a changing displacement, a changing relative height of a waterline 101, and/or (given the spherical shape of the WEC's bulbous portion) a changing waterplane area, in response to a bobbing of the WEC within the water 102, the WEC is radiating waves 103. These waves are sometimes referred to as "damping radiation" because they tend to dampen and/or diminish the energies of a vessel which lead to oscillatory motions at the surface of a body of water on which the vessel floats. While FIG. 1 illustrates the production of radiating waves by an inertial hydrodynamic wave engine, the same type of damping wave radiation tends to characterize the behaviors of other types of WECs, vessels, and/or floating objects as they absorb energy from passing waves, and then radiate some, if not all, of that absorbed energy in the form of radiating waves.

After being moved from its equilibrium depth and/or displacement by a vertical movement caused by a change in the buoyancy of the WEC that has been precipitated by a passing incident and/or environmental wave, the buoyant WEC tends to bob up and down cyclically. As it bobs up and down, the WEC is alternately submerged to a depth beneath and/or greater than its equilibrium and/or resting depth, thereby experiencing an upward buoyant force, and elevated to a height at which its depth is less than its equilibrium depth, thereby experiencing a downward gravitational force or weight. When submerged beneath its equilibrium depth, the WEC acquires buoyant potential energy and thereafter tends to accelerate upward. When elevated above its equilibrium depth, the mass of the WEC is not fully supported by its diminished displacement in the water on which it floats and the WEC acquires gravitational potential energy and thereafter tends to accelerate downward. In the absence of a radiation-related or viscous-drag-related loss of energy, or a capture of energy by the WEC itself, the WEC would be expected to continue its vertical oscillation for a very long time.

However, when a floating object with a positive displacement is partially submerged within a body of water to a depth greater than its equilibrium depth, as in response to the approach of a wave crest, the floating object tends to immediately produce a radiated wave, and the potential and kinetic energies imparted to the object by the passing wave are dissipated as they become invested into the creation of more and more, smaller and smaller, radiated waves. This illustrates the reality that radiated waves produced by a floating object, and especially by a wave-induced bobbing of a buoyant WEC, can rather quickly consume the potential and kinetic energies imparted to a WEC by a passing wave, and can therefore and/or thereby rather quickly diminish the wave-imparted energies with which a WEC might produce electrical energy or an alternate energy or product.

The radiated-wave trapping WEC disclosed herein which traps, to at least some degree, the radiated waves produced by its respective bulbous portion prior to an escape of those radiated waves into the environment, enables energy to be captured from incident and/or environmental waves with greater efficiency, and enables a WEC of the present disclosure to capture more energy from incident and/or environmental waves with respect to a given sea state, than does a WEC of the prior art.

Figure 2:
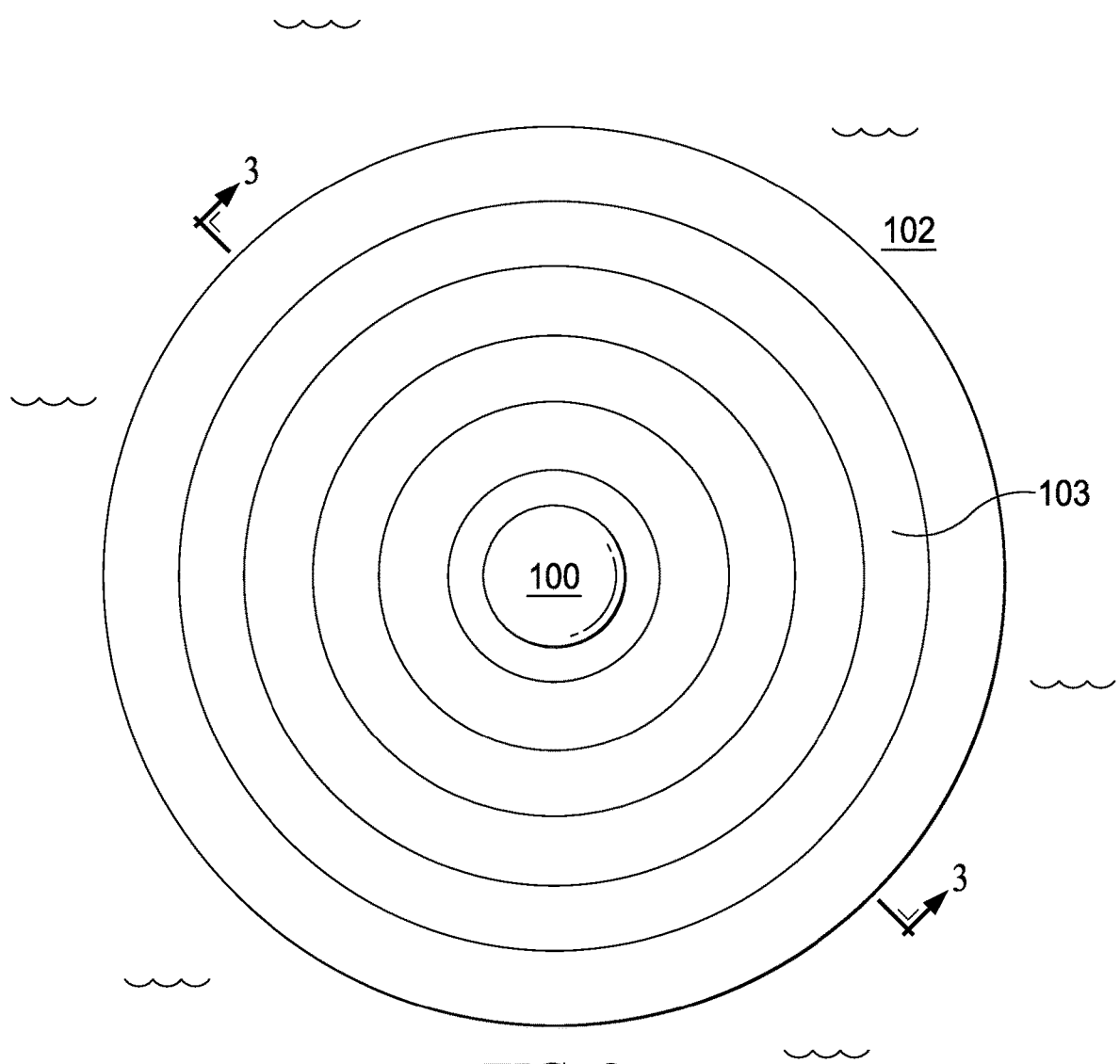
FIG. 2 is a top-down view of the prior art illustrated in FIG. 1.

FIG. 2 shows a top-down view of the same WEC 100 of the prior art illustrated in FIG. 1. FIG. 2 also shows the same radiating pattern of radiated waves emanating from the WEC of the prior art as a result of the WEC's vertical dislocation from, at, with, and/or relative to, the upper surface of the body of water 102 on which the WEC floats. The waves 103 radiating from the WEC 100 represent a loss of a portion of the WEC's kinetic and/or potential energy, and the WEC's production of these radiated waves diminishes, reduces, and/or lowers, the energy-capture efficiency of the WEC. In fact, if the WEC expends all of its kinetic and potential energy producing radiated waves, then it will thereafter float at the surface of the body of water on which it floats at its equilibrium waterline and it will thereafter be unable to produce any additional radiated waves (until kinetic and/or potential energy is again imparted to it by a passing incident and/or environmental wave, wind wave, swell, or some other energy input).

Figure 3:
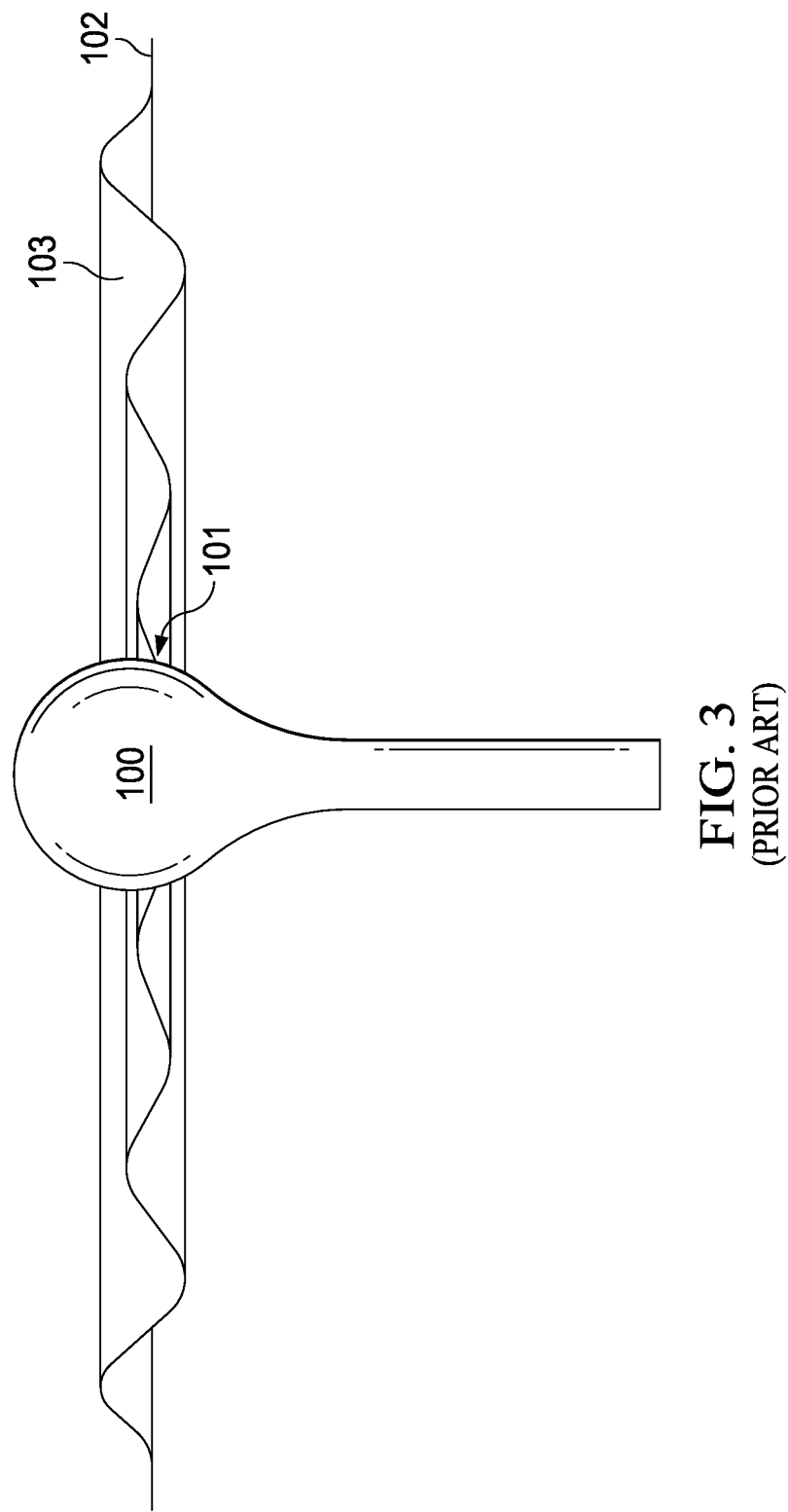
FIG. 3 is a side sectional view of the prior art illustrated in FIGS. 1 and 2.

FIG. 3 shows a side sectional view of the same WEC 100 of the prior art, and its radiated waves, as is illustrated in FIGS. 1 and 2, with the section plane being taken along line 3-3 of FIG. 2.

Figure 4:
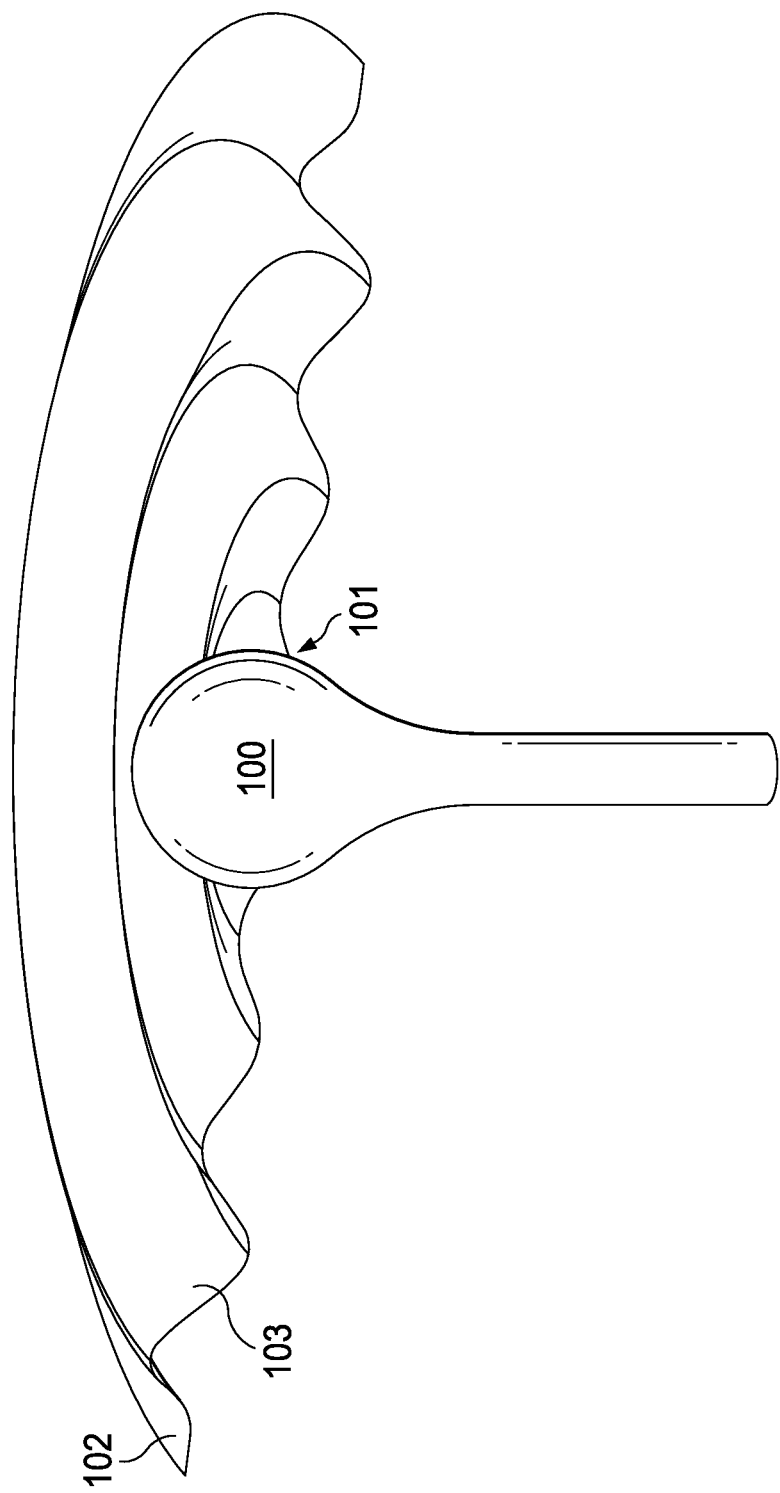
FIG. 4 is a perspective view of the sectional view of FIG. 3.

FIG. 4 shows a perspective view of the side sectional view illustrated in FIG. 3.

Figure 5:
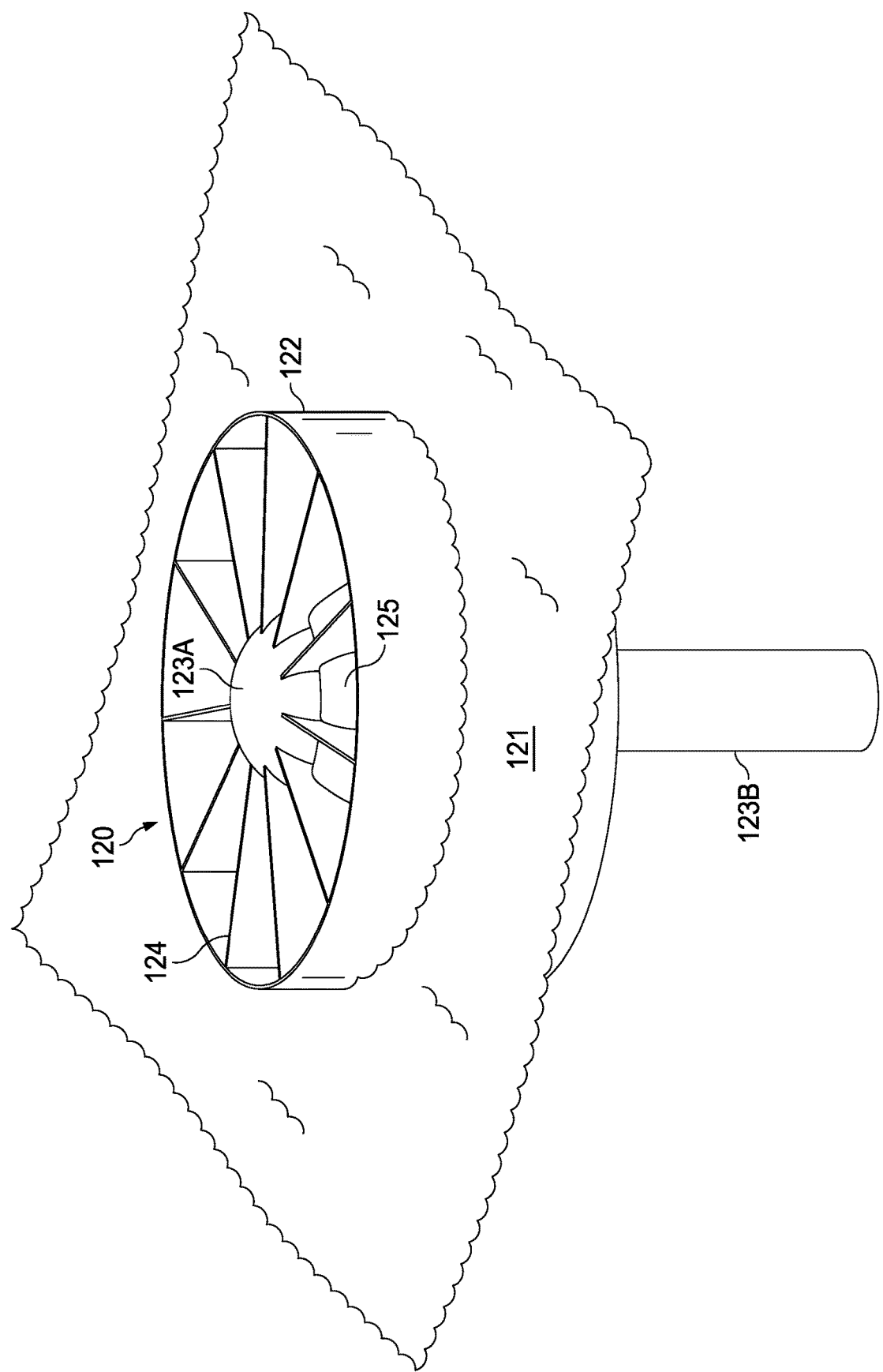
FIG. 5 is a perspective side view of a first embodiment of the present invention.

FIG. 5 shows a perspective side view of an embodiment 120 of the current disclosure. The embodiment illustrated in FIG. 5 is comprised in part of a WEC 123A,B similar to the WEC of the prior art illustrated in FIG. 1. And the embodiment 120 floats adjacent to an upper surface 121 of a body of water over which waves pass.

Unlike the WEC of the prior art illustrated in FIG. 1, the embodiment illustrated in FIG. 5 includes, incorporates, and/or utilizes, a wall 122 that surrounds the central WEC 123A, which wall 122 tends to reflect and trap waves radiated from the central WEC thereby tending to trap those radiated waves and the energy therein within the wall, and thereby prevent their radiation into and/or across the body of water on which the embodiment floats.

The buoyant embodiment 120 floats adjacent to an upper surface 121 of a body of water over which waves pass. An approximately cylindrical radiated-wave reflector 122 is rigidly connected to a central wave energy converter (WEC) 123A,B by a plurality of radial panels 124. The central WEC includes an upper bulbous portion 123A and a lower approximately cylindrical tubular portion 123B which depends from the upper bulbous portion 123A. The central WEC is adapted such that when the embodiment is placed within a body of water, the bulbous portion tends to float at the surface of that body of water, while the lower cylindrical and/or tubular portion of the central WEC remains submerged and while a longitudinal axis of that submerged tubular portion tends to be oriented approximately vertically and tends to remain approximately normal to the upper surface 121 of the body of water on which the embodiment floats.

Waves which radiate and/or emanate from the upper bulbous portion 123A of the central WEC in response to, and/or as a consequence of, alterations to the draft, the waterplane area, and/or the displacement, of the central WEC tend to be and/or become trapped within, and thereafter to be reflected back by, the embodiment's radiated-wave reflector 122. Radiated waves, e.g. 125, trapped within the annular pool of water partially enclosed within the annular gap between the central WEC and the radiated-wave reflector, i.e. within the reflector pool, tend to travel back and forth across the surface of the water within that reflector pool, thereby serially reflecting from the radiated-wave reflector back toward the central WEC, and from the central WEC back toward the radiated-wave reflector. (It will be understood that water enclosed within each of the eleven wedge-shaped regions respectively enclosed by lateral radial panels, e.g. 124, the bulbous portion 123A, and the radiated-wave reflector 122, can collectively be denoted as the "annular pool," even though in embodiments such as the embodiment illustrated in FIG. 5, radial panels divide the annular pool.)

In the embodiment illustrated in FIG. 5, the central WEC 123 (i.e. the central part of the embodiment, excluding the plurality of radial panels, e.g. 124, and radiated-wave reflector 122) is a pressurized-air-driven embodiment, where a pressurized air pocket and water reservoir are contained within bulbous portion 123A. It is to be understood that turbine ducts and other details of that technology are to be provided in the appropriate manners and relative positions, and may not be shown in the present figures. It will also be understood that the central WEC, alternately, can consist of, or be replaced by, any kind of wave energy converter, including but not limited to any wave energy converter of the prior art, including a spar-buoy oscillating water column, a two-body heaving point absorber, a heave-driven turbine, etc. Wave energy converters that capture energy primarily from heave motion will tend to benefit most from the technologies of the present disclosure.

Figure 6:
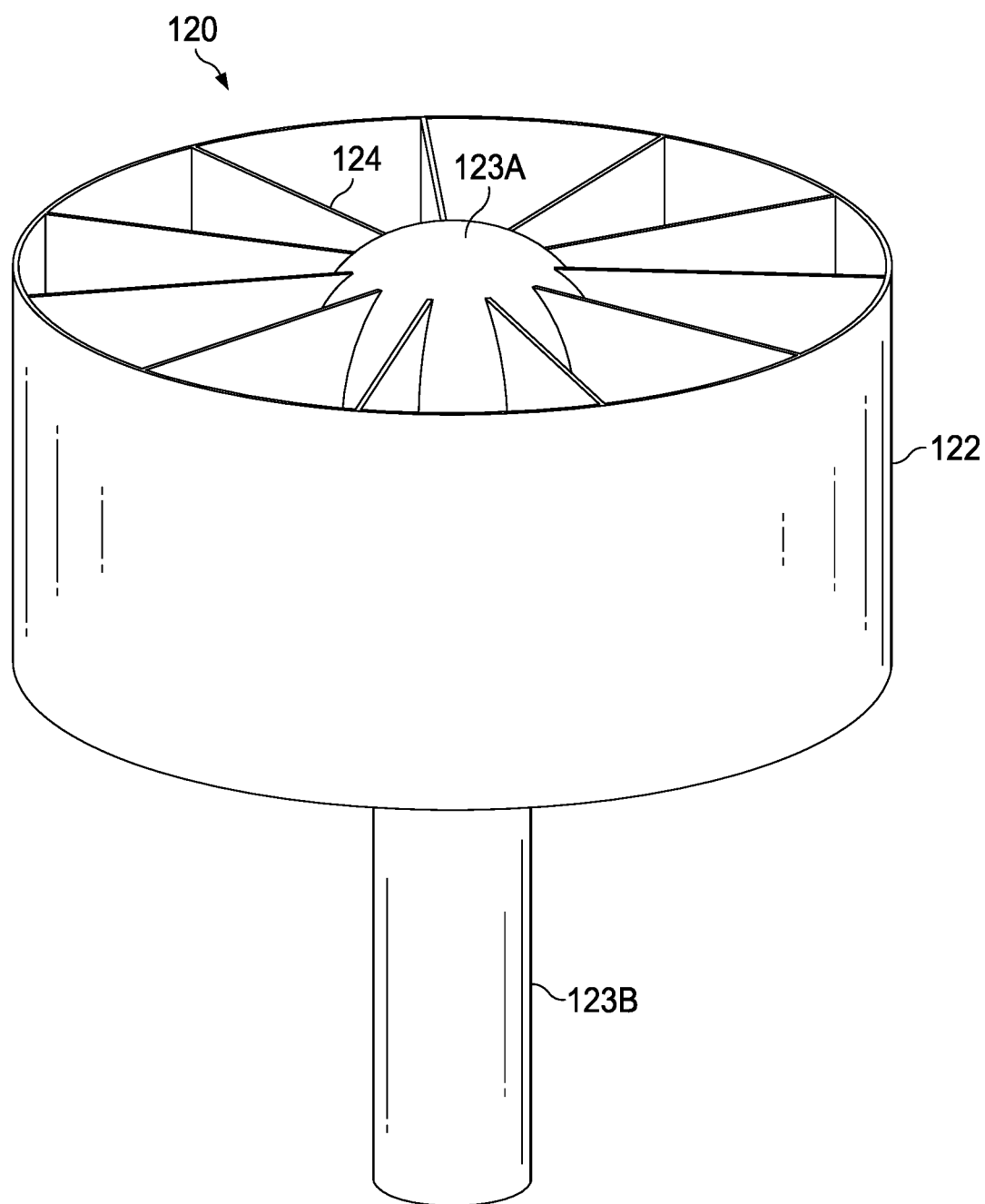
FIG. 6 is a perspective side view of the first embodiment.

FIG. 6 shows a perspective side view of the same embodiment 120 of the present disclosure that is illustrated in FIG. 5. However, in FIG. 6 the water on which the embodiment floats, as well as the portion of that water which would fill the annular gap between the central WEC 123 and the surrounding radiated-wave reflector 122, i.e. the reflector pool, have been omitted to facilitate a clearer examination of the apparatus.

Figure 7:
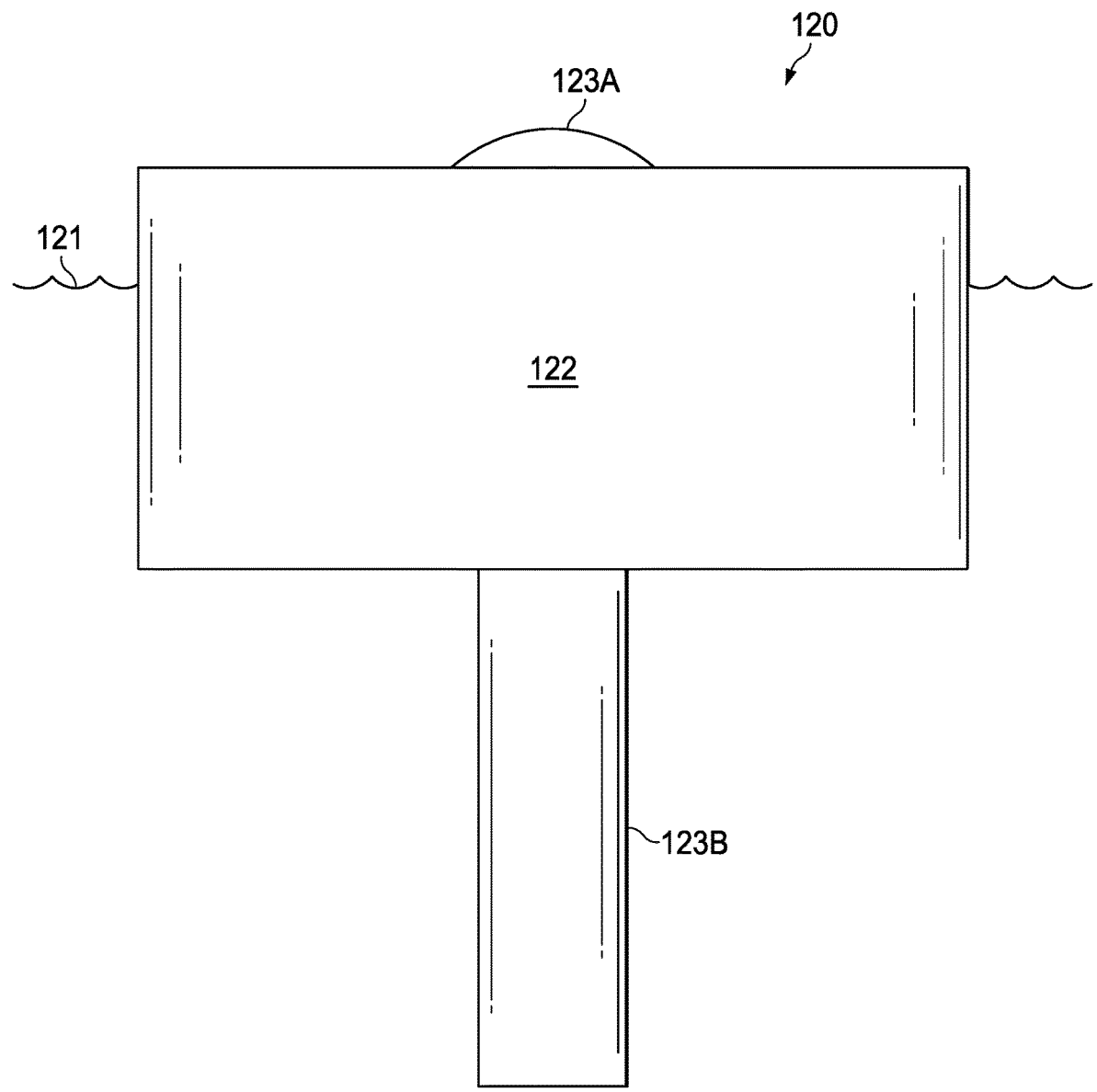
FIG. 7 is a side view of the first embodiment.

FIG. 7 shows a side view of the same embodiment 120 of the present disclosure that is illustrated in FIGS. 5 and 6.

Figure 8:
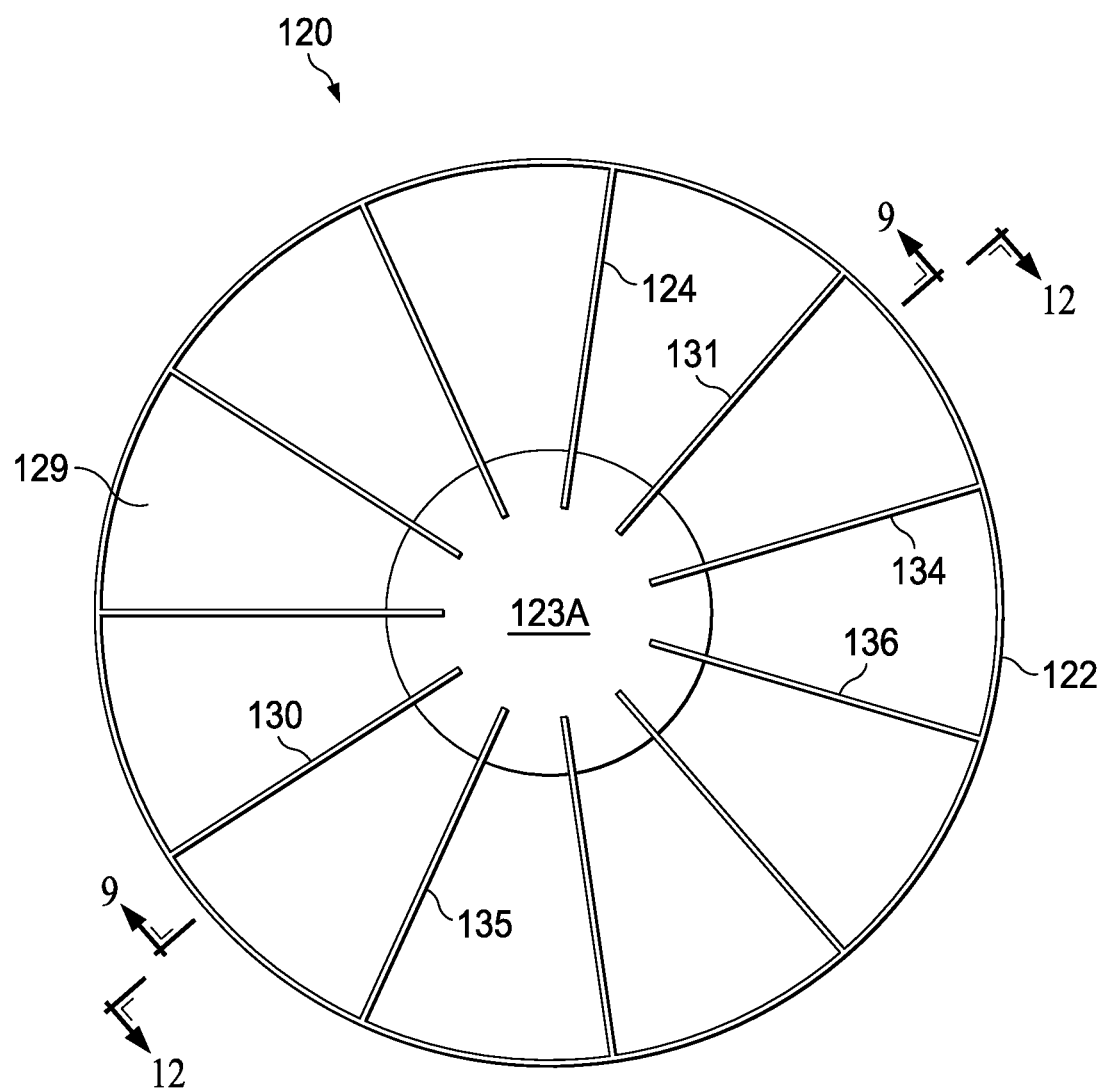
FIG. 8 is a top-down view of the first embodiment.

FIG. 8 shows a top-down view of the same embodiment 120 of the present disclosure that is illustrated in FIGS. 5-7. The embodiment's radiated-wave reflector 122 is approximately cylindrical with an open top and open bottom, meaning that the interior of the radiated-wave reflector (and/or each wedge-shaped compartment thereof) is fluidly connected to both the body of water (121 of FIG. 1) on which the embodiment floats and the atmosphere above that body of water. A discontinuous, divided, and/or partitioned, approximately annular, gap and/or space, i.e. a reflector pool 129, separates the centrally disposed upper bulbous portion 123A of the central wave energy converter (WEC) and the surrounding radiated-wave reflector. This annular gap and/or reflector pool is comprised of, and/or divided into, approximately pie-slice-shaped (i.e. wedge-shaped) tubular segments by a plurality of approximately vertical radial panels, e.g. 124, 130, 131, and 134-136, which connect the central WEC to the radiated-wave reflector.

Figure 9:
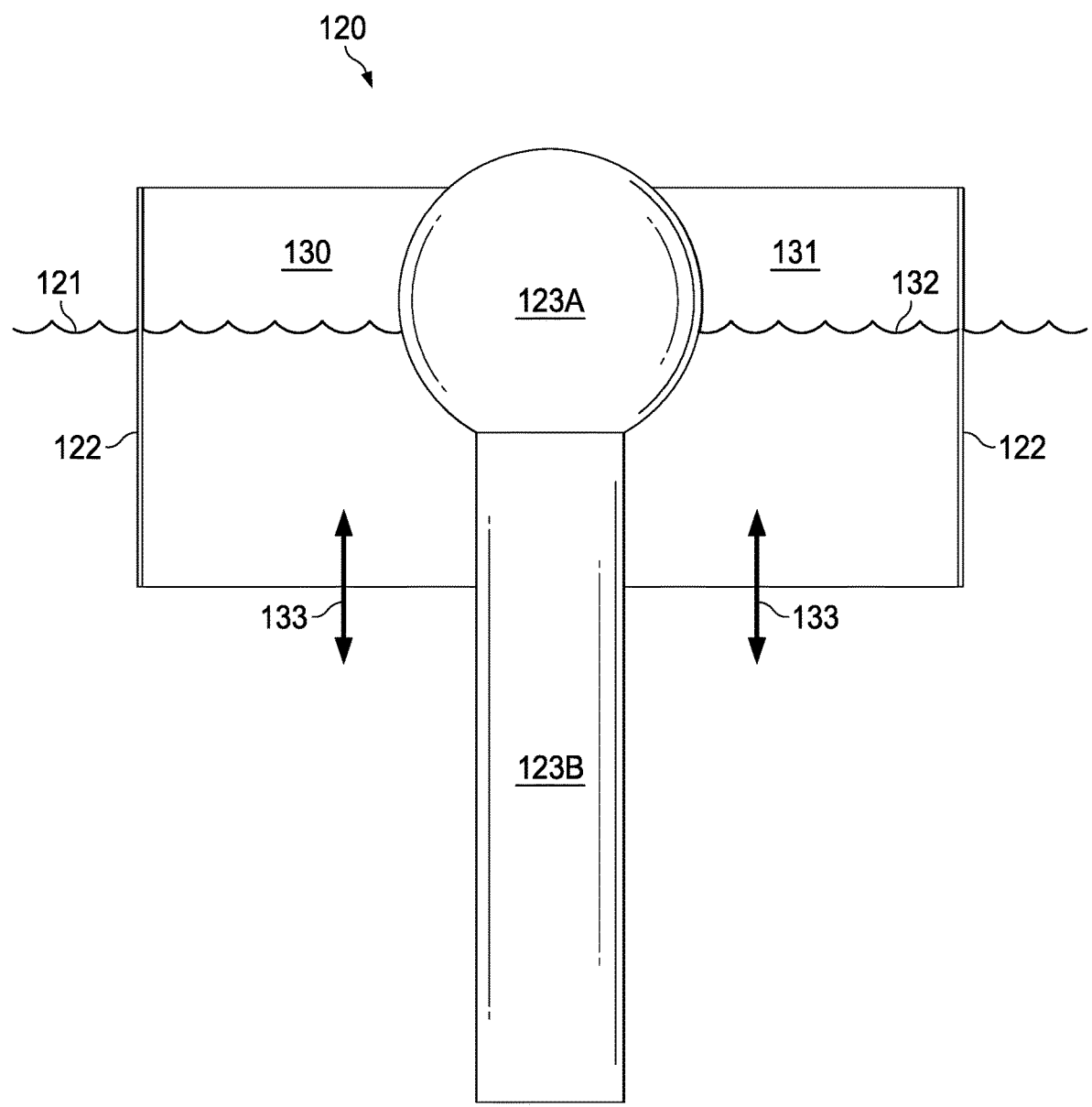
FIG. 9 is a side sectional view of the first embodiment.

FIG. 9 shows a side sectional view of the same embodiment 120 of the present disclosure that is illustrated in FIGS. 5-8 with the section plane being taken along line 9-9 of FIG. 8. Note that the water 132 partially and/or laterally enclosed and/or trapped within the embodiment's radiated-wave reflector 122, i.e. within the embodiment's reflector pool, is fluidly connected to the water 121 outside the embodiment, and water is able to freely flow 133 between the interior and exterior of the radiated-wave reflector enclosure, and/or into and out of the embodiment's reflector pool.

The radiated-wave reflector 122, and the radial panels e.g. 130 and 131, of the embodiment illustrated in FIGS. 5-9 are made of steel and are negatively buoyant. The embodiment as a whole is buoyant because of buoyancy of the bulbous upper portion 123A of the central WEC. Embodiments of the present disclosure may be fabricated, fashioned, created, manufactured, and/or made, of a wide variety of materials, and/or combination of materials, including, but not limited to: steel, iron, carbon (e.g. nanotubes and/or fiber), plastic, aluminum, copper, composite material, cementitious material, and resin. Embodiments of the present disclosure may be fabricated, fashioned, created, manufactured, and/or made, of a wide variety of materials, and/or combination of materials, some of which may be positively buoyant, negatively buoyant, and/or neutrally buoyant. All such embodiments are included within the scope of the present disclosure.

An embodiment of the present disclosure similar to the one illustrated in FIGS. 5-9 comprises a radiated-wave reflector 122 which is hollow and/or filled with a buoyant material (e.g. structural foam) such that the radiated-wave reflector is positively buoyant. An embodiment of the present disclosure similar to the one illustrated in FIGS. 5-9 comprises a plurality of radial panels, e.g. 124, 130, 131, and 134-136, wherein at least one or more are hollow and/or filled with a buoyant material (e.g. structural foam) such that one or more of the radial panels are positively buoyant. Another embodiment of the present disclosure similar to the one illustrated in FIGS. 5-9 comprises a radiated-wave reflector, and a plurality of radial panels, wherein that radiated-wave reflector and plurality of radial panels are approximately neutrally buoyant.

The scope of the present disclosure includes, but is not limited to, embodiments which incorporate, include, and/or utilize, radiated-wave reflectors fabricated of any material, as well as radiated-wave reflectors fabricated so as to be solid, and those fabricated so as to include voids filled with gas, foam, and/or other buoyant and/or structural materials. The scope of the present disclosure includes, but is not limited to, embodiments which incorporate, include, and/or utilize, radiated-wave reflectors fabricated of porous materials. The scope of the present disclosure includes, but is not limited to, embodiments which incorporate, include, and/or utilize, radiated-wave reflectors fabricated of flexible materials. The scope of the present disclosure is not limited to, and/or by, the structural design and/or material of which an embodiment's radiated-wave reflector is fabricated.

The scope of the present disclosure includes, but is not limited to, embodiments which incorporate, include, and/or utilize, radiated-wave reflectors of any width, height, thickness, cross-sectional shape, cross-sectional area, and waterplane area; including radiated-wave reflectors characterized by irregular, inconstant, changing, graduated, and/or variable, widths, heights, thicknesses, and cross-sectional shapes and/or areas. The scope of the present disclosure is not limited to, and/or by, the shape, design, size, and/or form, of an embodiment's radiated-wave reflector.

The scope of the present disclosure includes, but is not limited to, embodiments which incorporate, include, and/or utilize, radiated-wave reflectors which extend to any depth and/or draft below, and those which rise to any height above, the embodiment's mean, nominal, resting, and/or average waterline; including radiated-wave reflectors characterized by irregular, inconstant, changing, graduated, and/or variable, depths below, and heights above, the embodiment's mean, nominal, resting, and/or average waterline. The scope of the present disclosure is not limited to, and/or by, the relative position, orientation, configuration, alignment, and/or disposition, of an embodiment's radiated-wave reflector.

The scope of the present disclosure includes, but is not limited to, embodiments which incorporate, include, and/or utilize, radiated-wave reflectors which are rigid. The scope of the present disclosure includes, but is not limited to, embodiments which incorporate, include, and/or utilize, radiated-wave reflectors which are comprised of interconnected rigid panels. The scope of the present disclosure includes, but is not limited to, embodiments which incorporate, include, and/or utilize, radiated-wave reflectors which are flexible, and/or comprised of flexible panels, including, but not limited to those flexible radiated-wave reflectors comprised in whole or in part of fabrics, and/or woven materials. The scope of the present disclosure includes, but is not limited to, embodiments which incorporate, include, and/or utilize, radiated-wave reflectors which are comprised, in whole or in part, of assemblages of rigid tanks, cylinders, tubes, and/or pipes; as well as those comprised, in whole or in part, of inflatable chambers, tubes, and/or balloons.

The scope of the present disclosure includes, but is not limited to, embodiments which incorporate, include, and/or utilize, radiated-wave reflectors which are collapsible and/or deployable, e.g. through the use of folding radial panels and radiated-wave reflectors.

The scope of the present disclosure includes, but is not limited to, embodiments which incorporate, include, and/or utilize, radiated-wave reflectors which have inner surfaces (i.e. the broad surfaces proximate to the reflector pool and central WEC) that are approximately flat, as well as radiated-wave reflectors which have inner surfaces that are convex, concave, curved, and/or wedge-shaped. The scope of the present disclosure is not limited to, and/or by, the cross-sectional shape, design, and/or form, of an embodiment's radiated-wave reflector.

The radiated-wave reflector 122 of the embodiment illustrated in FIGS. 5-9 is approximately cylindrical. However, the scope of the present disclosure includes, but is not limited to, similar embodiments which incorporate, include, and/or utilize, radiated-wave reflectors of any shape, including, but not limited to, radiated-wave reflectors that have cross-sectional shapes that are: elliptical, parabolic, and hyperbolic.

Figure 10:
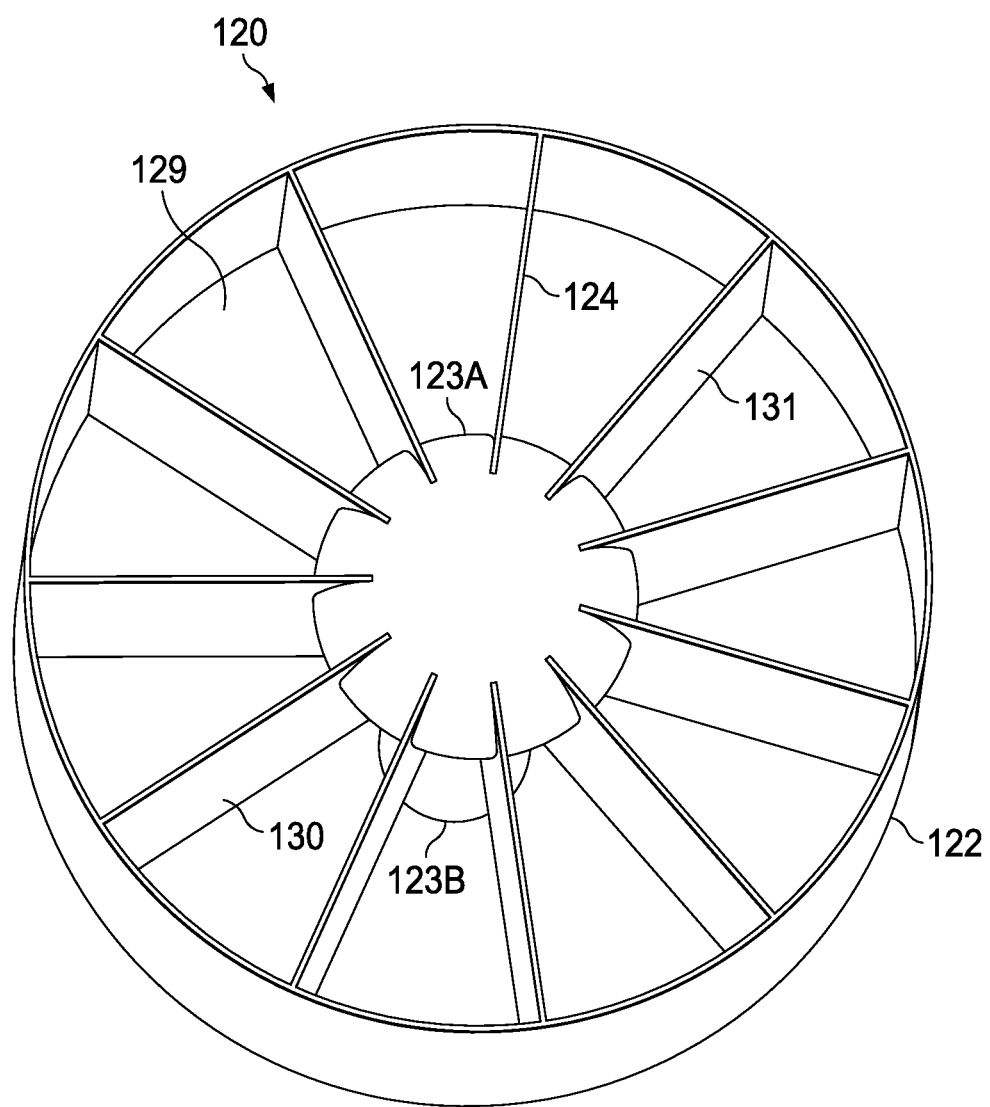
FIG. 10 is a perspective top-down view of the first embodiment.

FIG. 10 shows a perspective top-down view of the same embodiment 120 of the present disclosure that is illustrated in FIGS. 5-9.

Figure 11:
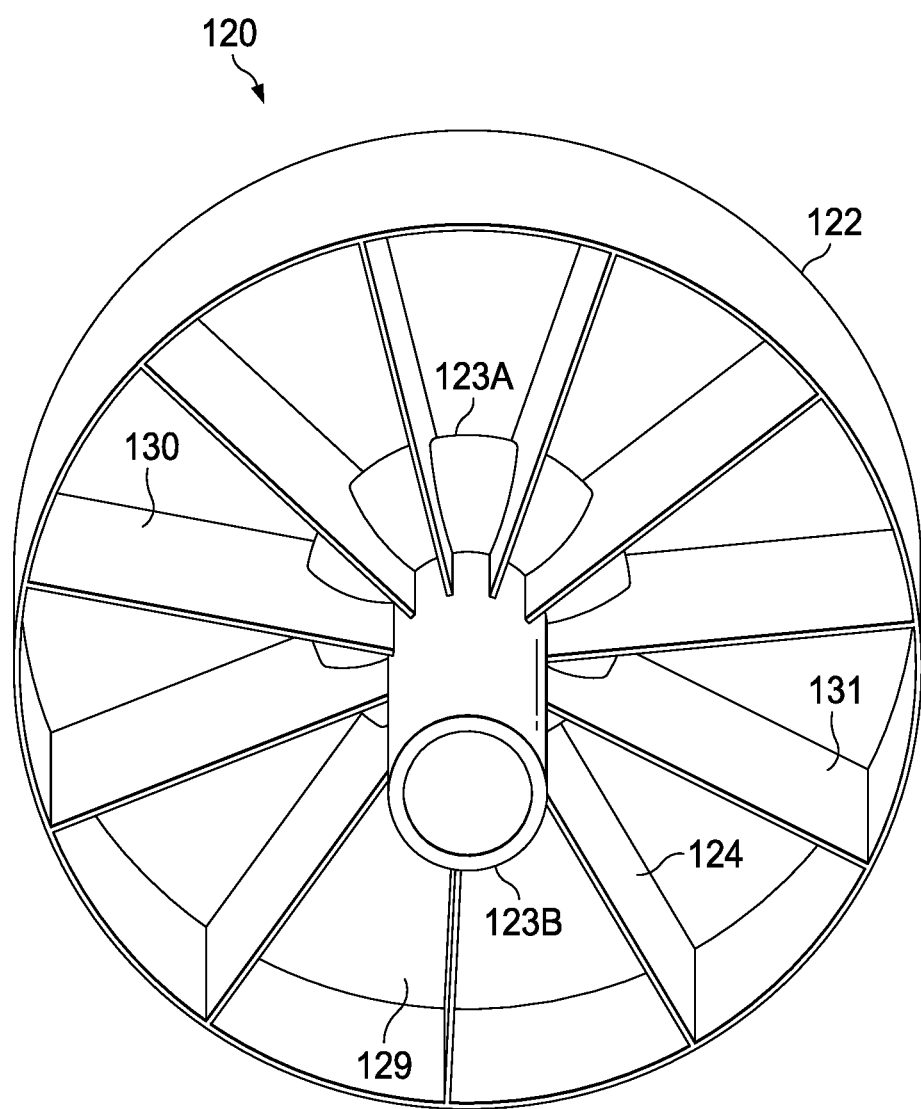
FIG. 11 is a perspective bottom-up view of the first embodiment.

FIG. 11 shows a perspective bottom-up view of the same embodiment 120 of the present disclosure that is illustrated in FIGS. 5-10.

Figure 12:
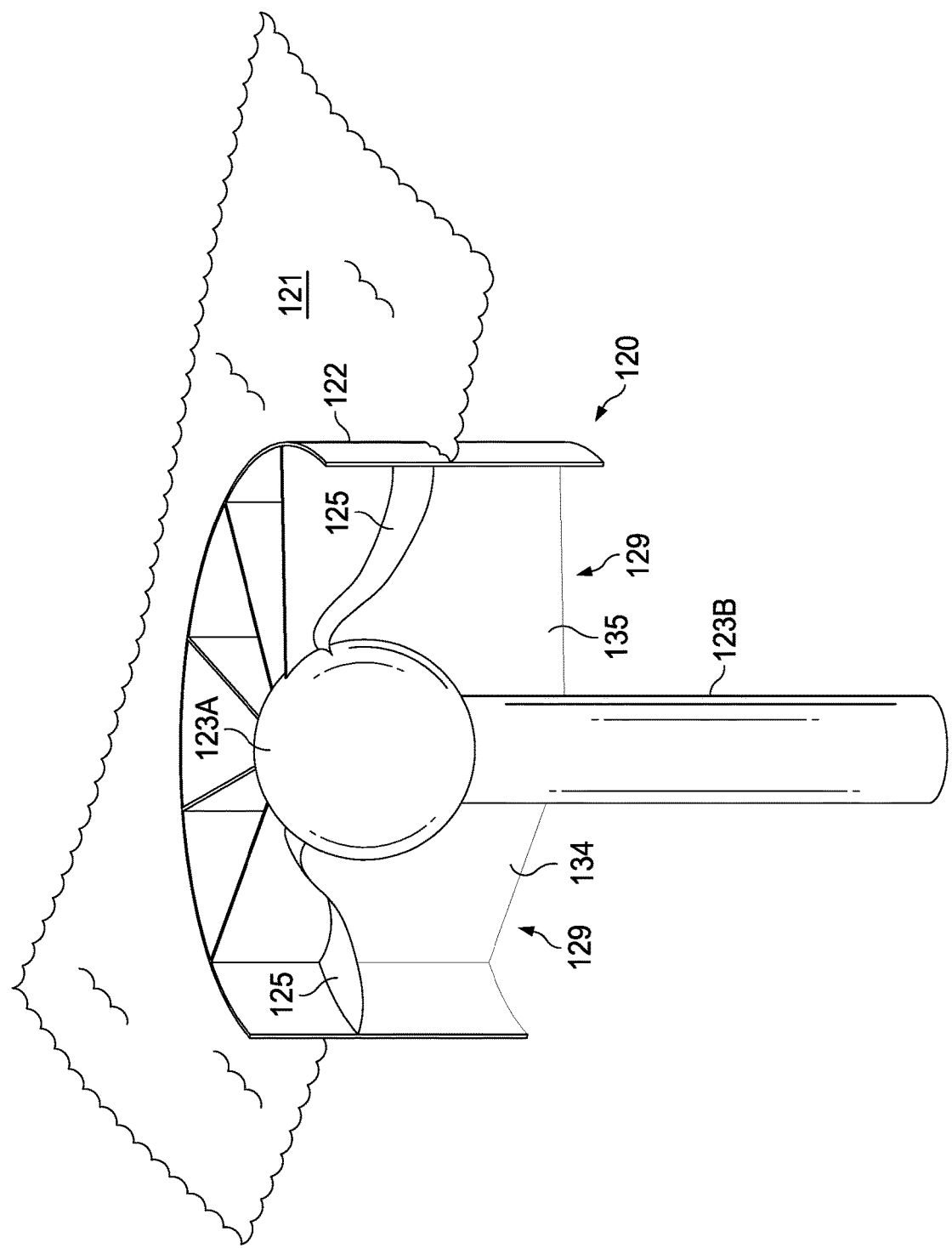
FIG. 12 is a perspective side sectional view of the first embodiment.

FIG. 12 shows a perspective side sectional view of the same embodiment 120 of the present disclosure that is illustrated in FIGS. 5-11 with the section plane being taken along line 12-12 of FIG. 8. Note that the water comprising the embodiment's reflector pool is partially (i.e. laterally but not vertically) enclosed and/or trapped within the embodiment's radiated-wave reflector 122 and is manifesting oscillations and waves of a relatively short wavelength and/or high frequency, while the water 121 outside the radiated-wave reflector, i.e. the water on which the embodiment floats, is manifesting oscillations and waves of a relatively long wavelength and/or low frequency. When incident and/or environmental waves of relatively low frequencies excite and/or move the embodiment, then the moved embodiment tends to respond by oscillating in a harmonic fashion at an approximately embodiment-specific characteristic, natural, and/or resonant frequency that tends to be a different and higher frequency than the most energetic frequencies of the driving incident and/or environmental waves.

As the embodiment 120 bobs up and down at and/or across the upper surface 121 of the body of water on which it floats, the upper buoyant bulbous portion 123A of the central WEC tends to produce radiated waves 125. Because of the relative short wavelength(s) of those radiated waves, and because of their correspondingly shallow wave base(s) (i.e. the depth below a surface wave where the amplitude of the motion of a wave has diminished to approximately 4% of the amplitude of its surface motion), those radiated waves are unable to pass by, pass out of, and/or escape, the embodiment's radiated-wave reflector 122, at least in part because the depth of the radiated-wave reflector is no less than the depth of the wave base of those radiated waves.

By contrast, waves of longer wavelength which pass over the surface 121 of the water on which the embodiment floats, and from which the embodiment extracts energy, tend to interact with, and impart energy to, the embodiment 120 despite the presence of the embodiment's radiated-wave reflector 122, at least in part because the wave bases of those longer-wavelength incident and/or environmental waves are substantially greater than the depth of the radiated-wave reflector.

The radiated-wave reflector 122 tends to obstruct and exclude waves traveling past the outside of the reflector, just as it tends to trap, within the reflector, waves whose wavelengths are no more than double the depth of the radiated-wave reflector, i.e. since the wave bases of those waves tends to extend down to but not deeper than the bottommost edge of the radiated-wave reflector. By contrast, the radiated-wave reflector is partially and/or effectively transparent to waves whose wavelengths are sufficiently long so as to have wave bases, and to transmit wave motion, to depths exceeding the depth of a bottommost edge of the radiated-wave reflector.

By configuring an embodiment of the present disclosure to have a radiated-wave reflector with a bottommost edge at a specific nominal depth below the surface of the body of water on which the embodiment floats, the embodiment can be designed to trap, within its radiated-wave reflector, radiated waves having wavelengths below a threshold critical radiated-wave reflector wavelength, while allowing the embodiment's central WEC to remain responsive to, and to extract energy from, passing incident and/or environmental waves having wavelengths greater than the threshold critical radiated-wave reflector wavelength. Thus, the present disclosure enables the design of WECs which are able to be responsive to, and extract energy from, waves of wavelengths characteristic of a deployment site or area, while also avoiding energy losses through, resulting from, and/or caused by, the production and dispersion of radiated waves of wavelengths characteristic of the embodiment's resonant bobbing motions.

The scope of the present disclosure includes, but is not limited to, embodiments which incorporate, include, and/or utilize, central WECs or incorporated WECs of any type, category (e.g. point-absorber), size, nameplate capacity, design, shape, and/or power-take-off mechanism. The scope of the present disclosure is not limited to, and/or by, the type, category (e.g. point-absorber), size, nameplate capacity, design, shape, and/or power-take-off mechanism, of an embodiment's central or incorporated WEC.

The scope of the present disclosure includes, but is not limited to, embodiments which incorporate, include, and/or utilize, buoyant vessels of any type, category (e.g. autonomous ship or surface vessel), size, draft, waterplane area, application (e.g. surveillance, and transport), design, shape, and/or propulsion mechanism (whether active, e.g. electrically-powered propeller, or passive, e.g. wave-driven flap, and/or rigid sail). The scope of the present disclosure is not limited to, and/or by, the type, category, size, draft, waterplane area, application, design, shape, and/or propulsion mechanism, of an embodiment's buoyant vessel.

Many attributes of an embodiment may be designed, altered, configured, and/or implemented, so as to produce within the reflector pool radiated waves of a particular desirable wavelength, period, and/or frequency. The attributes of an embodiment that might influence, alter, determine, and/or control the character of the radiated waves it produces within its reflector pool, as well as other of its operational behaviors and performance, include, but are not limited to: the radius of the radiated-wave reflector 112; the radius of the upper bulbous portion 113A; the vertical cross-sectional shape of the upper bulbous portion; the average density of the embodiment; and the draft or nominal depth of its radiated-wave reflector. The scope of the present disclosure includes embodiments exhibiting any and all values of these attributes, as well as any and every combination of such attribute values.

The selection of a nominal depth or draft of an embodiment's radiated-wave reflector 112 is important. The lesser the depth or draft of the radiated-wave reflector, the more easily excited an embodiment is by passing incident and/or environmental waves, especially with respect to incident and/or environmental waves of relatively short wavelengths. However, if the depth or draft of the radiated-wave reflector is less than approximately one-half the wavelength of the radiated waves that it tends to produce within its reflector pool, then a non-trivial amount and/or portion of the energy contained within those radiated waves may be able to escape the reflector pool. By contrast, the greater the depth or draft of the radiated-wave reflector, the less easily incident and/or environmental waves will excite an embodiment, especially with respect to incident and/or environmental waves of relatively short wavelengths.

The scope of the present disclosure includes, but is not limited to, embodiments which are free-floating, self-propelled, towed, and moored. The scope of the present disclosure is not limited to, and/or by, the position, and/or mobility, of an embodiment.

Figure 13:
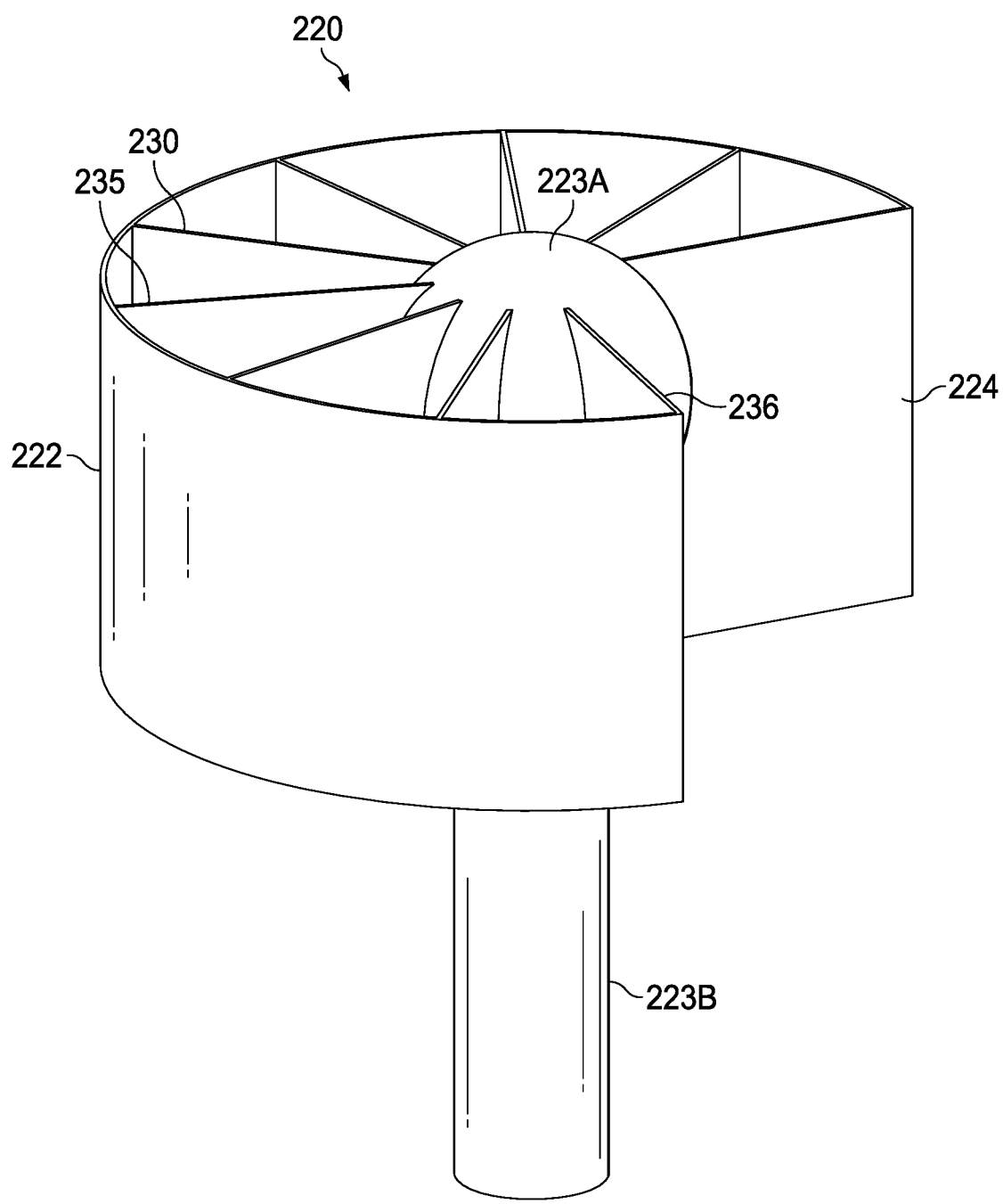
FIG. 13 is a perspective side view of a second embodiment of the present invention.

FIG. 13 shows a perspective side view of an alternate configuration 220 of the embodiment (120 in FIGS. 5-12) of the present disclosure that is illustrated in FIGS. 5-12. The alternate embodiment 220 illustrated in FIG. 13 is missing two of the radial panels, i.e. panels 131 and 134, incorporated within the embodiment 120 illustrated in FIGS. 5-12. Also, the radiated-wave reflector 222 of the alternate embodiment is not fully cylindrical.

The radiated-wave reflector of the alternate embodiment 220 spans, encircles, and/or surrounds the embodiment's central WEC 223 only between radial panels 224 and 236, inclusive of radial panels 230 and 235, thereby trapping any radiated waves emitted by the central WEC 223 in those radial and/or angular directions. Likewise, the angular and/or radial portion of the space around the central WEC 223 between radial panels 224 and 236, where the corresponding radial panels 131 and 134 of the embodiment 120 illustrated in FIGS. 5-12 are missing, is open to the body of water (e.g. 121 in FIG. 12) on which the embodiment floats. Any radiated waves emitted by the central WEC 220 in radial and/or angular directions outside, and/or exclusive of, the range of directions bounded by, and/or inclusive of, the partially-circumferential radiated-wave reflector 222, will tend to radiate away from the embodiment, carrying with them the energy invested by, and/or extracted from, the embodiment in their production.

Whereas, the embodiment 220 illustrated in FIG. 13 has a single radiated-wave reflector segment 222, and a single radial gap (between radial panels 224 and 236, the scope of the present disclosure includes, but is not limited to, embodiments which incorporate, include, and/or utilize, radiated-wave reflectors comprising any number of radial segments, and/or any number of radial gaps between radial segments, including those with radial segments of constant angular and/circumferential widths, as well as those with radial segments of inconstant and/or variable angular and/circumferential widths. The scope of the present disclosure is not limited to, and/or by, the number of radial segments, and/or radial gaps, nor the angular and/or circumferential widths, or, and/or associated with, an embodiment's radiated-wave reflector.

Figure 14:
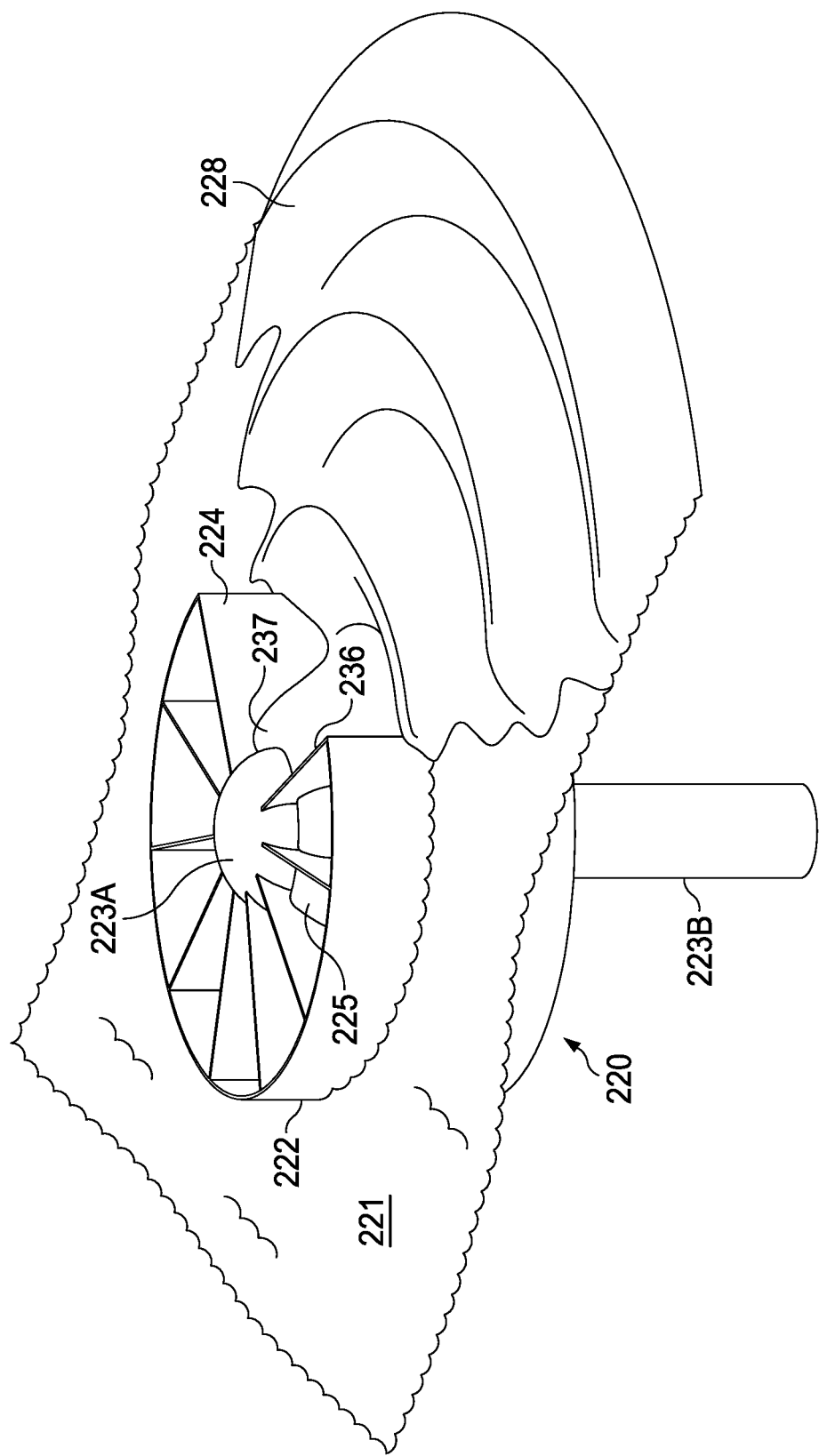
FIG. 14 is a perspective side view of the second embodiment.

FIG. 14 shows a perspective side view of the same embodiment 220 of the present disclosure that is illustrated in FIG. 13. As the embodiment bobs up and down in response to incident and/or environmental waves passing across the surface 221 of the body of water on which it floats, radiated waves 225 emitted by the central WEC 223A within the embodiment's reflector pool, i.e. within the portion of the embodiment bounded by the radiated-wave reflector 222 and radial panels 224 and 236, will tend to be trapped within the respective pie-slice-shaped portions of the enclosed annular space between the central WEC 223 and the radiated-wave reflector creating waves, e.g. 225.

And, as the embodiment bobs up and down in response to incident and/or environmental waves passing across the surface 221 of the body of water on which it floats, radiated waves 237 emitted by the central WEC 223A in a direction toward the missing portion (between radial panels 224 and 236) of the radiated-wave reflector 222 will tend to flow 228 away from the embodiment 220 without restriction or limitation.

The circumferentially-incomplete and/or partial radiated-wave reflector 222 of the embodiment 220 illustrated in FIGS. 13 and 14 is approximately cylindrical (though possessing a vertical slit and/or gap). However, the scope of the present disclosure includes, but is not limited to, similar embodiments which incorporate, include, and/or utilize, partially-circumferential, and/or circumferentially-incomplete, radiated-wave reflectors of any shape, including, but not limited to, radiated-wave reflectors that have cross-sectional shapes that are: elliptical, parabolic, and hyperbolic.

Figure 15:
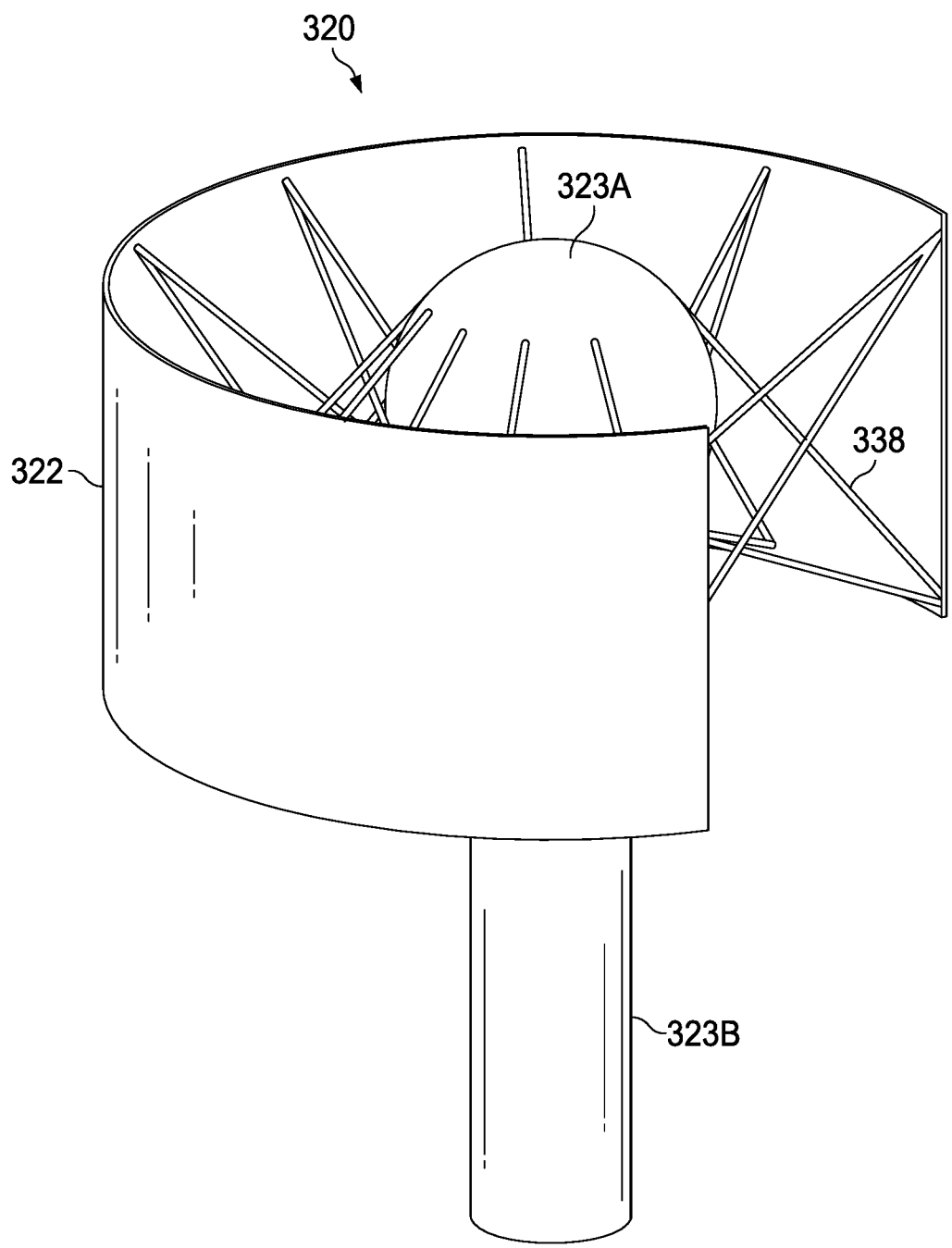
FIG. 15 is a perspective side view of a third embodiment of the present invention.

FIG. 15 shows a perspective side view of an alternate configuration 320 of the embodiment (220 in FIGS. 13 and 14) of the present disclosure that is illustrated in FIGS. 13 and 14. Similar to the embodiment 220 illustrated in FIGS. 13 and 14, the alternate embodiment 320 illustrated in FIG. 15 comprises a central WEC 323 and a partial, open, and/or circumferentially-incomplete, radiated-wave reflector 322. Unlike the embodiment 220 illustrated in FIGS. 13 and 14, and unlike the embodiment 120 illustrated in FIGS. 5-12, the alternate embodiment 320 illustrated in FIG. 15 utilizes suspension cables, stringers, and/or struts, e.g. 338, which maintain the relative position and orientation of the embodiment's radiated-wave reflector relative to its central WEC 323. And, unlike the radial panels of the prior illustrated embodiments, the cables and/or struts of the embodiment illustrated in FIG. 15 do not obstruct a lateral and/or circumferential flow of water within the portion of the annular gap created between the partial radiated-wave reflector and the central WEC, i.e. within the embodiment's reflector pool.

The scope of the present disclosure includes, but is not limited to, embodiments which incorporate, utilize, and/or include, radiated-wave reflectors that are connected, fastened, linked, secured, and/or attached, to a respective central WEC by connectors including, but not limited to, those comprising, fashioned of, including, and/or containing: radial walls, sheets, panels, and/or dividers, struts, chains, linkages, cables, ropes, tubes, pipes, and/or bars.

Figure 16:
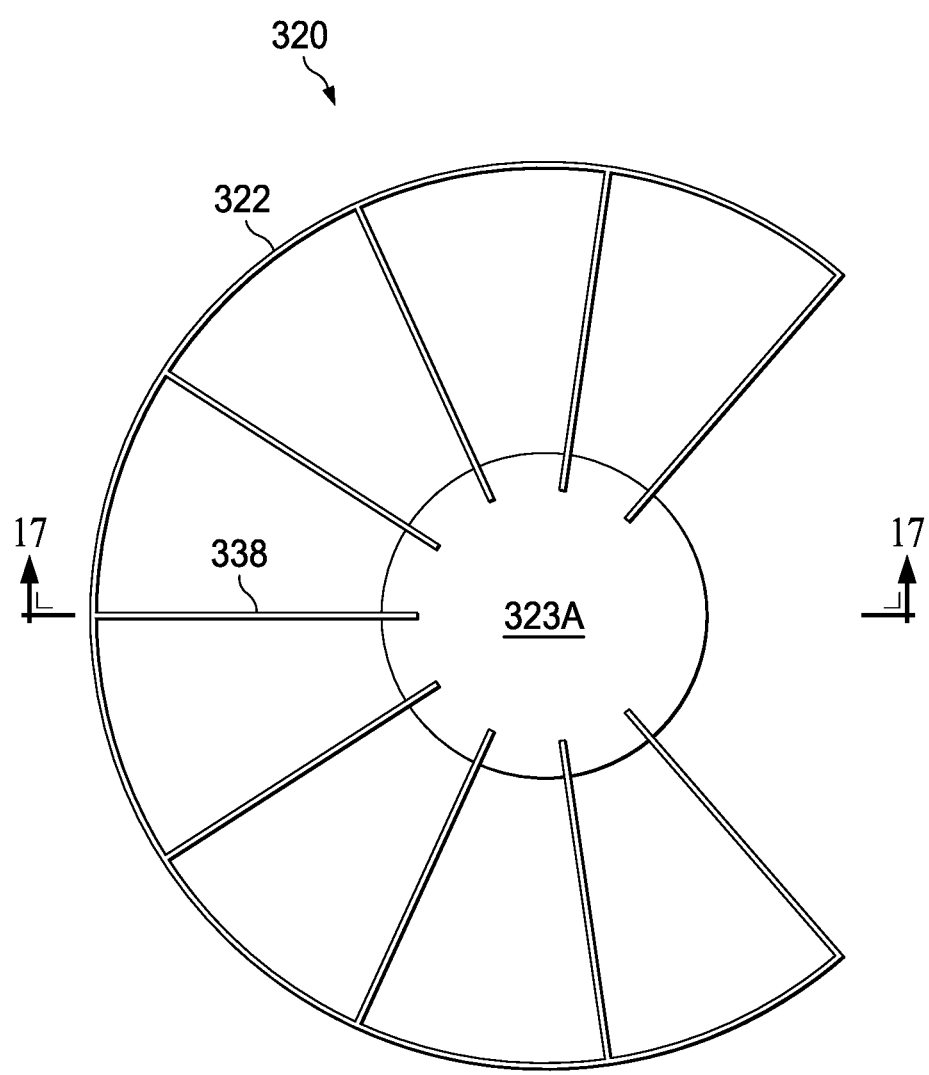
FIG. 16 is a top-down view of the third embodiment.

FIG. 16 shows a top-down view of the embodiment 320 of the present disclosure that is illustrated in FIG. 15.

Figure 17:
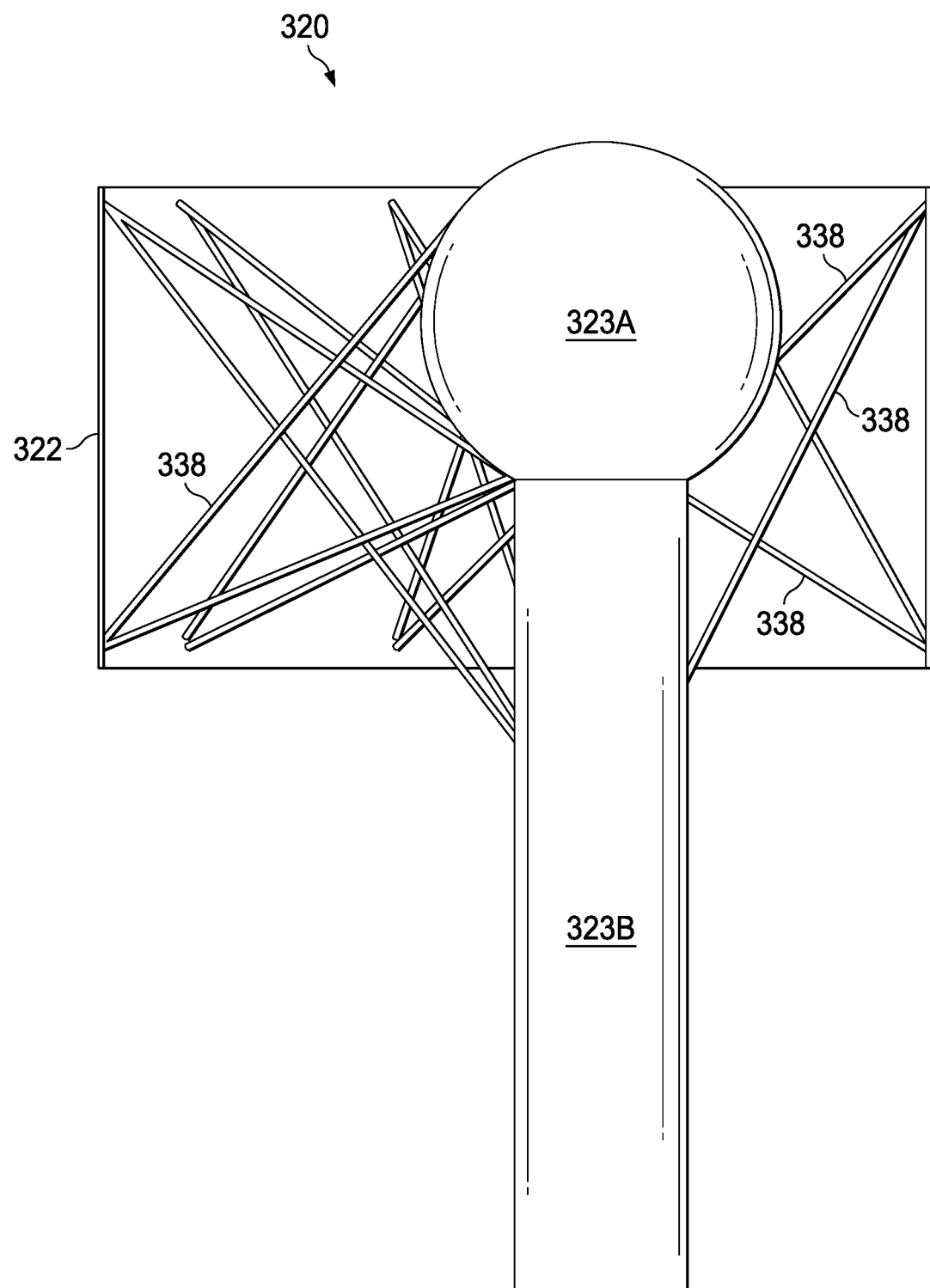
FIG. 17 is a side sectional view of the third embodiment.

FIG. 17 shows a side sectional view of the same embodiment 320 of the present disclosure that is illustrated in FIGS. 15 and 16 with the section plane being taken along line 17-17 of FIG. 16. A plurality of cables and/or struts 338 secure the partially-circumferential radiated-wave reflector 322 to the central WEC 323.

The scope of the present disclosure includes, but is not limited to, embodiments which connect their respective central WEC (and/or vessels) to and/or with their respective radiated-wave reflectors with tightly-tensioned cables, linkages, chains, stringers, and/or ropes; with loosely-tensioned, loose, and/or slack, cables, linkages, chains, stringers, and/or ropes; and/or with struts, beams, pipes, tubes, and/or other rigid connectors. The scope of the present disclosure is not limited to, and/or by, the means, methods, mechanisms, components, materials, and/or type of connectors, by and/or through which an embodiment's radiated-wave reflector is connected, fastened, attached, and/or secured, to its central WEC or other vessel.

An embodiment of the present disclosure similar to the ones illustrated in FIGS. 5-17 incorporates, includes, and/or utilizes, an upper approximately horizontal reflector plate and/or other approximately horizontal and approximately flat structural member, to connect, at least in part, its radiated-wave reflector to its central WEC (or vessel). This plate also tends to enclose the upper part of the radiated-wave reflector, and the reflector pool therein, thereby preventing, limiting, and/or inhibiting, fluid communication between the interior of the radiated-wave reflector and the atmosphere outside the embodiment. The upper reflector plate extends and connects to an uppermost edge and/or portion of the respective radiated-wave reflector, as well as connecting to an uppermost part, portion, or surface of the respective central WEC (or vessel).

A similar embodiment of the present disclosure which also incorporates, includes, and/or utilizes, an upper reflector plate incorporates, includes, and/or utilizes, within that plate a plurality of apertures, each of which may be opened or closed via a respective valve controlled by an embodiment control system and/or module. Another similar embodiment of the present disclosure which similarly incorporates, includes, and/or utilizes, an upper reflector plate incorporates, includes, and/or utilizes, within that plate a plurality of apertures, each of which directs a flow of air into, and out from, the interior of the upwardly enclosed radiated-wave reflector through a respective air turbine, each of which is operatively connected to a generator and each generator of which generates electrical power when its operatively connected air turbine is caused to rotate in response to a passage and/or flow of air therethrough.

The scope of the present disclosure includes, but is not limited to, embodiments which connect their respective WEC (and/or vessels) to and/or with their respective radiated-wave reflectors with tightly-tensioned cables, linkages, chains, stringers, and/or ropes; with loosely-tensioned, loose, and/or slack, cables, linkages, chains, stringers, and/or ropes; and/or with struts, beams, pipes, tubes, and/or other rigid connectors. The scope of the present disclosure is not limited to, and/or by, the means, methods, mechanisms, components, materials, and/or type of connectors, by and/or through which an embodiment's radiated-wave reflector is connected, fastened, attached, and/or secured, to its central WEC or other vessel.

An embodiment of the present disclosure similar to the ones illustrated in FIGS. 5-17 incorporates, includes, and/or utilizes, a free-floating WEC (or vessel) that is not directly affixed or connected to its respective radiated-wave reflector. One such embodiment incorporates, includes, and/or utilizes, elastic bumpers arrayed about and affixed to interior surfaces of its respective radiated-wave reflector, the bumpers which tend to prevent the respective free-floating WEC (or vessel) from directly colliding with the respective radiated-wave reflector, while not directly inhibiting the motion and/or movement of the WEC (or vessel) within the respective radiated-wave reflector. Another such embodiment incorporates, includes, and/or utilizes, an array of cables, ropes, chains, linkages, and/or struts, each of which tends to deflect, resist, and/or stop, the embodiment's respective free-floating WEC (or vessel) when that WEC moves to close to the embodiment's respective radiated-wave reflector.

An embodiment of the present disclosure is comprised exclusively of a buoyant radiated-wave reflector which tends to float adjacent to an upper surface of a body of water over which waves pass. When operated without a floating vessel or other buoyant object positioned within that portion of the surface of the body of water partially entrained, and/or at least partially surrounded, by the radiated-wave reflector, there is no direct source of radiated waves which the radiated-wave reflector may reflect. However, when, for instance, a mobile water craft, e.g. an unmanned submersible vehicle (USV), perhaps after inflating a bulbous element, component, and/or part, enters the embodiment's reflector pool (i.e. the portion of the body of water on which the embodiment floats that is partially enclosed and/or surrounded by the embodiment's radiated-wave reflector) then the bobbing of the mobile water craft in response to waves passing by and beneath the embodiment will tend to cause the mobile water craft to produce radiated waves which will then tend to emanate towards, and be reflected by, the, at least partially surrounding, radiated-wave reflector.

If such a mobile water craft that entered into the embodiment's reflector pool were a wave energy converter, or was configured and/or configurable to extract energy from wave-induced oscillations perhaps through its incorporation, utilization, and/or inclusion of a WEC module, then such a wave energy converter (module) might, of necessity, be relatively small. And, such a relatively small wave energy converter might be most sensitive and responsive to waves of a relatively short wavelength and/or high frequency, and/or such a relatively small wave energy converter might only be sensitive to wave motion having a relatively shallow wave base. Such a mobile water craft might therefore be unable to capture any significant energy from ambient incident and/or environmental waves within its deployment arena and/or area. However, such a mobile water craft might be able to capture an appreciable, usable, and/or significant, amount of energy from the radiated waves that its presence within an embodiment's reflector pool would tend to create, e.g. after its inflation of a radiated-wave creating bulbous component, and which the embodiment's radiated-wave reflector would tend to capture, reflect, amplify, and accumulate.

Thus, an embodiment of the present disclosure when adapted to host, and/or accommodate, the optional, temporary, and/or ad hoc, presence of a free-floating self-propelled water craft, might enable such a water craft to obtain energy from the very radiated waves that would tend to emanate from it in response to the movements imparted to it by larger ambient incident and/or environmental waves from which it would otherwise be unable to extract energy.

A similar water-craft energizing embodiment might incorporate a radial gap within its radiated-wave reflector (such as those characteristic of and by the embodiments illustrated in FIGS. 13-17) in order to facilitate the entry of autonomous surface vessels (ASVs) the wave energy extraction mechanisms of which might likewise benefit from the serially reflecting radiated waves it would give rise to within the embodiment's radiated-wave reflector.

In the absence of a surrounding (or partially surrounding) radiated-wave reflector of an embodiment of the present disclosure, a water craft could rarely, if ever, obtain energy from the very radiated waves which its ambient-wave-induced bobbing would tend to give rise to. Thus, the invention herein disclosed satisfies an unmet need of various water craft, especially those too small to reasonably extract meaningful amounts of energy from the kinds and sizes of waves typically found in the ocean.

Figure 18:
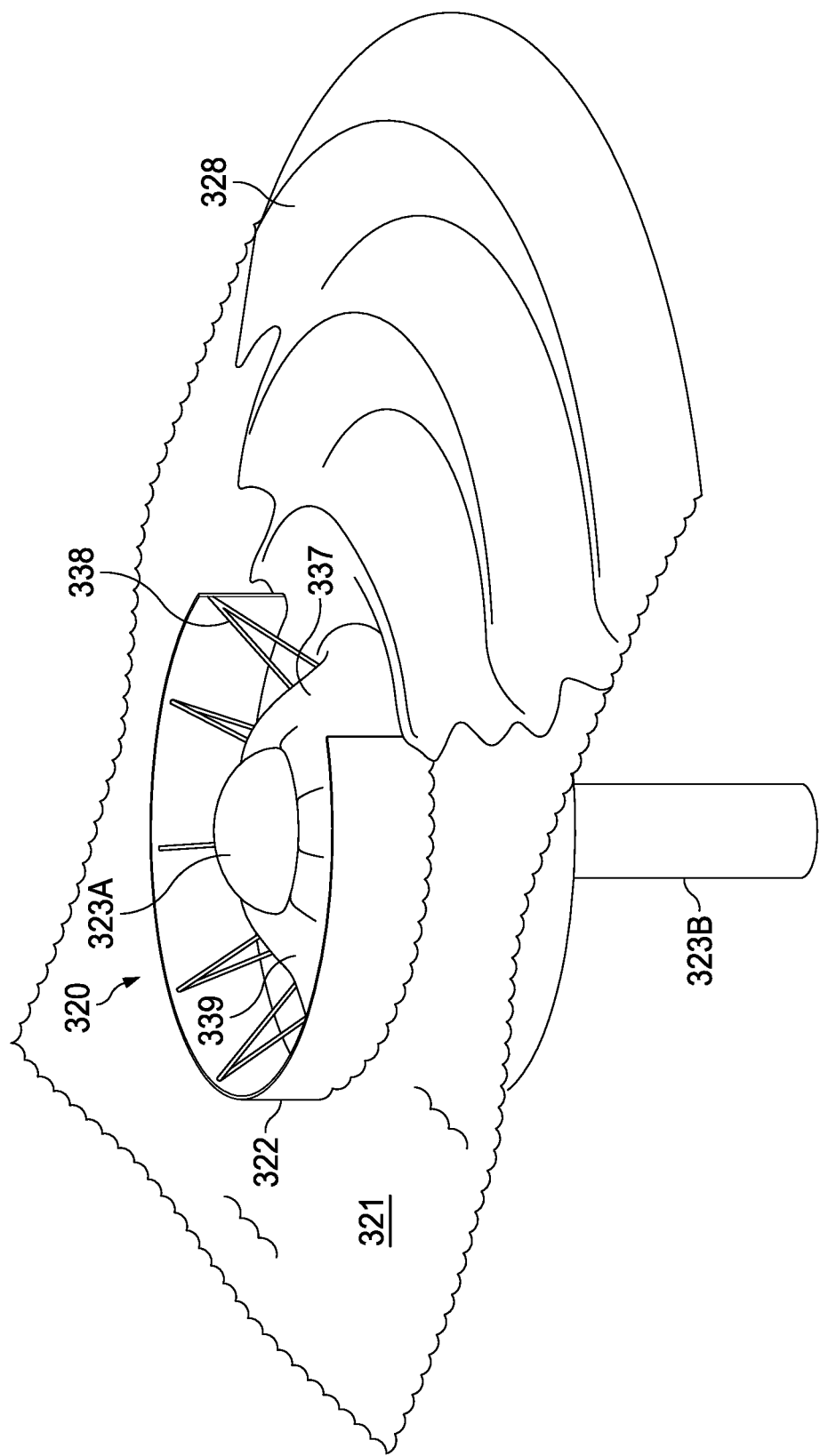
FIG. 18 is a perspective side view of the third embodiment.

FIG. 18 shows a perspective side view of the embodiment 320 of the present disclosure that is illustrated in FIGS. 15-17. As the embodiment bobs up and down in response to waves passing across the surface 321 of the body of water on which it floats, radiated waves 339 emitted within the portion of the embodiment radially bounded by the partially-circumferential radiated-wave reflector 322 will tend to be reflected back toward the central WEC 323 by the radiated-wave reflector.

And, as the embodiment 320 bobs up and down in response to incident and/or environmental waves passing across the surface 321 of the body of water on which it floats, radiated waves 337 emitted in a direction toward the missing portion of the radiated-wave reflector 322 will tend to flow 328 away from the embodiment 320 without restriction or limitation.

The absence of radial panels within and/or dividing the annular gap between the radiated-wave reflector 322 and the central WEC 323 means that in addition to water flowing radially back and forth between the radiated-wave reflector and the central WEC, water may also flow circumferentially within the annular gap and/or reflective pool.

The circumferentially-incomplete and/or partial radiated-wave reflector 322 of the embodiment 320 illustrated in FIGS. 15-18 is approximately cylindrical (though possessing a vertical slit and/or gap). However, the scope of the present disclosure includes, but is not limited to, similar embodiments which incorporate, include, and/or utilize, partially-circumferential, and/or circumferentially-incomplete, radiated-wave reflectors of any shape, including, but not limited to, radiated-wave reflectors that have cross-sectional shapes that are: elliptical, parabolic, and hyperbolic.

Figure 19:
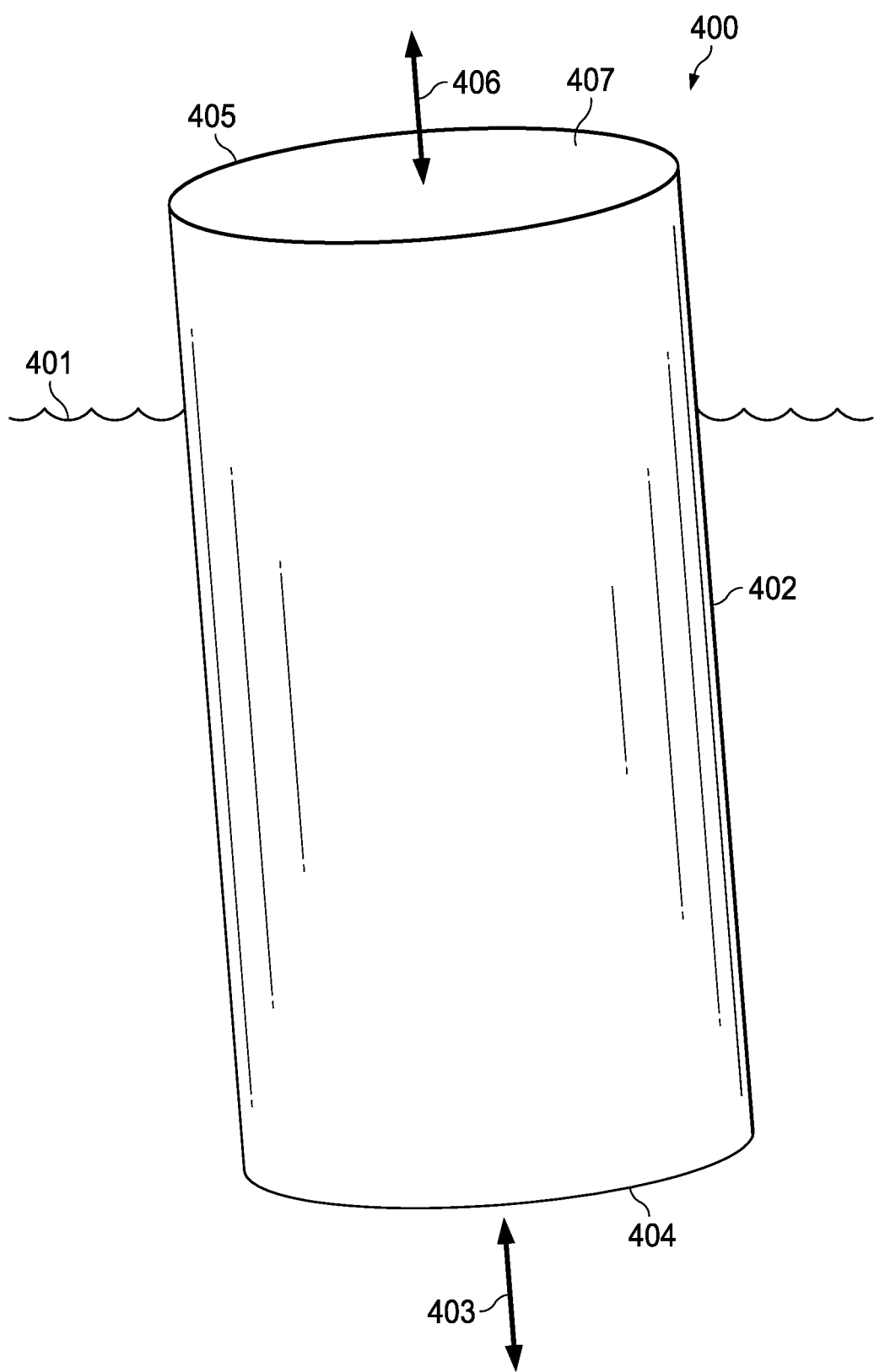
FIG. 19 is a perspective side view of a fourth embodiment.

FIG. 19 shows a perspective side view of an embodiment 400 of the present disclosure. The embodiment is buoyant and floats at and/or adjacent to an upper surface 401 of a body of water over which waves pass. The embodiment has an approximately cylindrical exterior wall 402 or hull which surrounds a hollow interior tubular channel, having upper 405 and lower mouths 404. Water may flow 403 into the interior of the interior channel, and water may flow 403 out of the interior channel, through a lower mouth 404. An upper mouth 405 of the tubular channel likewise permits atmospheric air to flow 406 into, and out from, the interior tubular channel of the embodiment. Adjacent to an upper end of the embodiment is a convex, curved, toroidal, and/or bulbous annular radiated-wave-generation chamber 407 which provides flotation and buoyancy to the embodiment, and which, in response to movements of the embodiment, and/or alterations of the embodiment's draft, waterplane area, and/or displacement, such as those caused by passing incident and/or environmental waves, produces radiated waves which tend to resonate within, and/or adjacent to a surface of, water partially enclosed within the interior of the embodiment.

Figure 20:
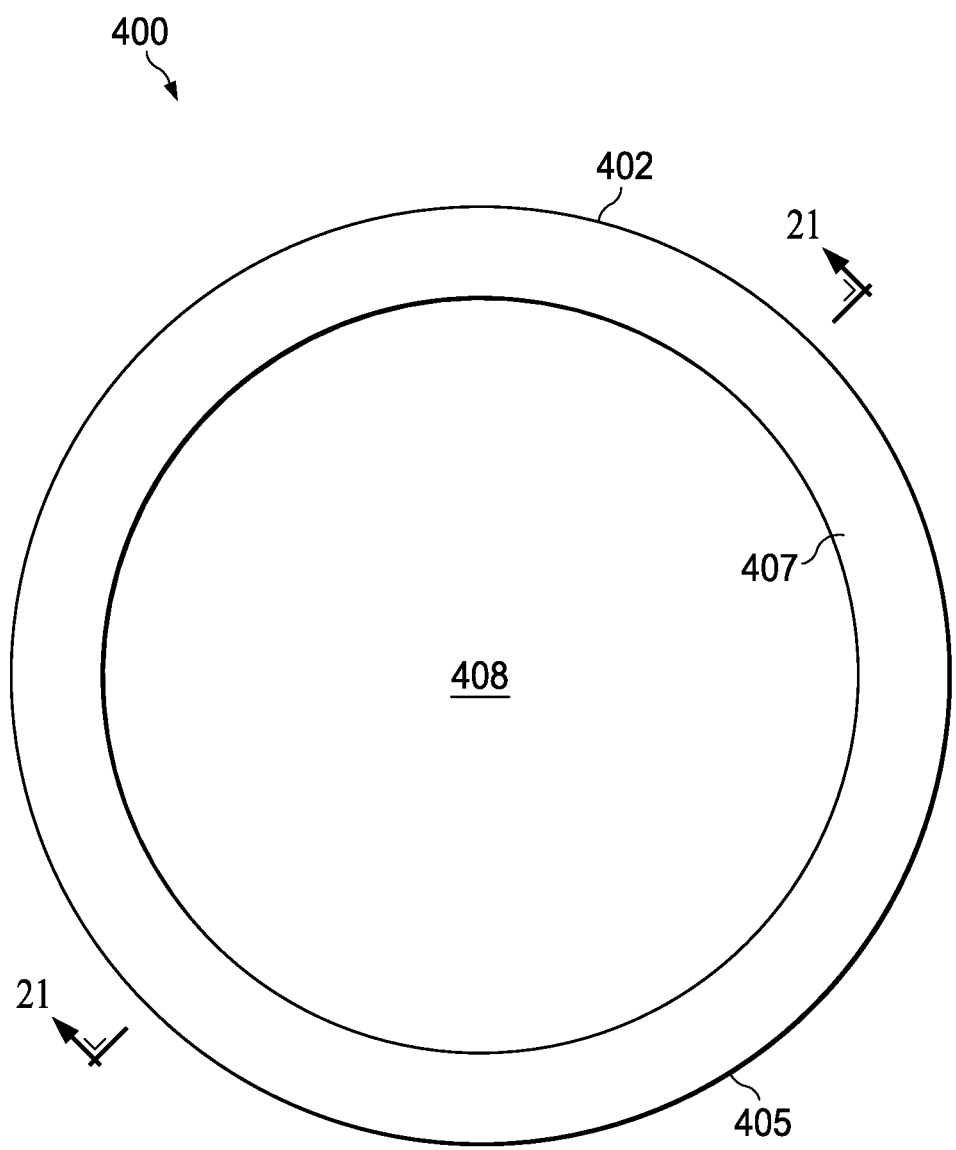
FIG. 20 is a top-down view of the fourth embodiment.

FIG. 20 shows a top-down view of the same embodiment 400 of the present disclosure that is illustrated in FIG. 19. The embodiment's convex, curved, and/or bulbous annular radiated-wave-generation chamber 407 is attached to, and/or extrudes from, an upper portion of the inner surface and/or wall of the embodiment's outer hull 402. Water from the body of water (401 of FIG. 19) upon which the embodiment floats, as well as air from the atmosphere above the body of water upon which the embodiment floats, are able to flow freely into and out of the nominally vertical inner tubular channel 408, through upper and lower ends of the tubular channel, the channel being defined and/or surrounded by the embodiment's approximately cylindrical outer hull 402.

Figure 21:
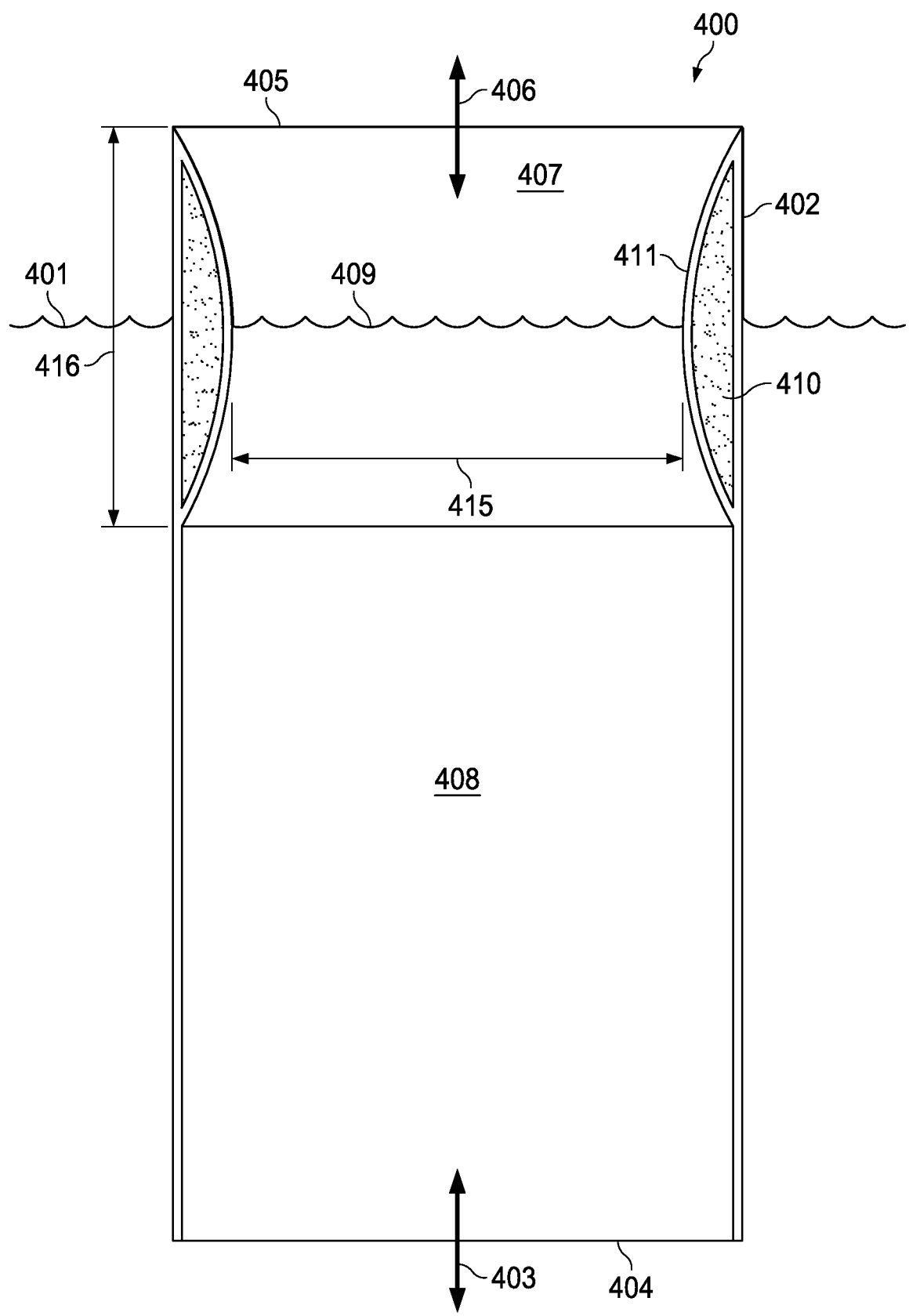
FIG. 21 is a side sectional view of the fourth embodiment.

FIG. 21 shows a side sectional view of the same embodiment 400 of the present disclosure that is illustrated in FIGS. 19 and 20 with the section plane being taken along line 21-21 of FIG. 20.

Water 403 and air 406 may flow into and out of the embodiment's nominally vertical inner tubular channel 408. At rest, water laterally and/or partially enclosed within the inner tubular channel has an upper surface 409 that is approximately coplanar with an upper surface 401 of the body of water upon which the embodiment floats.

At an upper end of the embodiment is a convex, curved, and/or bulbous annular radiated-wave-generation chamber 407 which has a diameter 415, at its narrowest and/or most constricted point and/or horizontal cross-section. With respect to the embodiment illustrated in FIG. 21, the radiated-wave-generation chamber has an interior 410 filled with polyurethane foam. The interior of the convex annular radiated-wave-generation chamber is defined and/or created by a curved, convex, and/or bulbous inner-channel wall 411 and a portion of the outer cylindrical wall 402 of the embodiment.

The scope of the present disclosure includes, but is not limited to, embodiments which incorporate, include, and/or utilize, radiated-wave-generation chambers that are hollow and filled with a buoyant material. The scope of the present disclosure includes, but is not limited to, embodiments which incorporate, include, and/or utilize, radiated-wave-generation chambers that are solid and comprised of buoyant materials, including, but not limited to: plastic, wood, polyvinyl chloride, Styrofoam, and/or structural polyurethane foam. The scope of the present disclosure includes, but is not limited to, embodiments which incorporate, include, and/or utilize, radiated-wave-generation chambers that are hollow and filled with gaseous and/or liquid materials including, but not limited to: air, nitrogen, helium, carbon dioxide, polyurethane foam, and/or oil.

The scope of the present disclosure is not limited to, and/or by, the materials and/or combination of materials, rigid, flexible, liquid, and/or gaseous of which the radiated-wave-generation chamber is comprised, and/or with which the radiated-wave-generation chamber is filled.

The scope of the present disclosure includes, but is not limited to, similar embodiments which incorporate, include, and/or utilize, radiated-wave-generation chambers that have and/or include a variety of vertical cross-sectional shapes, curves, geometries, and/or features, including, but not limited to segments that are approximately circular (as 411 in FIG. 21), elliptical, parabolic, frustoconical, and/or hyperbolic.

The radiated-wave reflector 402 of the embodiment 400 illustrated in FIGS. 19-21 is approximately cylindrical. However, the scope of the present disclosure includes, but is not limited to, similar embodiments which incorporate, include, and/or utilize, radiated-wave reflectors of any shape, including, but not limited to, radiated-wave reflectors that have cross-sectional shapes that are: elliptical, parabolic, and hyperbolic.

The scope of the present disclosure includes, but is not limited to, embodiments which incorporate, include, and/or utilize, fully enclosed and/or sealed radiated-wave-generation chambers such as the radiated-wave-generation chamber illustrated in FIGS. 19-21, as well as those which incorporate, include, and/or utilize, radiated-wave-generation chambers that are not fully sealed, and those which incorporate, include, and/or utilize, curved surfaces in place of, or in addition to, a radiated-wave-generation chamber.

The scope of the present disclosure includes, but is not limited to, any particular design, style, variety, and/or type of radiated-wave-generation chamber, but instead includes and extends to embodiments possessing, incorporating, including, and/or utilizing, any type, design, variety, and/or style, of fluid-moving surface, feature, component and/or part which achieves the operational objective of producing radiated waves in response to movements, especially in response to vertical movements, of the embodiment relative to an upper surface of the body of water on which they float.

The scope of the present disclosure is not limited to, and/or by, the cross-sectional shape of the radiated-wave-generation chamber. And, while the embodiment illustrated in FIGS. 19-21 include a single radiated-wave-generation chamber and/or surface, the scope of the present disclosure includes embodiments possessing, incorporating, including, and/or utilizing, two or more radiated-wave-generation chambers and/or surfaces.

Figure 22:
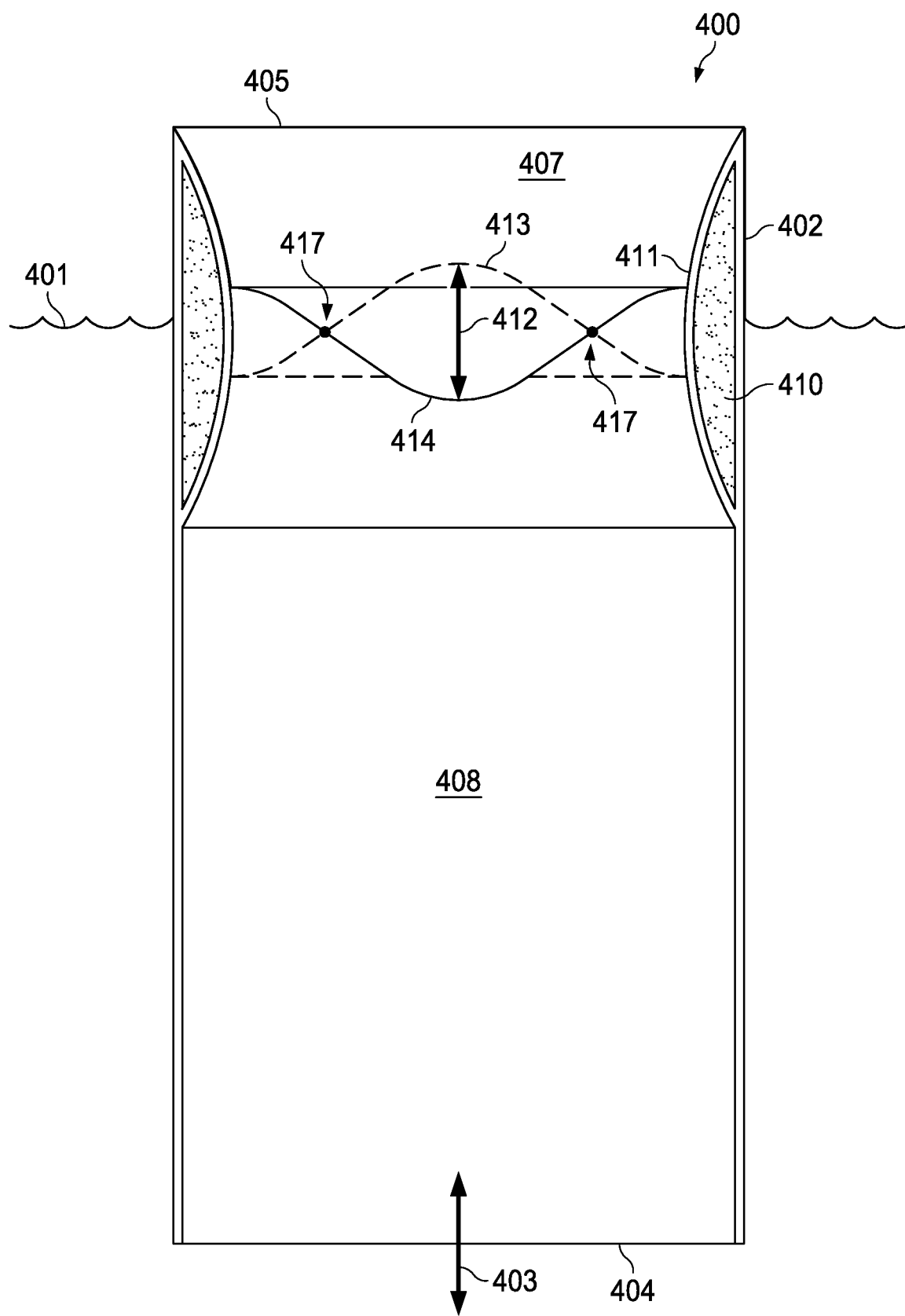
FIG. 22 is another side sectional view of the fourth embodiment.

FIG. 22 shows the same side sectional view of the same embodiment 400 of the present disclosure that is illustrated in FIGS. 19 and 21 with the section plane being taken along line 21-21 of FIG. 20. However, whereas the side sectional view of FIG. 21 shows a relatively calm upper surface (409 in FIG. 21) of the water partially enclosed within the embodiment as might characterize the embodiment when the embodiment is floating at rest at the surface of a calm body of water, the side sectional view of FIG. 22 shows an upper surface of the water partially enclosed within the embodiment manifesting an oscillating wave, similar to a resonant and/or standing wave, as might occur in response to a vertical movement of the embodiment, e.g. with respect to a surface 401 of the body of water on which the embodiment floats, in response to a passing incident and/or environmental wave.

When a passing wave, and/or an unbalanced excess of gravitational potential energy and/or weight, causes the embodiment to experience a downward acceleration and to thereby be moved downward with respect to the surface 401 of the body of water on which the embodiment floats, two phenomena will tend to occur. First, the inner surface 411 of the embodiment's radiated-wave-generation chamber 407 will tend to move downward with respect to the surface of the water within the embodiment's inner tubular channel 408, the average level (409 in FIG. 21) of which is nominally in equilibrium with the level 401 of the water outside the embodiment's outer hull, or radiated-wave reflector 402, thereby radiating a wave crest from the periphery of the radiated-wave-generation chamber toward the center of the embodiment's inner tubular channel, and/or toward the opposing side of that tubular channel. And, second, the increase in the embodiment's draft will tend to increase the buoyant force acting on the embodiment, and counteract the embodiment's gravitational potential energy and/or weight, which will tend to compensate for the unbalanced excess of gravitational potential energy and/or weight, and will then tend to result in a surplus of upward buoyant force acting upon the embodiment.

By contrast, when a passing wave, and/or an unbalanced excess of buoyant potential energy, causes the embodiment to experience an upward acceleration and to thereby to be moved upward with respect to the surface 401 of the body of water on which the embodiment floats, two complementary phenomena will tend to occur. First, the inner surface 411 of the embodiment's radiated-wave-generation chamber 407 will tend to move upward with respect to the surface of the water within the embodiment's inner tubular channel 408, the average level (409 in FIG. 21) of which is nominally in equilibrium with the level 401 of the water outside the embodiment's outer hull, or radiated-wave reflector 402, thereby radiating a wave trough from the periphery of the radiated-wave-generation chamber toward the center of the embodiment's inner tubular channel, and/or toward the opposing side of that tubular channel. And, second, the decrease in the embodiment's draft will tend to decrease the buoyant force acting on the embodiment, and counteract the embodiment's gravitational potential energy and/or weight, which will tend to compensate for the unbalanced excess of buoyant potential energy, and will then tend to result in a surplus of downward gravitational force acting upon the embodiment.

A succession of wave crests and wave troughs radiated from and/or by the radiated-wave-generation chamber toward the center of the inner tubular channel will have a characteristic embodiment-specific frequency and wavelength which can (with respect to particular embodiment geometries, designs, and/or configurations) cause them to create a trapped and oscillating wave form similar to that of a standing wave 413-414 within an upper portion of the water within the inner tubular channel. And, because the embodiment's outer wall, hull, or radiated-wave reflector is cylindrical (and has vertically straight sides and approximately constant cross-sectional areas) the embodiment tends to generate little, if any, external radiated waves, and/or damping radiation.

Therefore, as a result of the embodiment's oscillatory exchange of upward buoyant forces and downward gravitational forces, the embodiment's lack of significant outward radiation of damping waves, and the complementary oscillatory radiated waves trapped within the embodiment's inner tubular channel, the embodiment tends to absorb energy from passing incident and/or environmental waves, convert a portion of the absorbed energy into an oscillatory pattern of embodiment bobbing, and a complementary oscillatory pattern of radiated waves within its inner tubular channel, and retain significant portions of that trapped energy for relatively long periods of time due to the embodiment's avoidance of significant damping losses. When coupled with an appropriate power take off mechanism and/or apparatus whose response and/or efficiency is optimized with respect to the embodiment's characteristic oscillatory motions, and/or the characteristic oscillatory radiated waves generated by the embodiment within the embodiment's inner tubular channel, the energy-capture efficiency of such an embodiment can be significantly greater than other wave energy capture devices of the prior art.

As circular radiated waves generated at the inner surface and/or wall 411 of the radiated-wave-generation chamber 407 radiate towards the center of the inner tubular channel 408, and then continue past the center and radiate toward the opposing side of that inner tubular channel, and are then reflected back and re-radiated towards the center of the inner tubular channel, and so on . . . the circular waves radiating toward the center, and those radiating away from the center, tend to interfere with one another and create a pattern of circular waves which can, depending on the embodiment design, be similar to a standing and/or resonant wave.

The interfering circular radiated waves produced by the radiated-wave-generation chamber 407 of the embodiment illustrated in FIG. 22 result in an oscillating wave similar to a standing and/or resonant wave 414, which oscillates about a circular node 417. Alternate patterns, behaviors, and/or amplitudes of device-specific characteristic patterns of oscillating waves may be manifested through the careful selection of various embodiment attributes such as: the shape, curvature, and/or design of the radiated-wave-generation chamber 407, especially with respect to a vertical cross-section of that radiated-wave-generation chamber; the degree and type of curvature of the innermost surface 411 of the radiated-wave-generation chamber; the cross-sectional shape of the radiated-wave-generation chamber; the height (416 of FIG. 21) of the radiated-wave-generation chamber; the nominal vertical position of the radiated-wave-generation chamber relative to the mean and/or resting surfaces of the body of water 401 on which the embodiment floats and/or the water (409 in FIG. 21) trapped within the inner tubular channel 408; the average density of the embodiment; and the draft and/or nominal depth of its cylindrical outer hull, or radiated-wave reflector 402. The scope of the present disclosure includes embodiments exhibiting any and all values of these attributes, any and all characteristic patterns of oscillating radiated waves within their respective inner tubular channels, as well as any and every combination of such attribute values and radiated wave patterns.

With respect to embodiments incorporating, utilizing, and/or including radiated-wave-generation chambers 407 having an approximately circular cross-sectional shape 411, such as the one illustrated in FIGS. 19-22, the radius of the curvature associated with that radiated-wave reflector may also influence the pattern, behavior, and/or amplitude of device-specific characteristic patterns of oscillating waves.

More energetic incident and/or environmental waves, and longer exposure of an embodiment to a specific type of incident and/or environmental wave, would be expected to cause an embodiment of the present disclosure to produce radiated waves of relatively greater amplitudes. However, a particular embodiment would be expected to produce radiated waves within its inner tubular channel having approximately the same, consistent, and/or constant frequency, wavelength and/or period.

While the embodiment illustrated in FIG. 22 is radially symmetrical, the scope of the present disclosure extends to, and includes, embodiments having non-symmetrical and/or asymmetrical geometries as well.

While the embodiment illustrated in FIG. 22 comprises, incorporates, utilizes, and/or includes, a radially-complete outer hull, or radiated-wave reflector 402 and radiated-wave-generation chamber 407, the scope of the present disclosure extends to, and includes, embodiments having radially incomplete radiated-wave reflectors and radiated-wave-generation chambers such that such embodiments might appear to have a vertical slit, gateway, and/or gap fluidly connecting all of a portion of the water (409 in FIG. 21) inside an embodiment's inner tubular channel with the body of water 401 on which the embodiment floats. Such a gap might permit and/or facilitate the entry and exit of one or more autonomous underwater and/or surface vessels into the inner tubular channel where their ability to harvest energy from wave motion may be improved.

Attributes of the radiated waves generated by an embodiment's radiated-wave-generation chamber 407, including, but not limited to, a wavelength, period, and frequency of those radiated waves, are a result of, are determined by, and/or may be affected by, the geometric properties of the embodiment, including, but not limited to: the degree and type of curvature of the innermost surface 411 of the radiated-wave-generation chamber, a vertical cross-sectional shape of the radiated-wave-generation chamber, a height (416 of FIG. 21) of the radiated-wave-generation chamber, a nominal vertical position of the radiated-wave-generation chamber relative to the embodiment's nominal waterline (when the embodiment is at rest at the surface of a waveless body of water), a diameter (415 of FIG. 21) of the narrowest circular cross-section of the embodiment's inner tubular channel 408, a displacement of the embodiment, and a buoyancy (i.e. the density) of the embodiment.

Attributes of the radiated waves generated by an embodiment's radiated-wave-generation chamber 407, including, but not limited to, an amplitude of those radiated waves, are a result of, are determined by, and/or may be affected by, a buoyant property of the embodiment, including, but not limited to: its displacement, the presence and/or mass of ballast (including water ballast), and its average density.

With respect to the embodiment illustrated in FIGS. 19-22, the height of the water within the embodiment's central inner tubular channel 408, and therefore the embodiment's "inner" draft with respect to that inner volume of water, act in concert with the "outer" draft of the embodiment with respect to the surface 401 of the body of water on which the embodiment floats, to manifest and/or create a net and/or effective degree of buoyancy and/or a net and/or effective upward buoyant force. Therefore, with respect to some embodiments of the present disclosure, such as the embodiment illustrated in FIGS. 19-22, i.e. with respect to some embodiments which characteristically manifest certain patterns of oscillating radiated waves within their inner tubular channels, as the water within the embodiment's central inner tubular channel rises and falls (e.g. through the production of an oscillating pattern of radiated waves similar to a standing wave) in response to a rising and falling of the embodiment with respect to the surface of the body of water on which the embodiment floats, so too these types of embodiments tend to rise and fall somewhat resonantly with the rising and falling of the water within their respective inner tubular channels.

Both the oscillatory rising and falling of the surface 413-414 of the water (409 in FIG. 21) within an embodiment's inner tubular channel 408, as well as the oscillatory rising and falling of the entire embodiment with respect to the surface (401 in FIG. 21) of the water on which the embodiment floats, can be used by a power take off apparatus and/or mechanism integrated within an embodiment to extract energy from waves passing across the surface of a body of water on which an embodiment floats. Furthermore, because the frequency of the radiated-wave oscillations 413-414 adjacent to the surface of the water within an embodiment's inner tubular channel 408, as well as the frequency of such radiated-wave oscillations, tend to be specific, repeatable, and predictable (i.e. they are approximately equal to a resonant frequency of the embodiment), any power take off apparatus and/or mechanism integrated within an embodiment is best designed, configured, and/or tuned to extract energy with optimal and/or maximal efficiency through a designing, configuring, and/or tuning of such a power take off apparatus and/or mechanism to achieve optimal energy extraction at the resonant frequency of its respective embodiment when that embodiment is perturbed, excited, and/or vertically moved at the surface of a body of water. Thus, an embodiment of the present disclosure can be excited and/or moved by incident and/or environmental waves of a relatively great range and/or variety of frequencies, while the power take off of an embodiment can enjoy, and/or benefit from, the operational and cost efficiencies of energy extraction at a single frequency.

Figure 23:
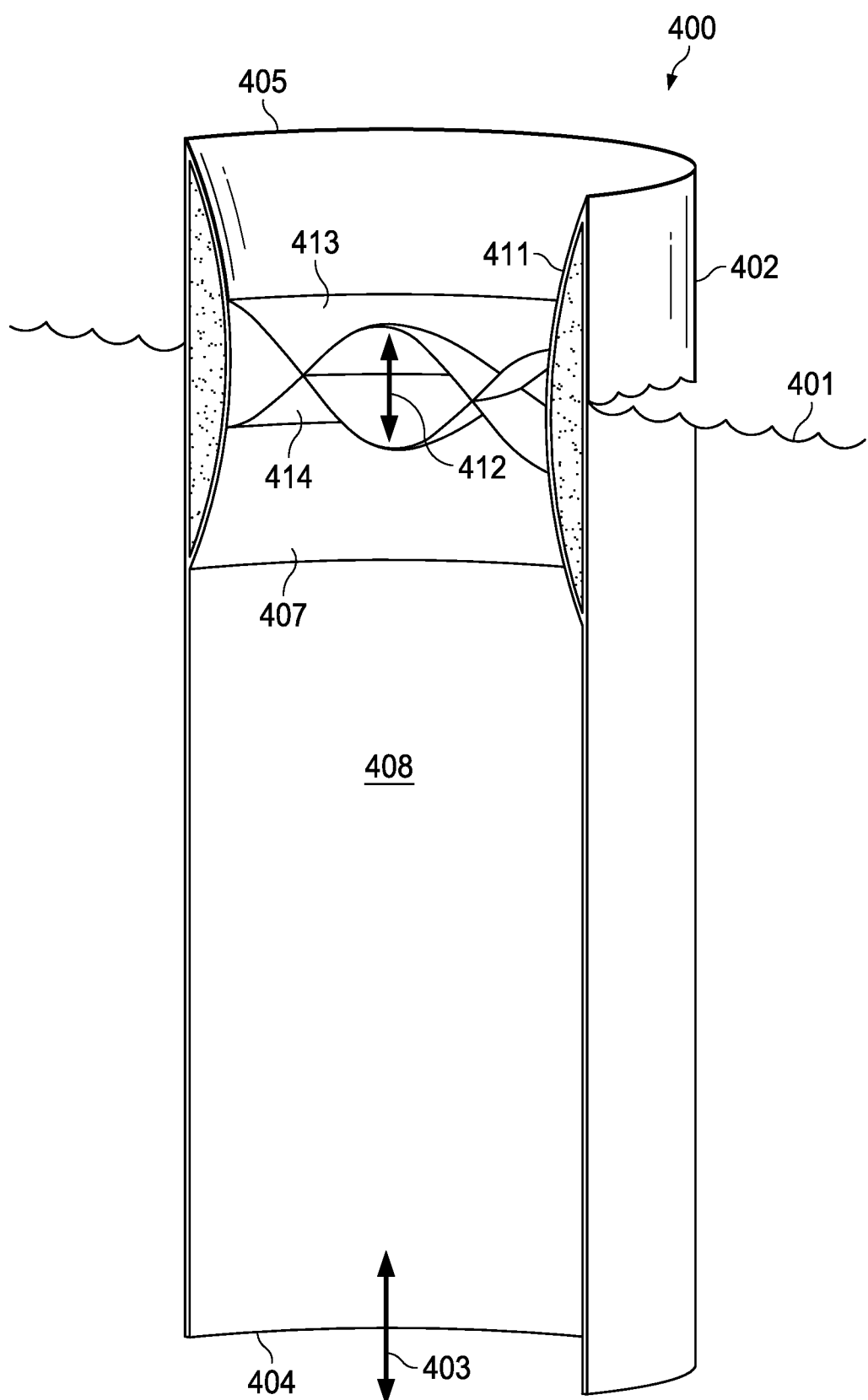
FIG. 23 is a perspective side sectional view of the fourth embodiment.

FIG. 23 shows a perspective view of the same side sectional view of the embodiment illustrated in FIG. 22. As with FIG. 22, the section plane is taken along line 21-21 of FIG. 20.

The illustration in FIG. 23 shows a superposition of different phases of an oscillatory wave, similar to a resonant wave, induced, created, and/or radiated, within an upper portion of the embodiment's inner tubular channel 408 in response to a vertical movement of the embodiment relative to the surface 401 of the body of water on which the embodiment floats and/or the surface (409 in FIG. 21).

The scope of the present disclosure includes, but is not limited to, embodiments which are designed, configured, fabricated, and/or built, so as to manifest oscillatory waves, similar to standing and/or resonant waves, at the surfaces of the water within their respective inner tubular channels that have any wavelength, period, and/or pattern, e.g. radial pattern with respect to the surface of the respective inner tubular channel. The scope of the present disclosure also includes, but is not limited to, embodiments which are designed, configured, fabricated, and/or built, so as to manifest oscillatory waves which are similar to standing waves, as well as embodiments which are designed, configured, fabricated, and/or built, so as to manifest oscillatory waves which are not similar to standing waves.

Figure 24:
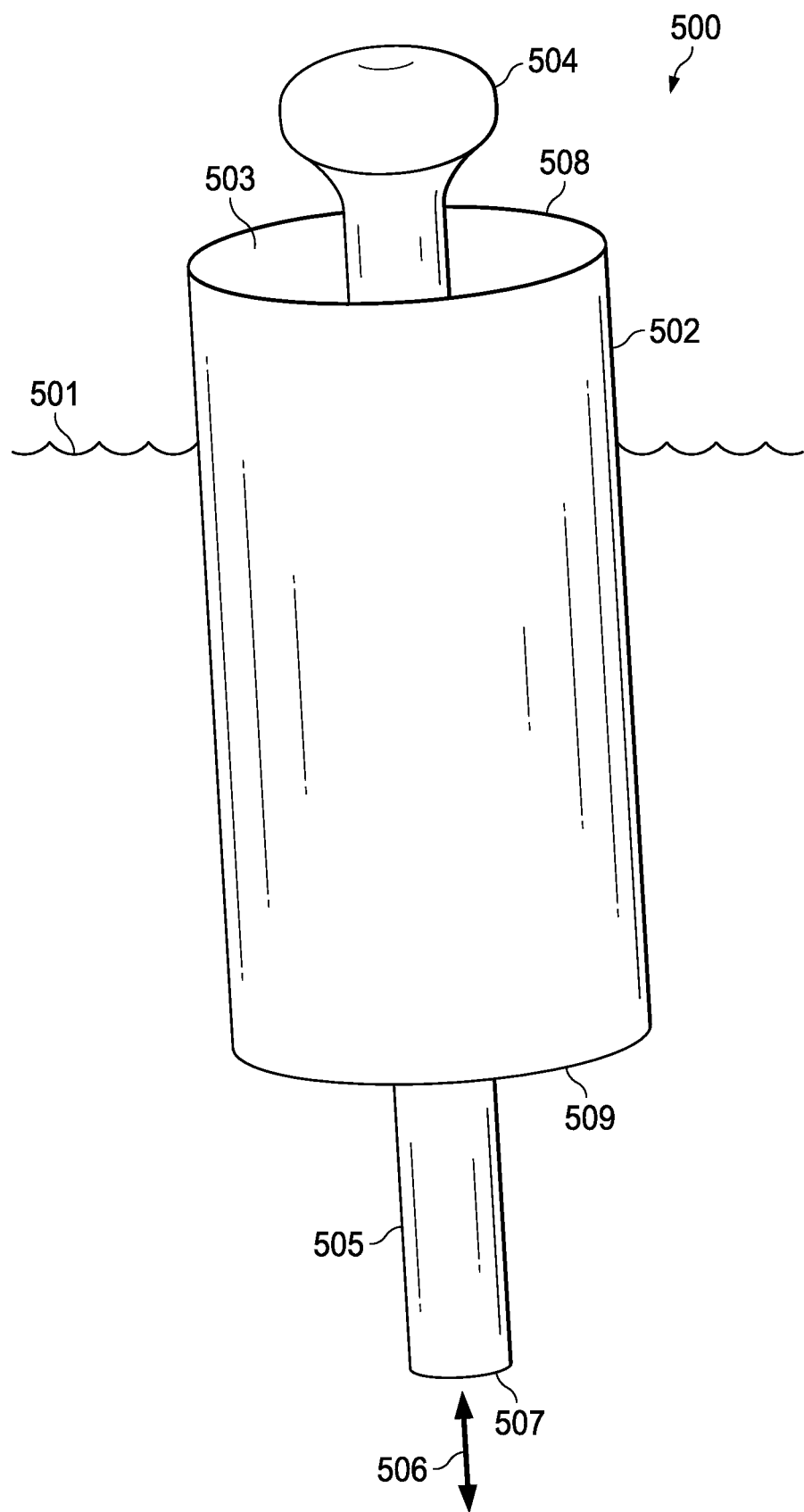
FIG. 24 is a perspective side view of a fifth embodiment.

FIG. 24 shows a perspective side view of an embodiment 500 of the current disclosure.

The embodiment illustrated in FIG. 24 is buoyant and floats adjacent to an upper surface 501 of a body of water over which waves pass. The embodiment illustrated in FIG. 24 is similar to the embodiment illustrated in FIGS. 19-23. Like the embodiment illustrated in FIGS. 19-23, the embodiment illustrated in FIG. 24 comprises, incorporates, utilizes, and/or includes, an approximately cylindrical outer hull or radiated-wave reflector 502 (402 in FIG. 22), and a radiated-wave-generation chamber 503 (407 in FIG. 22). However, unlike the embodiment illustrated in FIGS. 19-23, the embodiment illustrated in FIG. 24 further comprises, incorporates, utilizes, and/or includes, a heave-energized power take off mechanism 504.

The power take off mechanism 504-505 is similar to, and incorporates design elements of, an embodiment of the inertial hydrodynamic wave engine disclosed in U.S. Pat. No. 11,118,559, and in particular, is a heave-energized and pressurized-air-driven embodiment of that technology, where a pressurized air pocket and water reservoir are contained, enclosed, and/or trapped, within an upper relatively small bulbous portion 504 of the power take off mechanism, and pressurized water is occasionally, regularly, and/or periodically, injected, added, and/or introduced, to that pressurized water reservoir from, and/or by, a constricted tube 505 in response to heaving motions of the power take off mechanism.

In response to wave action at the embodiment, water enters and leaves 506 a lower portion of the constricted tube 505 through a lower mouth 507 or aperture. Water introduced to, and trapped within, the water reservoir within the upper bulbous portion 504 flows out through a water turbine and generator (not visible), thereby generating electrical power.

The power take off mechanism 504-505 is designed to operate at a maximum efficiency when moved at the resonant frequency of the embodiment, and/or at the dominant frequency expected of radiated waves generated by the embodiment's radiated-wave-generation chamber 503.

The embodiment's outer hull or radiated-wave reflector 502 contains upper 508 and lower 509 mouths and/or apertures through which water and/or air may freely flow into and out of a central channel within the radiated-wave reflector.

Figure 25:
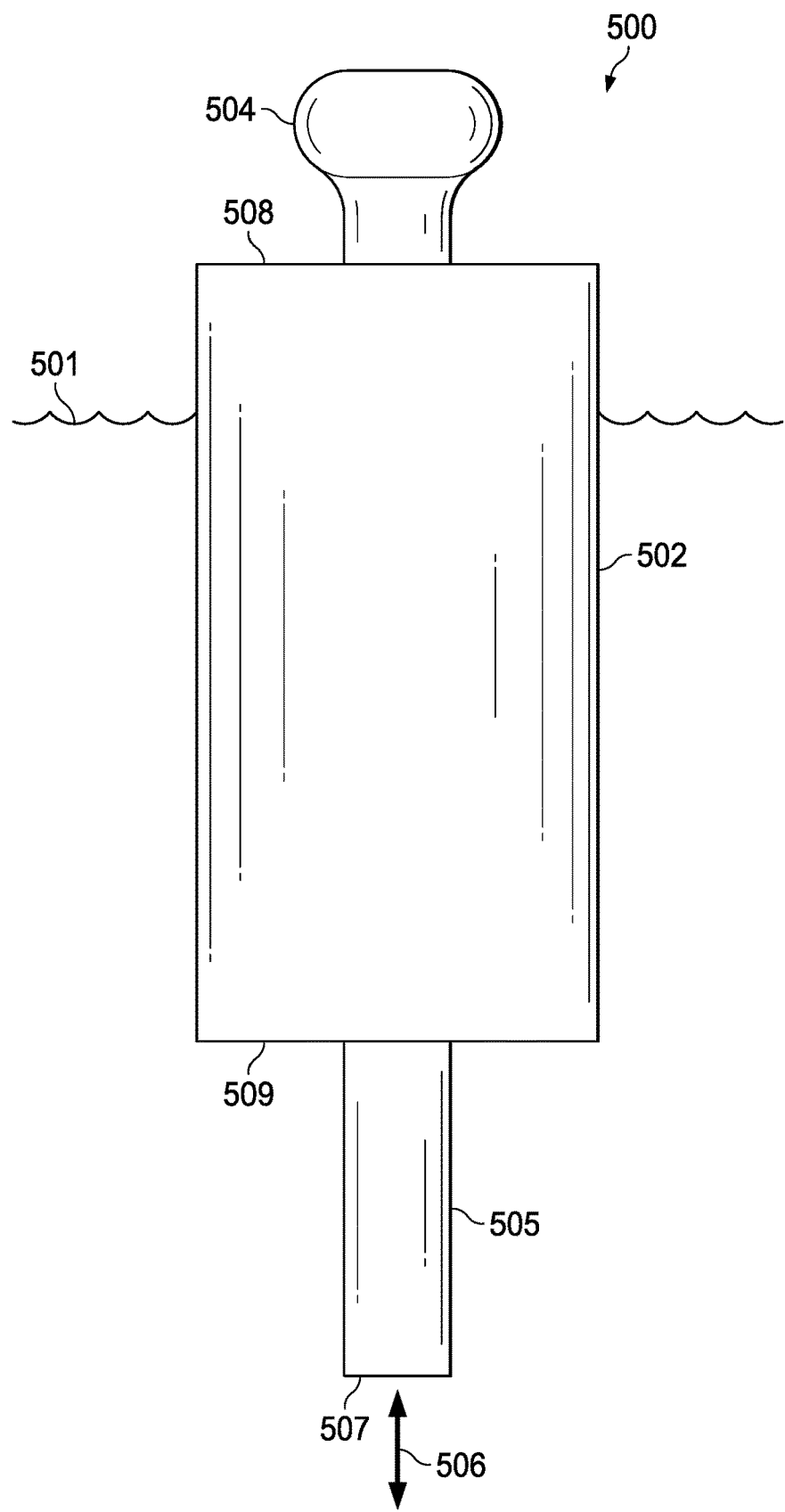
FIG. 25 is a side view of the fifth embodiment.

FIG. 25 shows a side view of the same embodiment 500 of the current disclosure that is illustrated in FIG. 24.

Figure 26:
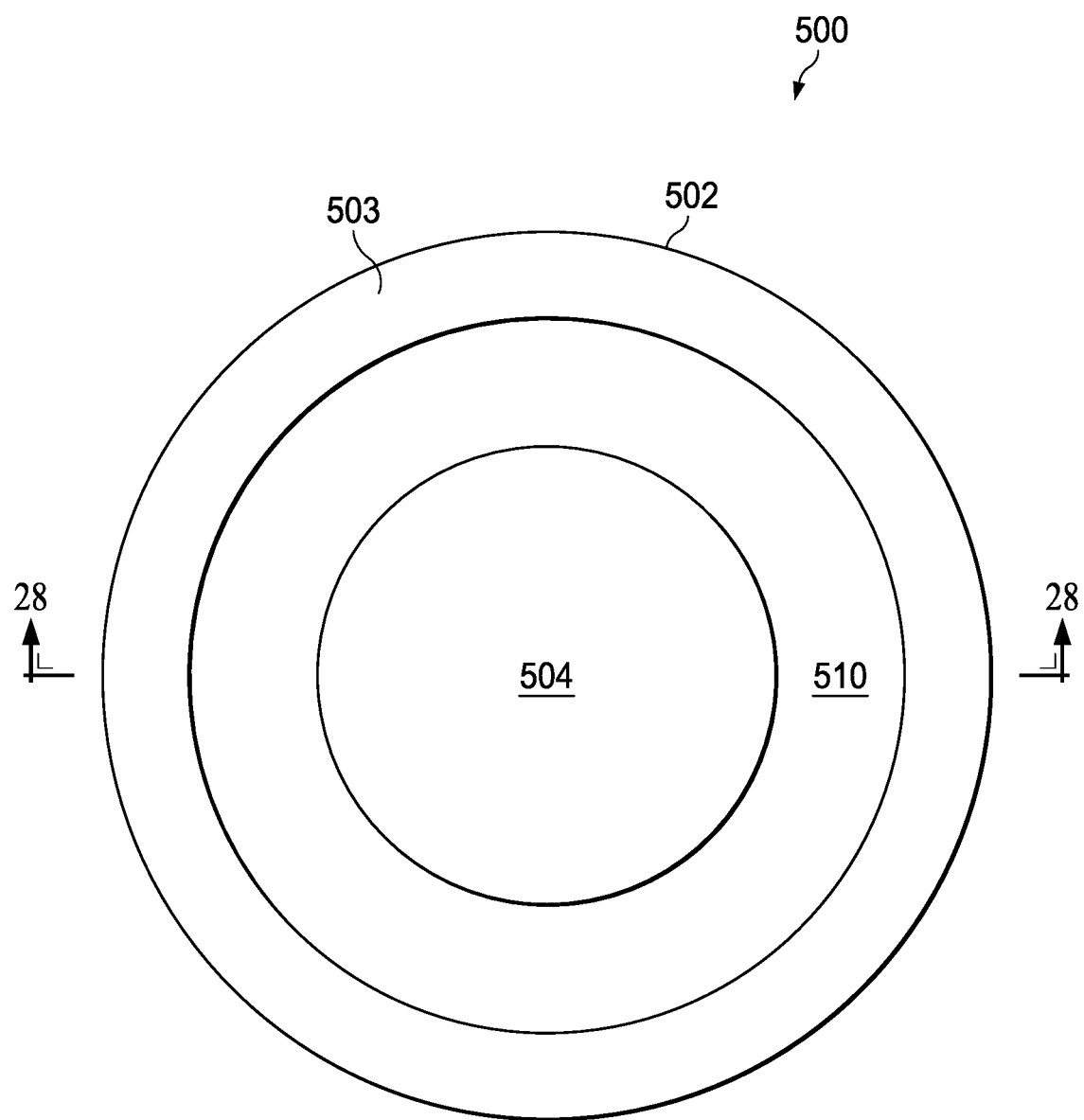
FIG. 26 is a top-down view of the fifth embodiment.

FIG. 26 shows a top-down view of the same embodiment 500 of the current disclosure that is illustrated in FIGS. 24 and 25. Between the peripheral, and/or toroidal, radiated-wave-generation chamber 503 and the central power take off mechanism 504 is an annular space or central channel 510 open to the body of water outside the embodiment through aperture 509 (in FIGS. 24 and 25) and therefore typically containing water at an average, nominal, and/or resting level approximately equal to the level of the surface (501 in FIG. 25) of the body of water on which the embodiment floats, and open to the atmosphere above through aperture 508 (in FIGS. 24 and 25). In response to wave action at the embodiment, the radiated-wave-generation chamber tends to produce radiated waves, adjacent to the surface of water within the annular space 510, that tend to radiate from the outer periphery of the radiated-wave-generation chamber toward the power take off near a center of the central channel 510.

Figure 27:
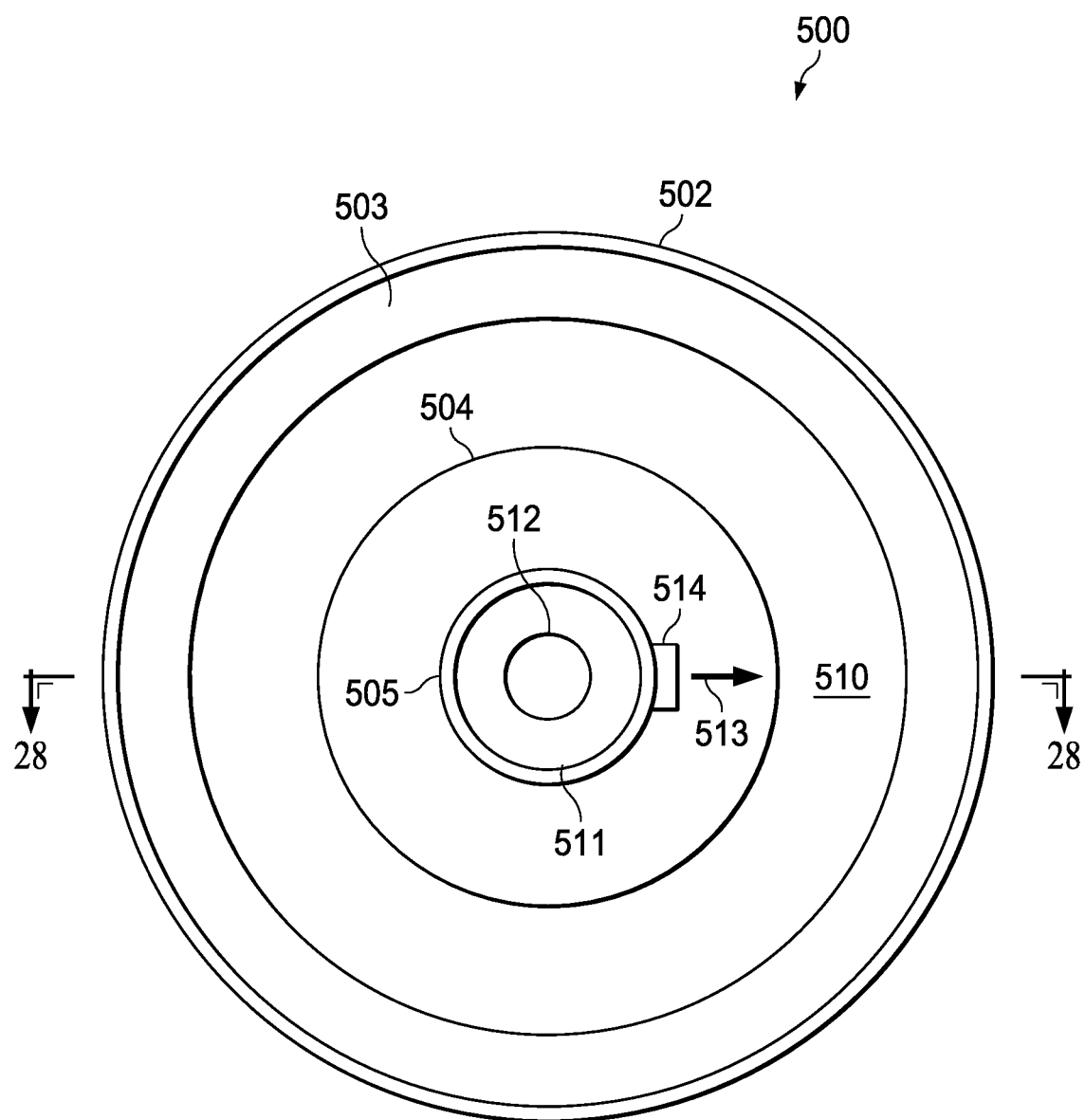
FIG. 27 is a bottom-up view of the fifth embodiment.

FIG. 27 shows a bottom-up view of the same embodiment 500 of the current disclosure that is illustrated in FIGS. 24-26. At an upper end of constricted tube 505 is a frusto-conical constriction 511. And, at an upper end of the tube, inside the upper bulbous portion 504 is an aperture 512 through and/or from which pressurized water is periodically, and/or occasionally, ejected into the pressurized water reservoir within the upper bulbous portion. Pressurized water trapped within the water reservoir inside the upper bulbous portion, flows 513 out of the water reservoir, and back into the body of water from which it originated, through a water turbine 514 which tends to cause the water turbine to rotate, and the rotations of which tend to energize a generator operably connected to the water turbine (not shown, i.e. a generator incorporated within a hubless turbine) which causes the generator to produce electrical power.

Figure 28:
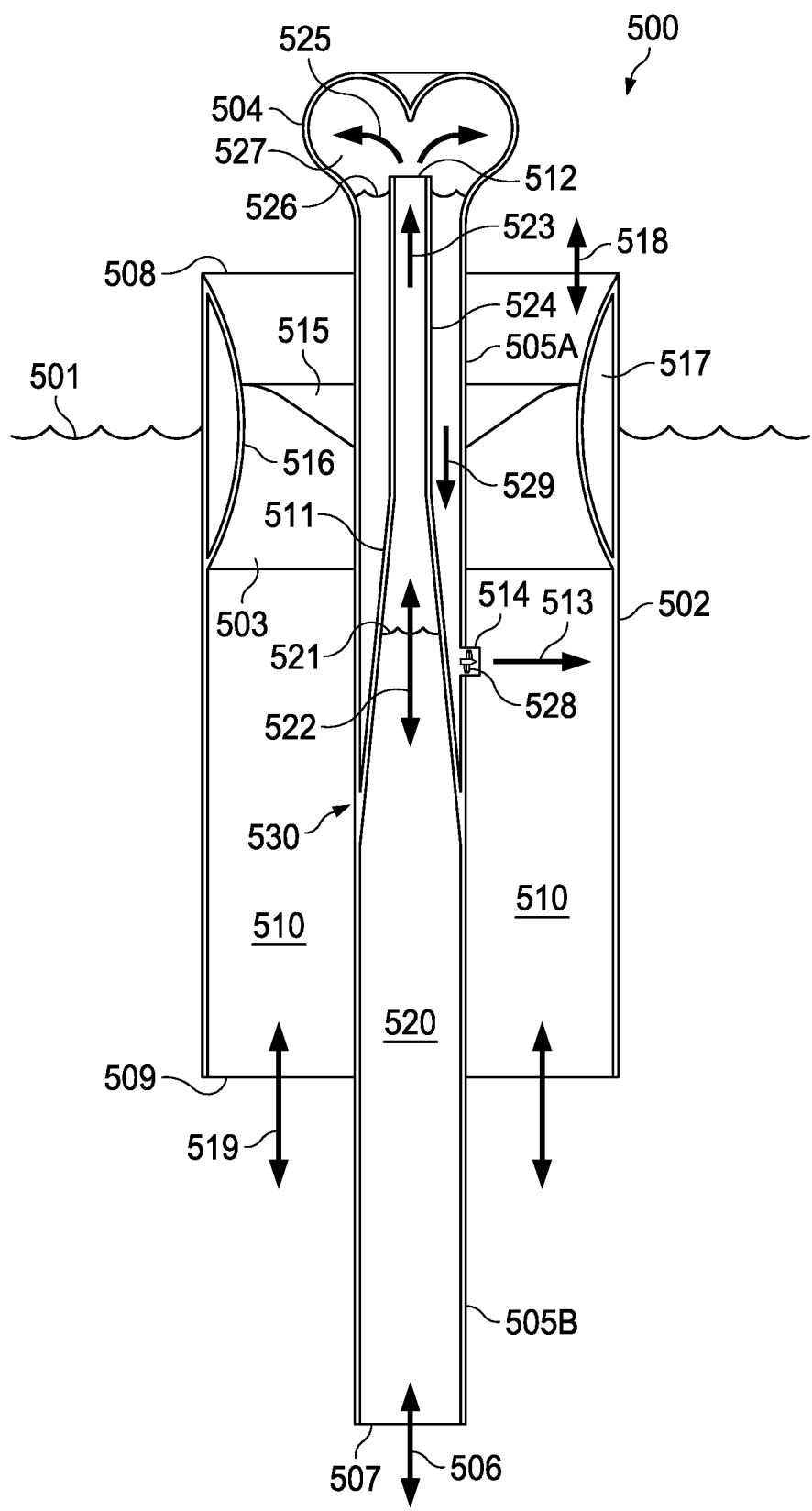
FIG. 28 is a side sectional view of the fifth embodiment.

FIG. 28 shows a side sectional view of the same embodiment 500 of the present disclosure that is illustrated in FIGS. 24-27 with the section plane being taken along line 28-28 of FIGS. 26 and 27.

The embodiment illustrated in FIG. 28 comprises, incorporates, utilizes, and/or includes, an approximately cylindrical, and/or toroidal, radiated-wave producing and reflecting structure similar to the one illustrated in FIGS. 19-23. It also comprises, incorporates, utilizes, and/or includes, a central heave-energized electrical power producing wave-energy converter similar in some respects to some pressurized-air-driven embodiments of the invention disclosed in U.S. Pat. No. 11,118,559.

When the embodiment 500 is moved, especially when moved vertically, relative to the surface 501 of the body of water on which the embodiment floats, water within the annular space defined by the embodiment's inner tubular channel, e.g. the channel laterally surrounded by cylindrical outer hull or radiated-wave reflector 502 and open to the body of water on which the embodiment floats through, and/or by means of, aperture and/or mouth 509, tends to be perturbed by the convex innermost wall 516 of the embodiment's radiated-wave-generation chamber 503, thereby tending to initiate, energize, perpetuate, radiate, and/or amplify, an oscillating wave 515, similar to a standing wave, adjacent to an upper surface 515 of the water within the embodiment's annular space 510.

With respect to the embodiment 500 illustrated in FIGS. 24-28, the height of the water within the embodiment's central channel 510, and therefore the embodiment's "inner" draft with respect to that inner volume of water, act in concert with the "outer" draft of the embodiment with respect to the surface 501 of the body of water on which the embodiment floats, to manifest and/or create a net and/or effective degree of buoyancy and/or a net upward buoyant force. Therefore, with respect to some embodiments of the present disclosure, such as the embodiment illustrated in FIGS. 24-28, i.e. with respect to some embodiments which characteristically manifest certain patterns of oscillating radiated waves within their central channels, as the water within the embodiment's central channel rises and falls (through the production of an oscillating pattern of radiated waves, e.g. 515, similar to a standing wave) in response to a rising and falling of the embodiment with respect to the surface of the body of water on which the embodiment floats, so too these types of embodiments tend to rise and fall somewhat resonantly with the rising and falling of the water within their respective central channels.

The cylindrical radiated-wave producing and reflecting structure of embodiment 500 comprises, incorporates, utilizes, and/or includes, a radiated-wave-generation chamber 503 which is hollow, and the space 517 within that annular and/or toroidal hollow radiated-wave-generation chamber is filled with nitrogen gas. The cylindrical radiated-wave producing and reflecting structure contains upper 508 and lower 509 mouths or apertures through which fluid may freely flow 518 and 519, respectively.

The wave-energy converter 504-505 approximately coaxial with a longitudinal axis of the approximately cylindrical outer hull or radiated-wave reflector 502 of the embodiment 500 is designed so as to be maximally and/or optimally responsive to heaving motions having a frequency similar to, if not exactly, the frequency at which the embodiment tends to resonantly bob up and down, e.g. when excited by the heave of a passing wave, and the frequency of the radiated waves which it tends to induce, radiate, and/or generate within the water adjacent to an upper surface 515 of the water within the embodiment's central channel 510.

When the embodiment heaves up and down in response to a passing incident and/or environmental wave, it tends to capture some of the energy of the passing incident and/or environmental wave and release it as radiated waves 515 imparted to, and/or radiated across, the water within its central channel 510. These radiated waves tend to exchange energy with the embodiment thereby causing the embodiment to bob at its resonant frequency even if and when the incident and/or environmental wave has passed.

As the embodiment bobs up and down, water flows 506 into and out from the constricted tube 505. As the embodiment bobs up and down, and as water flows into and out from the constricted tube, an upper surface 521 of the water 520 within the constricted tube tends to move 522 up and down. When the embodiment moves downward, the walls of the constricted portion 511 of its constricted tube tend to collide with the water 520 within the tube. Each such collision tends to pressurize the water within and/or near the constriction causing two things to happen.

First, a portion of that pressurized water tends to flow 523 upward rapidly through an upper portion 524 of the constricted tube, e.g. through a narrower segment of the constricted tube 505B above the constricted segment and tending to match the minimum diameter of the constricted segment. Occasionally, and/or periodically, a portion of water flows 523 upward with enough energy to be ejected 525 from the upper mouth 512 of the constricted tube, whereafter that ejected water tends to fall into, and be trapped within, a water reservoir 526. A pocket 527 of pressurized air above the water reservoir adds pressure to the water within the water reservoir. It also pushes down the nominal and/or resting upper surface 521 of the water within the constricted tube to a level where the pressure of the air approximately matches the hydrostatic pressure of the water at that same depth, and/or horizontal position, outside the constricted tube.

Second, the water 520 below the constriction tends to be accelerated downward and it therefore tends to flow downward until the pressure of the water 501 outside the lower mouth 507 of the constricted tube 505B slows its descent and then accelerates it upward.

The regular, periodic, and/or occasional, collision of an upwardly accelerating column of water 520 within the constricted tube, and a downwardly accelerating embodiment, tends to cause energetic collisions between such upward flowing water and a downward moving constricted tube walls 511, each time tending to produce a relatively sudden increase in the pressure of the water within and/or near the constricted portion 511 of the constricted tube 505B.

Pressurized water within the embodiment's water reservoir 526 flows 529 down to, and then flows 513 out through, and out of, a water turbine 528 to which a generator rotor is attached, and which generator rotor interacts with a complementary generator stator embedded in the wall of the water turbine's housing 514, pipe, and/or effluent channel. Thus, when energized by water flowing out of the water reservoir, the water turbine and generator assembly 513, 514, and 528 tends to produce electrical energy.

A lower cylindrical portion 505B of the constricted tube 511, 520, and 524 is joined (at seam 530) to another cylindrical tube 505A of equal diameter so as to eliminate the production of any secondary radiated waves and/or radiation which would tend to reduce the electrical-energy-generation efficiency of the embodiment. Because of an approximately constant cross-sectional area within tube 505A and 505B, vertical movements of that tube within the water both within and without the central channel 510 do not tend to alter their displacement of that water and therefore tend to move without a concomitant and/or consequential production and/or radiation of radiated waves. The upper 505A extension of the lower 505B cylindrical tube, in conjunction with an upper portion 511 and 524 of the constricted tube, provides the vessel, enclosure, and/or chamber, in which the water reservoir 526 is contained, held, trapped, and/or stored.

Because the embodiment's wave-energy converter 504-505 has been designed to exhibit maximum sensitivity to a heaving frequency equal to the resonant frequency of the embodiment, and/or to the characteristic frequency of the radiated waves the embodiment produces within its central channel 510 which tends to cause, maintain, and/or amplify, a complementary heaving of the embodiment at that frequency, the wave-energy converter tends to be energized, at least in part, by a single, and/or narrow band, of heave frequencies, and will therefore tend to operate at greater efficiency than would a similar wave-energy converter whose design is compromised so as to provide it with a requisite sensitivity and/or power-generation efficiency across a relatively broad range of incident- and/or environmental-wave frequencies.

Figure 29:
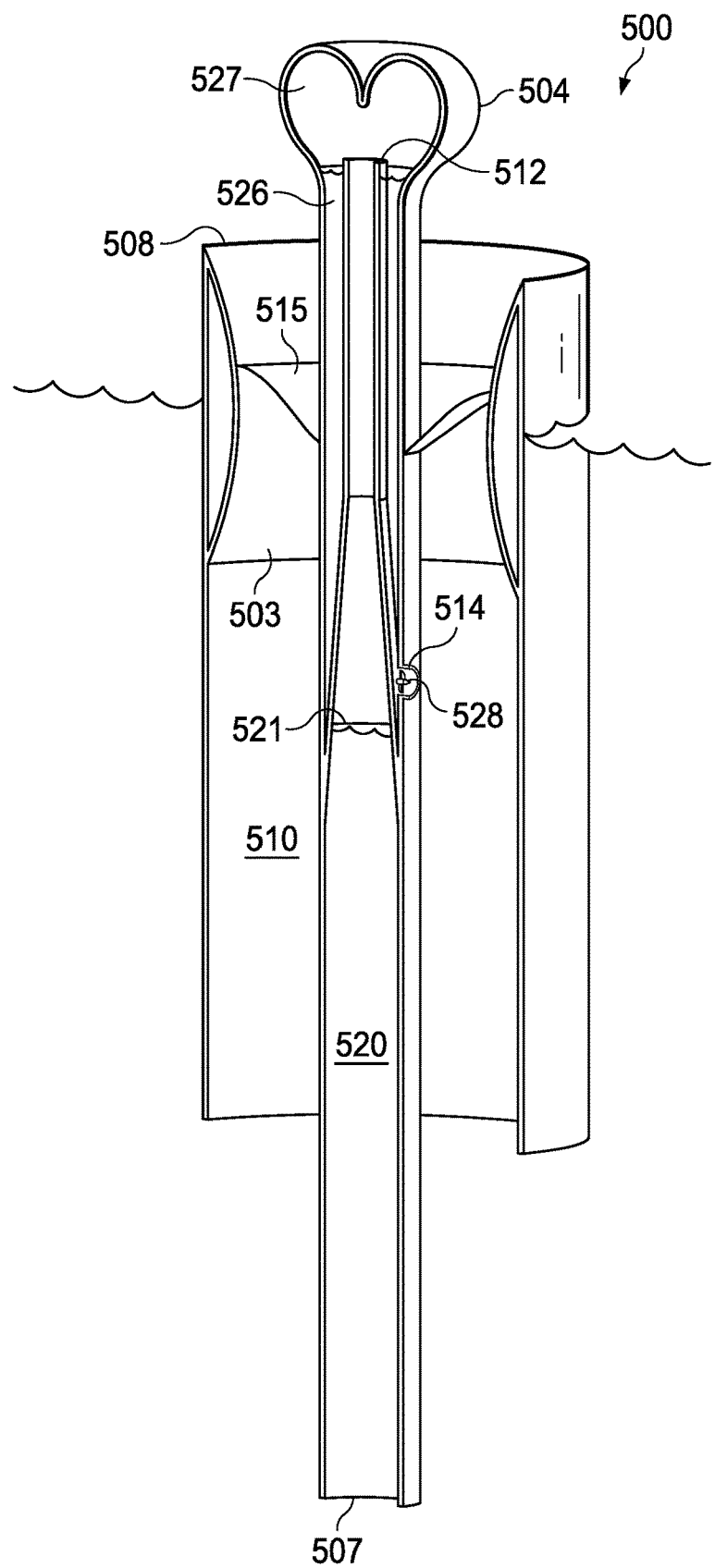
FIG. 29 is a perspective side sectional view of the fifth embodiment.

FIG. 29 shows a perspective view of the side sectional view illustrated in FIG. 28. As with FIG. 28, the section plane is taken along line 28-28 of FIGS. 26 and 27.

The radiated-wave reflector 502 of the embodiment 500 illustrated in FIGS. 24-29 is approximately cylindrical. However, the scope of the present disclosure includes, but is not limited to, similar embodiments which incorporate, include, and/or utilize, radiated-wave reflectors of any shape, including, but not limited to, radiated-wave reflectors that have cross-sectional shapes that are: elliptical, parabolic, and hyperbolic.

Figure 30:
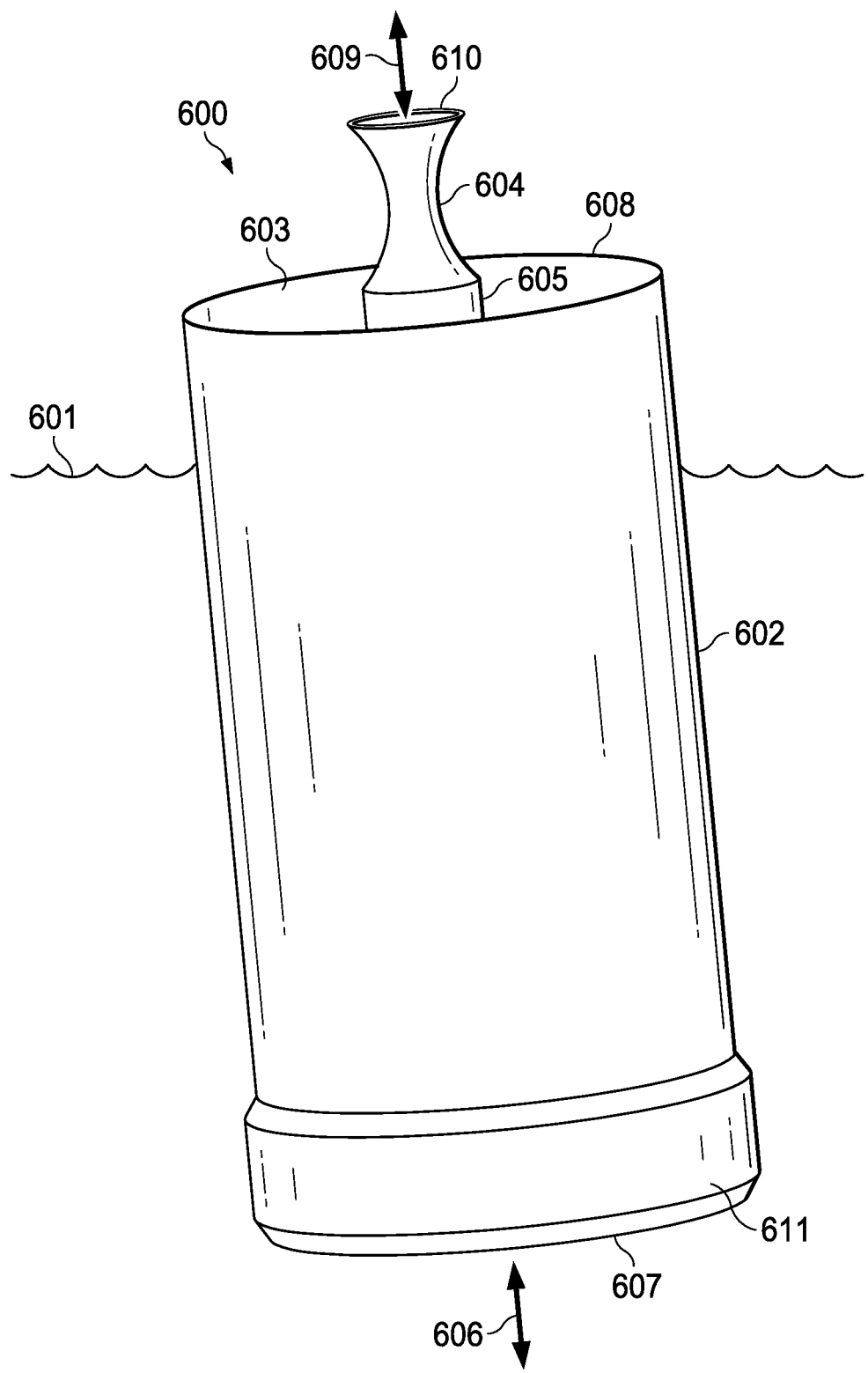
FIG. 30 is a perspective side view of a sixth embodiment.

FIG. 30 shows a perspective side view of an embodiment 600 of the current disclosure.

The embodiment 600 is buoyant and floats adjacent to an upper surface 601 of a body of water over which waves pass. The embodiment illustrated in FIG. 30 is similar to the embodiment illustrated in FIGS. 19-23. Like the embodiment illustrated in FIGS. 19-23, the embodiment illustrated in FIG. 30 comprises, incorporates, utilizes, and/or includes, an approximately cylindrical outer hull or radiated-wave reflector 602 (402 in FIG. 22), and a radiated-wave-generation chamber 603 (407 in FIG. 22). However, unlike the embodiment illustrated in FIGS. 19-23, the embodiment illustrated in FIG. 30 further comprises, incorporates, utilizes, and/or includes, an "oscillating water column" (OWC) power take off mechanism 604-605.

The embodiment's approximately cylindrical exterior wall 602, hull, or radiated-wave reflector, surrounds and/or defines a central channel into which water may flow 606 in, and from which water may flow 606 out, through a lower mouth 607 of the central channel. An upper mouth 608 of the central channel likewise permits atmospheric air to flow into, and out from, the embodiment's central channel.

As the level and/or height of the water within the embodiment's central channel, relative to the OWC 604-605, moves up and down, e.g. due to an oscillating wave similar to a standing wave, then a mouth and/or aperture at a lower end of the OWC allows portions of the water to flow into and out from the lower approximately cylindrical tube 605 of the OWC. When the level of the water within the embodiment's central channel rises with respect to the OWC, air in an upper portion 604/605 of the OWC is compressed which tends to cause a portion of that air to flow 609 out of the upper, constricted portion 610 of the OWC, which tends to cause an air turbine therein to rotate, which, in turn, tends to cause an operably connected generator to produce electrical power. When the level of the water within the embodiment's central channel falls with respect to the OWC, air in an upper portion 604/605 of the OWC is decompressed, and/or its pressure is reduced, which tends to cause air from the atmosphere to flow 609 into the upper, constricted portion 610 of the OWC, which again tends to cause the air turbine therein to rotate, which, in turn, tends to cause the operably connected generator to produce electrical power. The OWC of the embodiment illustrated in FIG. 30 comprises, incorporates, utilizes, and/or includes, an air turbine which tends to rotate in the same direction regardless of the direction with which air flows through it, e.g. a Wells turbine.

The scope of the present disclosure includes, but is not limited to, embodiments which comprise, incorporate, utilize, and/or include, any type of air turbine and/or water turbine, bidirectional turbines (rotate the same direction regardless of the direction of fluid flow through their blades), unidirectional turbines (reverse their direction of rotation in response to reversals of the direction of fluid flow through their blades), any type of electrical generator, and any type of consumer of hydraulic power.

The scope of the present disclosure is not limited by the type, if any, of power take off used to convert an energy manifested by an embodiment.

The embodiment illustrated in FIG. 30 comprises, incorporates, utilizes, and/or includes, a circumferential ballast or weight 611 mounted, attached, and/or connected to an outside of a lower portion of the cylindrical outer hull or radiated-wave reflector 602.

Figure 31:
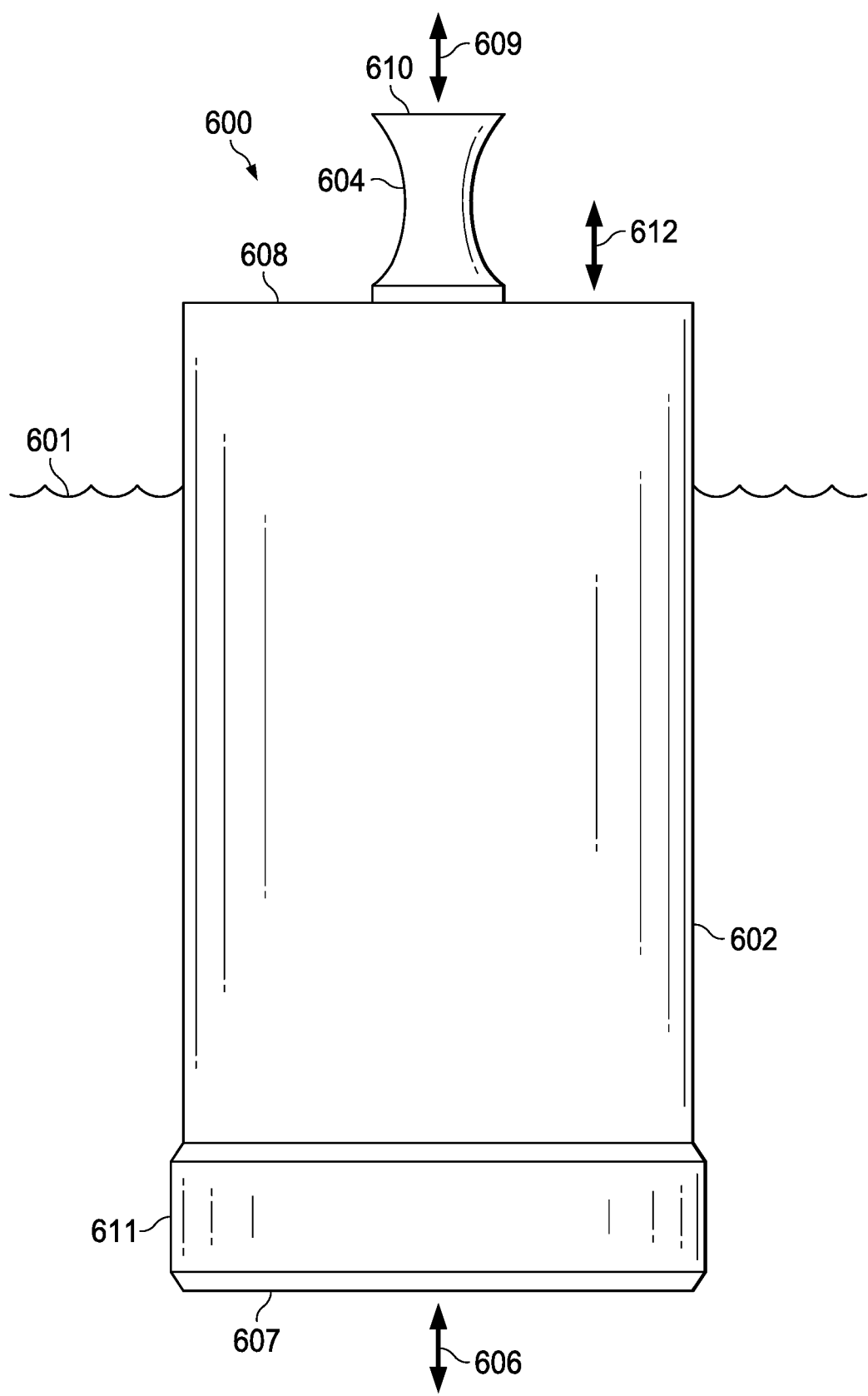
FIG. 31 is a side view of the sixth embodiment.

FIG. 31 shows a side view of the same embodiment 600 of the current disclosure that is illustrated in FIG. 30. An upper mouth 608 of the central channel permits atmospheric air to flow 612 into, and out from, the embodiment's central channel.

Figure 32:
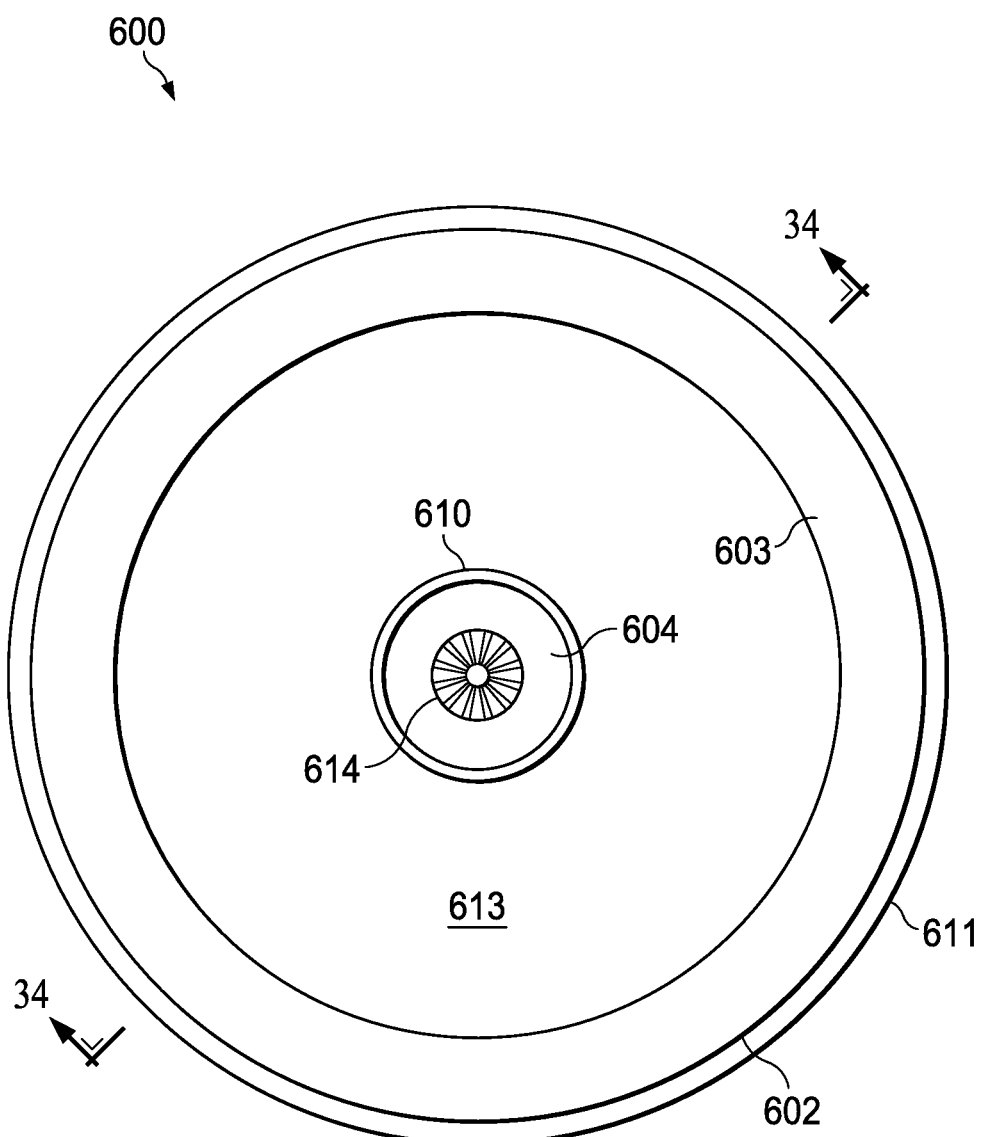
FIG. 32 is a top-down view of the sixth embodiment.

FIG. 32 shows a top-down view of the same embodiment 600 of the current disclosure that is illustrated in FIGS. 30 and 31. When the embodiment is at rest on a calm waveless body of water a lower portion of the central channel 613 is filled with water to a level approximately equal to the level of the surface (601 in FIG. 31) of the body of water outside the embodiment on which the embodiment floats, and a level that places an upper surface of that central-channel water at an elevation that is approximately adjacent to a vertical center of the radiated-wave-generation chamber 603. And, when the embodiment is at rest on a calm waveless body of water an upper portion of the central channel 613 is filled with air.

Positioned at the center of the constricted portion 604 of the OWC, where the constriction is greatest and/or where a horizontal cross-sectional area of the OWC tube is at a minimum, is an air turbine 614 that is operably connected to a hubless generator (not shown) in which magnets mounted about the periphery of the air turbine (i.e. a generator rotor) are rotated adjacent to a concentric generator stator such that rotation of the air turbine causes the generator to produce electrical power.

Figure 33:
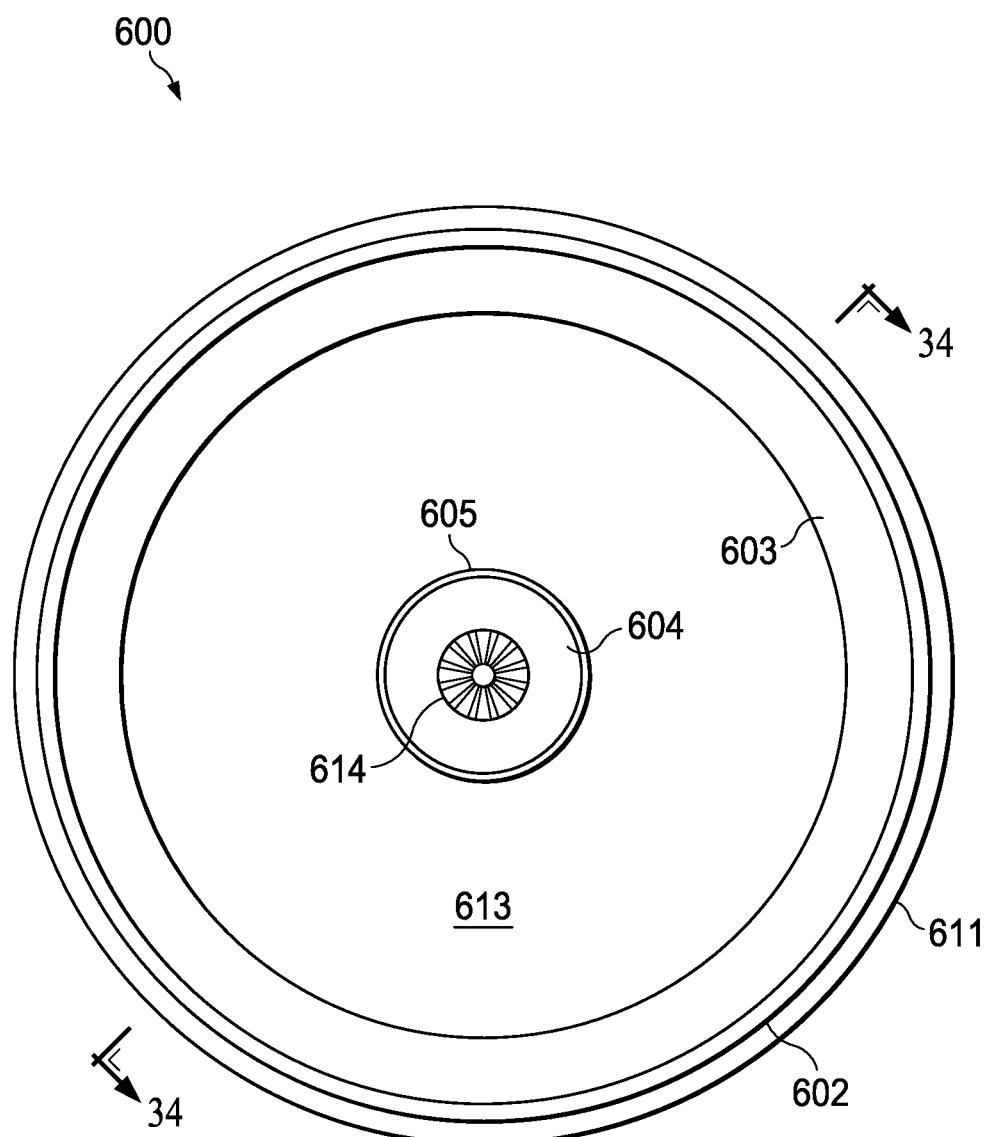
FIG. 33 is a bottom-up view of the sixth embodiment.

FIG. 33 shows a bottom-up view of the same embodiment 600 of the current disclosure that is illustrated in FIGS. 30-32.

Figure 34:
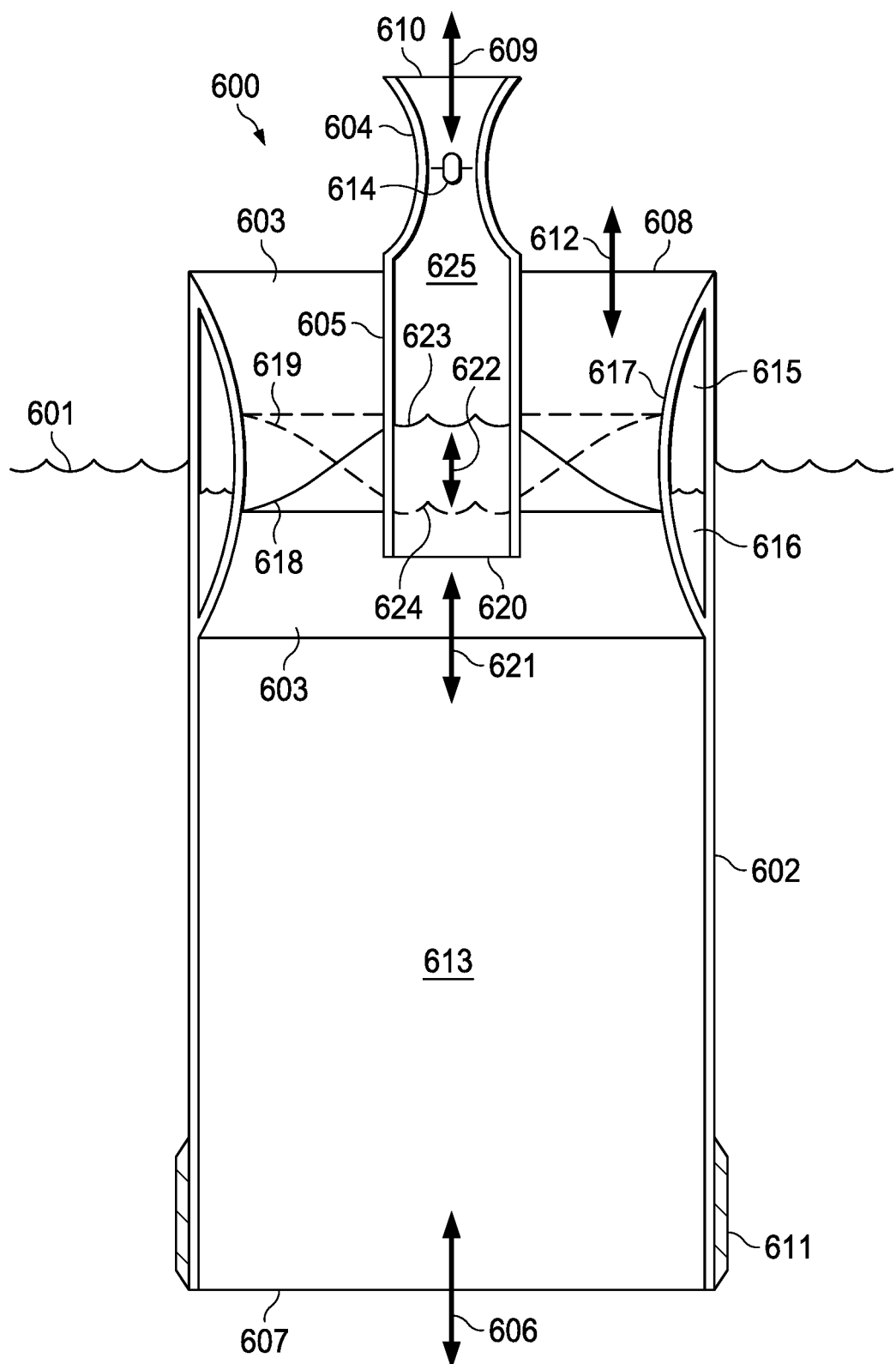
FIG. 34 is a side sectional view of the sixth embodiment.

FIG. 34 shows a side sectional view of the same embodiment 600 of the present disclosure that is illustrated in FIGS. 30-33 with the section plane being taken along line 34-34 of FIGS. 32 and 33.

The embodiment 600 is buoyant in part because of an air pocket 615 enclosed and/or trapped within a hollow interior of the embodiment's radiated-wave-generation chamber 603. The embodiment includes ballast and/or weight comprised in part of the panels, and/or walls of which the cylindrical or radiated-wave reflector and the radiated-wave-generation chamber are comprised; a reservoir, volume, and/or mass of water 616 enclosed and/or trapped within a hollow interior of the embodiment's radiated-wave-generation chamber; and an annular ring of negatively buoyant material 611 (e.g. steel) attached, affixed, and/or connected, to an outer surface of a lower portion of the approximately cylindrical exterior wall 602, hull, or radiated-wave reflector.

The scope of the present disclosure includes, but is not limited to, embodiments which include, comprise, incorporate, and/or utilize, ballast and/or weight comprising, at least in part: water, gravel, cementitious material, iron, steel, rocks, and wood.

In response to passing waves, the embodiment will tend to rise due to its inherent buoyancy, and fall due to its inherent weight, with respect to the surface 601 of the body of water over which the waves pass.

As the embodiment rises with respect to the body of water on which the embodiment floats, the embodiment's radiated-wave-generation chamber 603 will also tend to rise with respect to an upper surface 618/619 of the water present within the central channel defined by the cylindrical hull or radiated-wave reflector 602. That rising will tend to reduce the volume of water within the cylindrical hull or radiated-wave reflector which the radiated-wave-generation chamber displaces, thereby tending to create a volumetric deficit in the water adjacent to the inner exterior of the radiated-wave-generation chamber. That volumetric deficit tends to occur in the water adjacent to the innermost curved wall 617 of the radiated-wave-generation chamber. And this relatively sudden drop in the level of the water adjacent to the radiated-wave-generation chamber tends to create the trough 618 of a radiated wave which then tends to radiate away from the radiated-wave-generation chamber and towards the center of the central channel 613.

As the embodiment falls with respect to the body of water on which the embodiment floats, the embodiment's radiated-wave-generation chamber 603 will also tend to fall with respect to an upper surface 618/619 of the water present within the central channel defined by the cylindrical hull or radiated-wave reflector 602. That falling will tend to increase the volume of water within the cylindrical hull or radiated-wave reflector which the radiated-wave-generation chamber displaces thereby tending to create a volumetric surplus in the water adjacent to the inner exterior of the radiated-wave-generation chamber. That volumetric surplus tends to occur in the water adjacent to the innermost curved wall 617 of the radiated-wave-generation chamber. And this relatively sudden increase in the level of the water adjacent to the radiated-wave-generation chamber tends to create the crest 619 of a radiated wave which then tends to radiate away from the radiated-wave-generation chamber and towards the center of the central channel 613.

A succession, series, train, and/or sequence, of radiated-wave-generation-chamber 603 induced volumetric deficits and volumetric surpluses tends to create a radiating and/or oscillatory pattern of circular radiated waves, each travelling toward the center of the central channel 613, up to an outer surface of the OWC tube where they tend to be reflected back toward the radiated-wave-generation chamber, where they tend to be reflected back toward the center. An embodiment's characteristic pattern of oscillating circular radiated waves is similar to a standing and/or resonant wave and tends to trap wave energy within an upper portion of the water within the central channel.

As the water within the upper portion of the central channel 613 rises and falls in an oscillatory pattern similar to that of a standing wave, a draft (i.e. depth) of the radiated-wave-generation chamber 603 tends to be successively increased and decreased, respectively, which tends to cause an oscillating pattern of buoyant and gravitational forces that tends to induce and/or reinforce a rising and falling of the embodiment within the body of water at the frequency of the oscillating radiated waves trapped within the embodiment's central channel.

As the water near the center of an upper portion of the central channel 613 rises 618 and falls 619 in an oscillatory pattern similar to that of a standing wave, a level of water at the lower mouth 620, and/or the effective depth of that lower mouth, similarly increases and decreases, respectively, which causes water to flow 621 into and out of the lower mouth of the OWC. This oscillatory flow 621 of water into and out of the OWC raises and lowers 622 an upper level of water within the OWC between a relatively high level 623 and a relatively low level 624.

When the level of the water within the OWC rises, e.g. from 624 to 623, the pocket of air 625 within the OWC is compressed which tends to force some of that air to flow 609 out of the OWC and through the air turbine 614 positioned in the throat of, and/or within a constriction in, the upper portion and/or part 604 of the OWC, and then into the atmosphere above the embodiment. When the level of the water within the OWC falls, e.g. from 623 to 624, the pocket of air 625 within the OWC is decompressed which tends to cause air to be pulled from the atmosphere and into 609 the OWC and through the air turbine 614 positioned in the throat of, and/or within a constriction in, the upper portion and/or part 604 of the OWC.

When air flows outward and/or inward through the air turbine 614 in the throat of the OWC 604/605, the air turbine tends to be caused to rotate, which, in turn, tends to cause an operably connected and/or coupled generator (not shown) to produce electrical power.

Figure 35:
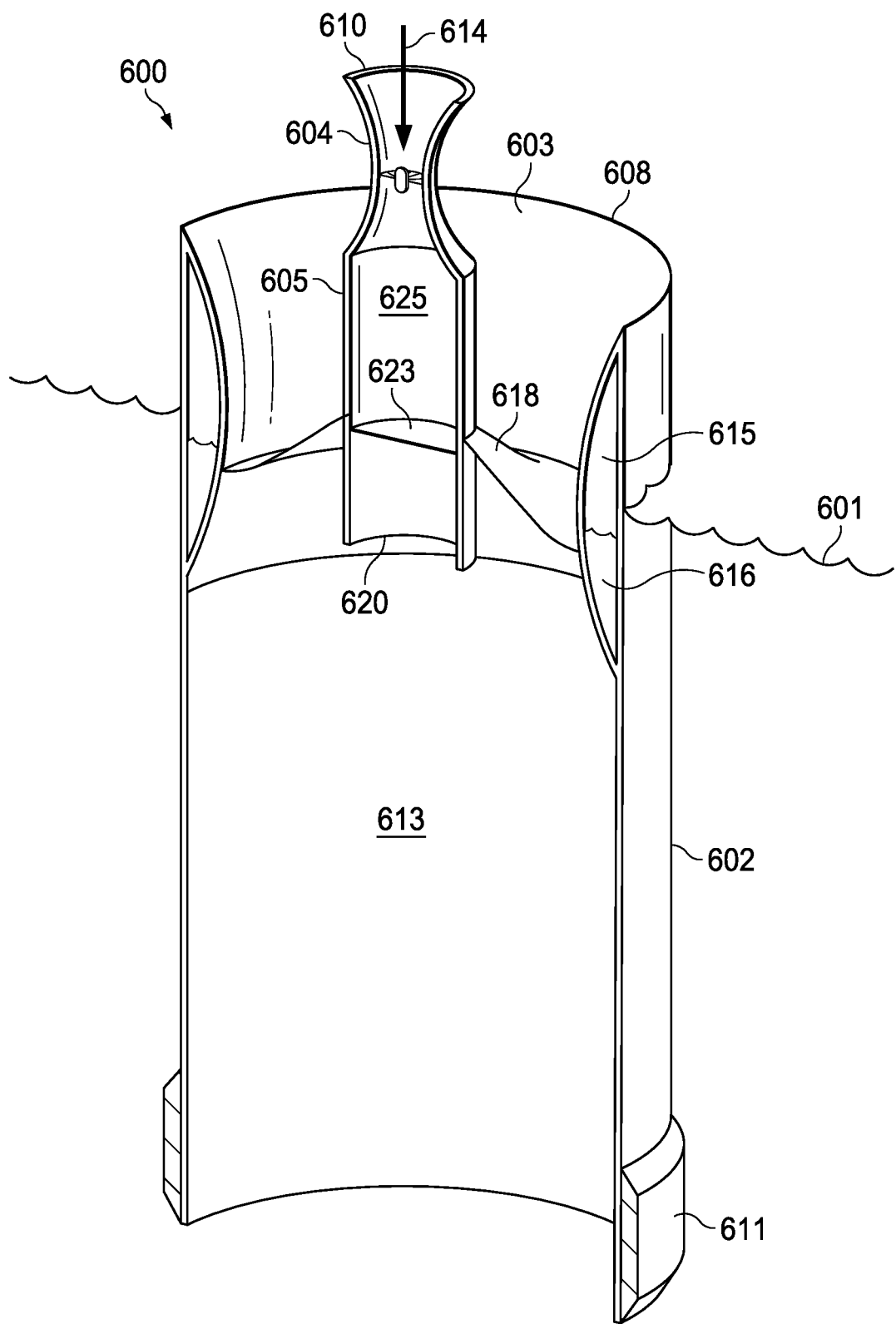
FIG. 35 is a perspective side sectional view of the sixth embodiment.

FIG. 35 shows a perspective view of the side sectional view illustrated in FIG. 34.

The scope of the present disclosure includes, but is not limited to, embodiments which contain, comprise, include, incorporate, and/or utilize, a straight-walled and/or tubular hull and/or radiated wave reflector coupled with a curved object, structure, element, and/or feature within an interior of the radiated wave reflector. The scope of the present disclosure includes, but is not limited to, embodiments which contain, comprise, include, incorporate, and/or utilize, a tubular element including, comprising, incorporating, incorporating, and/or utilizing, an annular, circular, and/or toroidal radiated wave generator affixed to, attached to, and/or incorporated within, an inner wall or surface of the tubular element.

The scope of the present disclosure includes, but is not limited to, embodiments which contain, comprise, include, incorporate, and/or utilize, a power take off mechanism, element, apparatus, and/or module. The scope of the present disclosure includes, but is not limited to, embodiments which do not contain, comprise, include, incorporate, and/or utilize, a power take off mechanism, element, apparatus, and/or module.

The scope of the present disclosure includes, but is not limited to, embodiments which do not contain, comprise, include, incorporate, and/or utilize, a port, gap, slit, and/or opening, suitable to facilitating the entry and exit of other vessels, e.g. autonomous underwater vehicles, autonomous surface vessels, etc.

The scope of the present disclosure includes, but is not limited to, embodiments which comprise, include, incorporate, and/or utilize, a feature, element, structure, and/or surface, which tends to produce and/or generate radiated waves in response to a movement of the embodiment relative to a surface of water, e.g. water within an enclosed volume, and/or water outside an enclosed volume. Such features, elements, structures, and/or surfaces, can be of any shape, curvature, geometry, design, and/or configuration, including, but not limited to, shapes which are at least partially spherical, triangular, rectangular, conical, and frustoconical.

The radiated-wave reflector 602 of the embodiment 600 illustrated in FIGS. 30-35 is approximately cylindrical. However, the scope of the present disclosure includes, but is not limited to, similar embodiments which incorporate, include, and/or utilize, radiated-wave reflectors of any shape, including, but not limited to, radiated-wave reflectors that have cross-sectional shapes that are: elliptical, parabolic, and hyperbolic.

The foregoing descriptions in conjunction with the associated drawings are intended to teach the inventors' best modes for carrying out the invention. However, a person of ordinary skill in the art will readily recognize and appreciate many modifications and substitutions that fall within the spirit of the present invention and it is intended that the scope of the invention include all such modifications and substitutions. Nothing in the description or drawings should be interpreted to be limiting or exclusory of such variations unless expressly so indicated.

We claim:

1. A buoyant wave energy converter having a pressurized upper component and a submergible hollow tubular lower component depending downwardly therefrom, comprising:
    a wave reflecting barrier spaced from and encircling the wave energy converter, said wave reflecting barrier having a height that is greater than a height of the pressurized upper component as measured from the pressurized upper component's highest surface to the pressurized upper component's lowest surface and less than a height of the hollow tubular lower component as measured from the lower tubular components highest surface to the lower tubular component's lowest surface, and the wave reflecting barrier further having a radially inwardly facing surface; and
    circumferentially spaced connectors rigidly attaching the wave reflecting barrier to the wave energy converter;
    wherein the radially inwardly facing surface of the wave reflecting barrier defines a cylinder having an open top and an open bottom.

2. The buoyant wave energy converter of claim 1, wherein the circumferentially spaced connectors are radial panels aligned vertically.

3. The buoyant wave energy converter of claim 2, wherein a height of the radial panels is equal to the height of the wave reflecting barrier.

4. The buoyant wave energy converter of claim 3, wherein the radial panels divide a volume enclosed by the wave reflecting barrier into equal sector shaped volumes.

5. The buoyant wave energy converter of claim 1, wherein an upper portion of the wave reflecting barrier's radially inwardly facing surface includes a convex profile.

6. The buoyant wave energy converter of claim 5, wherein the convex profile is vertically displaced below the pressurized upper component of the wave energy converter.

7. The buoyant wave energy converter of claim 1, wherein the wave reflecting barrier's radially inwardly facing surface is contoured to bias the wave energy converter vertically in response to radially emanating waves impinging said surface.

8. The buoyant wave energy converter of claim 1, wherein the wave reflecting barrier's radially inwardly facing surface defines a volume, and wherein said volume is substantially but not totally filled with water when said wave energy converter is placed in a body of water.

9. The buoyant wave energy converter of claim 1, wherein a buoyancy of the wave energy converter prevents the wave reflecting barrier from submerging when said wave energy converter is placed in a body of water.

10. A buoyant wave energy converter having a buoyant pressurized upper component and a submergible hollow tubular lower component depending downwardly therefrom, comprising:
    a wave reflecting barrier surrounding the wave energy converter, said wave reflecting barrier having a radially inwardly facing surface defining a volume, and wherein wave reflecting barrier is vertically disposed on the wave energy converter such that said volume is always substantially but not totally filled with water when said wave energy converter is placed in a body of water; and
    connectors rigidly attaching the wave reflecting barrier to the wave energy converters;
    wherein the radially inwardly facing surface of the wave reflecting barrier defines a cylinder having an open top and an open bottom.

11. A buoyant wave energy converter having a pressurized upper component and a submergible hollow tubular lower component depending downwardly therefrom, comprising:
    a wave reflecting barrier surrounding the wave energy converter, said wave reflecting barrier having a radially inwardly facing surface contoured to bias the wave energy converter vertically in response to radially emanating waves impinging said surface; and
    connectors rigidly attaching the wave reflecting barrier to the wave energy converter, said connectors are circumferentially spaced radial panels having a height that is equal to a height of the wave reflecting barrier.

12. A buoyant wave energy converter having a pressurized upper component and a submergible hollow tubular lower component depending downwardly therefrom, comprising:
    a wave reflecting barrier spaced from and encircling the buoyant wave energy converter, said wave reflecting barrier having a radially inwardly facing surface having a substantially vertical orientation, and the wave reflecting barrier further having a bottommost edge below a waterline of the wave energy converter; and
    circumferentially spaced connectors rigidly attaching the wave reflecting barrier to the wave energy converter;

wherein the radially inwardly facing surface of the wave reflecting barrier defines a cylinder having an open top and an open bottom.

13. The buoyant wave energy converter of claim 12, wherein the circumferentially spaced connectors are radial panels aligned vertically.

14. The buoyant wave energy converter of claim 12, wherein the radially inwardly facing surface of the wave reflecting barrier defines a cylinder.

15. The buoyant wave energy converter of claim 12, wherein a distance between said inwardly facing surface and said wave energy converter is adjustable to optimize an energy recovery of the radially emanating wave.

16. The buoyant wave energy converter of claim 12, wherein an upper portion of the wave reflecting barrier's radially inwardly facing surface includes a convex profile.

17. The buoyant wave energy converter of claim 16, wherein the convex profile is vertically displaced below the upper component of the wave energy converter.

18. The buoyant wave energy converter of claim 12, wherein the wave reflecting barrier's radially inwardly facing surface is contoured to bias the wave energy converter vertically in response to radially emanating waves impinging said surface.

19. The buoyant wave energy converter of claim 12, wherein the wave reflecting barrier's radially inwardly facing surface defines a volume, and wherein said volume is substantially but not totally filled with water when said wave energy converter is placed in a body of water.

20. The buoyant wave energy converter of claim 12, wherein a buoyancy of the wave energy converter is sufficient to prevent the wave reflecting barrier from submerging when said wave energy converter is placed in a body of water.

* * * * *